(12) United States Patent
Matsuura et al.

(10) Patent No.: US 10,004,937 B2
(45) Date of Patent: *Jun. 26, 2018

(54) WEARABLE MODULAR RESISTANCE UNIT

(71) Applicant: Tau Orthopedics, LLC, Coto de Caza, CA (US)

(72) Inventors: Belinko K. Matsuura, Solano Beach, CA (US); David G. Matsuura, Solano Beach, CA (US); Kaitlin von Hoffmann, Sunnyvale, CA (US); Gerard von Hoffmann, Coto de Caza, CA (US)

(73) Assignee: Tau Orthopedics LLC, Rancho Santa Fe, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/665,947

(22) Filed: Mar. 23, 2015

(65) Prior Publication Data

US 2015/0190669 A1    Jul. 9, 2015

Related U.S. Application Data

(63) Continuation-in-part of application No. 12/951,947, filed on Nov. 22, 2010, now Pat. No. 8,986,177,
(Continued)

(51) Int. Cl.
*A63B 21/00* (2006.01)
*A63B 21/02* (2006.01)
(Continued)

(52) U.S. Cl.
CPC .......... *A63B 21/4025* (2015.10); *A61B 5/002* (2013.01); *A61B 5/1118* (2013.01);
(Continued)

(58) Field of Classification Search
USPC ...................................................... 482/1–148
See application file for complete search history.

(56) References Cited

U.S. PATENT DOCUMENTS

| 2,611,610 | A | * | 9/1952 | Hara | .................. | A63B 69/0059 |
|           |   |   |        |      |                   | 473/257 |
| 2,664,566 | A |   | 1/1954 | Mianulli | | |

(Continued)

FOREIGN PATENT DOCUMENTS

| WO | 2014138504 A2 | 9/2014 |
| WO | 2014153201 A1 | 9/2014 |
| WO | 2014194257    | 12/2014 |

OTHER PUBLICATIONS

Written Opinion Issued on PCT Application Serial No. PCT/US16/23715 by ISA/US dated Aug. 11, 2016, pp. 1-6.
(Continued)

*Primary Examiner* — Stephen R Crow
(74) *Attorney, Agent, or Firm* — Ashley Sloat; Aurora Consulting LLC

(57) ABSTRACT

Disclosed is a muscle toning garment with resistance elements, which may be fluid filled dampers. The garment provides resistance to movement throughout an angular range of motion. The garment may be low profile, and worn by a wearer as a primary garment or beneath conventional clothing. Toning may thereby be accomplished throughout the wearer's normal daily activities, without the need for access to conventional exercise equipment. Alternatively, the device may be worn as a supplemental training tool during conventional training techniques. Sensors may be provided for sensing any of a variety of biometric parameters and for determining exerted power or calories consumed.

21 Claims, 28 Drawing Sheets

Related U.S. Application Data which is a continuation-in-part of application No. 12/797,718, filed on Jun. 10, 2010, now abandoned, application No. 14/665,947, which is a continuation-in-part of application No. 14/450,228, filed on Aug. 2, 2014, now Pat. No. 9,433,814, which is a continuation-in-part of application No. 14/217,576, filed on Mar. 18, 2014, now Pat. No. 9,327,156, which is a continuation-in-part of application No. 14/192,805, filed on Feb. 27, 2014, now abandoned.

(60) Provisional application No. 61/218,607, filed on Jun. 19, 2009.

(51) Int. Cl.

| | | |
|---|---|---|
| *A63B 23/04* | (2006.01) | |
| *A63B 21/16* | (2006.01) | |
| *A61B 5/00* | (2006.01) | |
| *A61B 5/11* | (2006.01) | |
| *A61B 5/22* | (2006.01) | |
| *A63B 21/008* | (2006.01) | |
| *A63B 21/055* | (2006.01) | |
| *A63B 23/02* | (2006.01) | |
| *A63B 23/12* | (2006.01) | |
| *A63B 69/00* | (2006.01) | |
| *A63B 21/005* | (2006.01) | |
| *A63B 21/012* | (2006.01) | |
| *A63B 24/00* | (2006.01) | |
| *A63B 71/00* | (2006.01) | |
| *A63B 71/06* | (2006.01) | |
| *A61B 5/0488* | (2006.01) | |

(52) U.S. Cl.
CPC .............. *A61B 5/22* (2013.01); *A61B 5/486* (2013.01); *A63B 21/0004* (2013.01); *A63B 21/00185* (2013.01); *A63B 21/00845* (2015.10); *A63B 21/02* (2013.01); *A63B 21/16* (2013.01); *A63B 21/4001* (2015.10); *A63B 21/4011* (2015.10); *A63B 21/4017* (2015.10); *A63B 21/4039* (2015.10); *A63B 21/4043* (2015.10); *A63B 23/04* (2013.01); *A63B 23/0482* (2013.01); *A63B 23/0494* (2013.01); *A61B 5/0488* (2013.01); *A61B 5/4866* (2013.01); *A63B 21/008* (2013.01); *A63B 21/0053* (2013.01); *A63B 21/0083* (2013.01); *A63B 21/0087* (2013.01); *A63B 21/00189* (2013.01); *A63B 21/012* (2013.01); *A63B 21/023* (2013.01); *A63B 21/028* (2013.01); *A63B 21/0552* (2013.01); *A63B 21/159* (2013.01); *A63B 21/4047* (2015.10); *A63B 23/02* (2013.01); *A63B 23/1245* (2013.01); *A63B 23/1281* (2013.01); *A63B 24/0087* (2013.01); *A63B 69/0028* (2013.01); *A63B 2071/0081* (2013.01); *A63B 2071/0655* (2013.01); *A63B 2208/14* (2013.01); *A63B 2209/02* (2013.01); *A63B 2209/10* (2013.01); *A63B 2220/44* (2013.01); *A63B 2220/51* (2013.01); *A63B 2225/20* (2013.01); *A63B 2225/50* (2013.01); *A63B 2225/54* (2013.01); *A63B 2230/202* (2013.01); *A63B 2230/205* (2013.01); *A63B 2230/207* (2013.01); *A63B 2230/42* (2013.01); *A63B 2230/50* (2013.01); *A63B 2230/60* (2013.01); *A63B 2230/65* (2013.01); *A63B 2230/75* (2013.01)

(56) References Cited

U.S. PATENT DOCUMENTS

| | | |
|---|---|---|
| 2,832,334 A | 4/1958 | Whitelaw |
| 4,065,814 A | 1/1978 | Fox |
| 4,621,620 A | 11/1986 | Anderson |
| 4,829,989 A | 5/1989 | Deamer |
| 4,875,677 A | 10/1989 | Tetreault |
| 4,910,802 A | 3/1990 | Malloy |
| 5,052,379 A | 10/1991 | Airy et al. |
| 5,176,600 A | 1/1993 | Wilkinson |
| 5,201,074 A | 4/1993 | Dicker |
| 5,263,923 A | 11/1993 | Fujimoto |
| 5,306,222 A | 4/1994 | Wilkinson |
| 5,308,305 A | 5/1994 | Romney |
| 5,337,737 A | 8/1994 | Rubin et al. |
| 5,465,428 A | 11/1995 | Earl |
| 5,472,412 A | 12/1995 | Knoth |
| 5,527,244 A | 6/1996 | Waller et al. |
| 5,553,322 A | 9/1996 | Cebo-Johnson |
| 5,606,745 A | 3/1997 | Gray |
| 5,662,595 A | 9/1997 | Chesher et al. |
| 5,685,811 A | 11/1997 | McShane et al. |
| 5,720,042 A | 2/1998 | Wilkinson |
| 5,749,840 A | 5/1998 | Mitchell et al. |
| 5,788,618 A | 8/1998 | Joutras |
| 5,792,034 A | 8/1998 | Kozlovsky |
| RE35,940 E | 10/1998 | Heinz et al. |
| 5,842,959 A | 12/1998 | Wilkinson |
| 5,867,827 A | 2/1999 | Wilkinson |
| 5,875,491 A | 3/1999 | Wilkinson |
| 5,937,441 A | 8/1999 | Raines |
| 5,960,474 A | 10/1999 | Dicker et al. |
| 5,976,063 A | 11/1999 | Joutras et al. |
| 5,978,966 A | 11/1999 | Dicker et al. |
| 5,993,362 A | 11/1999 | Ghobadi |
| 6,039,677 A | 3/2000 | Spletzer |
| 6,129,638 A | 10/2000 | Davis |
| 6,176,816 B1 | 1/2001 | Dicker et al. |
| 6,186,970 B1 | 2/2001 | Fujii et al. |
| 6,210,354 B1 | 4/2001 | Ousdal |
| 6,231,488 B1 | 5/2001 | Dicker et al. |
| 6,314,580 B1 | 11/2001 | Greenberg et al. |
| 6,397,496 B1 | 6/2002 | Seymour |
| 6,409,693 B1 | 6/2002 | Brannigan |
| 6,440,094 B1 | 8/2002 | Maas |
| 6,656,097 B2 | 12/2003 | Karecki |
| 6,666,801 B1 | 12/2003 | Michalow |
| 6,757,916 B2 | 7/2004 | Mah et al. |
| 6,786,855 B2 * | 9/2004 | Prichard ............ A63B 21/04 482/127 |
| 6,834,752 B2 | 12/2004 | Irby et al. |
| 6,872,187 B1 | 3/2005 | Stark et al. |
| 6,954,968 B1 | 10/2005 | Sitbon |
| 7,048,098 B1 | 5/2006 | Moradian |
| 7,087,003 B1 | 8/2006 | Katterjohn |
| 7,153,246 B2 | 12/2006 | Koscielny et al. |
| 7,235,038 B2 | 6/2007 | Liao |
| 7,599,806 B2 | 10/2009 | Hauschildt |
| 7,608,026 B1 | 10/2009 | Nicassio |
| 7,682,322 B2 | 3/2010 | Engelman |
| 7,744,511 B2 | 6/2010 | Gregoriev |
| 7,758,481 B2 | 7/2010 | Drennan |
| 7,845,023 B2 | 12/2010 | Swatee |
| 7,849,518 B2 | 12/2010 | Moore et al. |
| 7,861,319 B2 | 1/2011 | Tony |
| 7,874,970 B2 | 1/2011 | Glisan |
| 7,931,571 B2 | 4/2011 | Bernardoni |
| 7,931,609 B2 | 4/2011 | Blanchard |
| 8,043,243 B2 | 10/2011 | Nathanson |
| 8,052,379 B2 * | 11/2011 | Gammack ............ F04F 5/16 415/126 |
| 8,060,945 B2 | 11/2011 | Adarraga |
| 8,063,644 B2 | 11/2011 | Rezvani et al. |
| 8,171,570 B2 * | 5/2012 | Adarraga ............ A61F 5/0102 2/22 |
| 8,273,001 B2 | 9/2012 | Karecki |
| 8,312,646 B2 | 11/2012 | Meschter et al. |

(56) References Cited

U.S. PATENT DOCUMENTS

| | | |
|---|---|---|
| 8,544,114 B2 | 10/2013 | Williams et al. |
| 8,555,415 B2 | 10/2013 | Bradstreet et al. |
| 8,663,133 B2 | 3/2014 | Johnson et al. |
| 8,663,142 B1 | 3/2014 | Pansiera |
| 8,707,463 B2 | 4/2014 | Orloff |
| 8,762,077 B2 | 6/2014 | Redmond et al. |
| 8,784,350 B2 | 7/2014 | Cohen |
| 8,870,798 B2 | 10/2014 | Coleman |
| 8,939,924 B1 | 1/2015 | Paulos |
| 8,951,136 B1 | 2/2015 | Booher |
| 9,192,806 B2 | 11/2015 | Mial |
| 9,204,811 B2 | 12/2015 | Wright |
| 9,327,156 B2 | 5/2016 | von Hoffmann et al. |
| 9,375,603 B2 * | 6/2016 | Matsuura ............... A63B 21/02 |
| 9,656,117 B2 * | 5/2017 | von Hoffmann .. A63B 21/4025 |
| 9,750,998 B2 * | 9/2017 | Dawson ............ A63B 69/3641 |
| 2001/0029224 A1 | 10/2001 | Karecki |
| 2004/0040064 A1 | 3/2004 | Mah et al. |
| 2004/0116260 A1 | 6/2004 | Drennan |
| 2005/0101887 A1 | 5/2005 | Stark et al. |
| 2005/0148915 A1 | 7/2005 | Nathanson et al. |
| 2005/0239602 A1 | 10/2005 | Cordova et al. |
| 2005/0255975 A1 | 11/2005 | Horn |
| 2005/0261113 A1 | 11/2005 | Wilkinson |
| 2005/0275416 A1 | 12/2005 | Hervieux et al. |
| 2006/0000478 A1 | 1/2006 | Taylor |
| 2006/0016649 A1 | 1/2006 | Gordaninejad et al. |
| 2006/0046910 A1 | 3/2006 | Rastegar et al. |
| 2006/0046913 A1 | 3/2006 | Squittieri |
| 2006/0079825 A1 | 4/2006 | Hilton et al. |
| 2006/0096818 A1 | 5/2006 | Moradian |
| 2006/0272071 A1 | 12/2006 | Mickle |
| 2006/0287621 A1 | 12/2006 | Atkinson et al. |
| 2007/0010772 A1 | 1/2007 | Ryan |
| 2007/0016120 A1 | 1/2007 | Latronica et al. |
| 2007/0032359 A1 | 2/2007 | Toronto |
| 2007/0100265 A1 | 5/2007 | Gamada |
| 2007/0123997 A1 | 5/2007 | Herr et al. |
| 2007/0135279 A1 | 6/2007 | Purdy et al. |
| 2007/0219074 A1 | 9/2007 | Pride |
| 2007/0245835 A1 | 10/2007 | Hauschildt |
| 2008/0009771 A1 | 1/2008 | Perry et al. |
| 2008/0026917 A1 | 1/2008 | Campana |
| 2008/0108918 A1 | 5/2008 | Joutras et al. |
| 2008/0218310 A1 | 9/2008 | Alten et al. |
| 2008/0222769 A1 | 9/2008 | Natonson |
| 2009/0253325 A1 | 10/2009 | Brookstein et al. |
| 2009/0281394 A1 | 11/2009 | Russell et al. |
| 2010/0029224 A1 | 2/2010 | Urushihara et al. |
| 2010/0041527 A1 | 2/2010 | Miller |
| 2010/0075557 A1 | 3/2010 | Shteiyer |
| 2010/0077527 A1 | 4/2010 | Lee et al. |
| 2010/0144490 A1 | 6/2010 | Purdy et al. |
| 2010/0175730 A1 * | 7/2010 | Ruddy .................... A45B 9/04 135/77 |
| 2010/0193304 A1 | 8/2010 | Böse et al. |
| 2010/0223717 A1 | 9/2010 | Foy et al. |
| 2010/0248915 A1 | 9/2010 | Gibson-Horn |
| 2010/0267525 A1 | 10/2010 | Tanner |
| 2010/0323859 A1 | 12/2010 | von Hoffmann |
| 2011/0010001 A1 | 1/2011 | Chung et al. |
| 2011/0111932 A1 | 5/2011 | von Hoffmann et al. |
| 2011/0126335 A1 | 6/2011 | Schultz |
| 2011/0231986 A1 | 9/2011 | Waldie et al. |
| 2011/0247127 A1 | 10/2011 | Pou |
| 2011/0266323 A1 | 11/2011 | Kazerooni et al. |
| 2012/0094811 A1 | 4/2012 | Karecki |
| 2012/0116258 A1 | 5/2012 | Lee |
| 2012/0136231 A1 | 5/2012 | Markel |
| 2012/0225755 A1 | 9/2012 | Lloyd |
| 2012/0259255 A1 | 10/2012 | Tomlinson et al. |
| 2013/0040783 A1 | 2/2013 | Duda et al. |
| 2013/0085040 A1 | 4/2013 | Bowers |
| 2013/0130874 A1 | 5/2013 | Richardson et al. |
| 2013/0150218 A1 | 6/2013 | Mial |
| 2013/0190147 A1 | 7/2013 | Luo et al. |
| 2013/0207889 A1 | 8/2013 | Chang et al. |
| 2013/0247330 A1 | 9/2013 | Daul et al. |
| 2013/0298301 A1 | 11/2013 | Petrakis et al. |
| 2013/0338472 A1 | 12/2013 | Marcia Barber et al. |
| 2014/0109282 A1 | 4/2014 | White et al. |
| 2014/0173934 A1 | 6/2014 | Bell |
| 2014/0222943 A1 | 8/2014 | Oleson et al. |
| 2014/0238153 A1 | 8/2014 | Wood et al. |
| 2014/0265677 A1 | 9/2014 | Orand |
| 2014/0278125 A1 | 9/2014 | Balakrishnan et al. |
| 2014/0278229 A1 | 9/2014 | Hong et al. |
| 2014/0296761 A1 | 10/2014 | Yamamoto et al. |
| 2014/0313049 A1 | 10/2014 | Doherty |
| 2014/0358053 A1 | 12/2014 | Triolo et al. |
| 2014/0364771 A1 | 12/2014 | Pitts et al. |
| 2014/0379275 A1 | 12/2014 | Yuen et al. |
| 2015/0031970 A1 | 1/2015 | Lain |
| 2015/0045703 A1 | 2/2015 | Strausser et al. |
| 2015/0057128 A1 | 2/2015 | Ishii |
| 2015/0148619 A1 | 5/2015 | Berg et al. |
| 2015/0190669 A1 * | 7/2015 | Matsuura ............... A63B 21/02 482/8 |
| 2015/0230719 A1 | 8/2015 | Berg et al. |
| 2016/0062333 A1 | 3/2016 | Jayaraman |
| 2016/0107309 A1 | 4/2016 | Walsh et al. |
| 2016/0128632 A1 | 5/2016 | Wiebe et al. |
| 2016/0199685 A1 * | 7/2016 | von Hoffmann .. A63B 21/4025 482/8 |
| 2017/0274249 A1 * | 9/2017 | Moebius ............ A63B 24/0062 |

OTHER PUBLICATIONS

International Search Report Issued on PCT Application Serial No. PCT/US16/23715 by ISA/US dated Aug. 11, 2016, pp. 1-4.

* cited by examiner

WEARABLE MODULAR RESISTANCE UNIT

CROSS-REFERENCE TO RELATED APPLICATIONS

This application is a continuation-in-part of U.S. patent application Ser. No. 12/951,947, filed on Nov. 22, 2010, now U.S. Pat. No. 8,986,177, which is a continuation-in-part of U.S. patent application Ser. No. 12/797,718, filed on Jun. 10, 2010 which claims the benefit of U.S. Provisional Application No. 61/218,607, filed Jun. 19, 2009. This application is also a continuation-in-part of U.S. patent application Ser. No. 14/450,228 filed Aug. 2, 2014, which is a continuation in part of U.S. patent application Ser. No. 14/217,576 filed Mar. 18, 2014, which is a continuation in part of U.S. patent application Ser. No. 14/192,805 filed Feb. 27, 2014. The entireties of all of the foregoing applications are hereby incorporated by reference herein.

BACKGROUND OF THE INVENTION

Resistance training, sometimes known as weight training or strength training, is a specialized method of conditioning designed to increase muscle strength, muscle endurance, tone and muscle power. Resistance training refers to the use of any one or a combination of training methods which may include resistance machines, dumbbells, barbells, body weight, and rubber tubing.

The goal of resistance training, according to the American Sports Medicine Institute (ASMI), is to "gradually and progressively overload the musculoskeletal system so it gets stronger." This is accomplished by exerting effort against a specific opposing force such as that generated by elastic resistance (i.e. resistance to being stretched or bent). Exercises are isotonic if a body part is moving against the force. Exercises are isometric if a body part is holding still against the force. Resistance exercise is used to develop the strength and size of skeletal muscles. Full range of motion is important in resistance training because muscle overload occurs only at the specific joint angles where the muscle is worked. Properly performed, resistance training can provide significant functional benefits and improvement in overall health and well-being.

Research shows that regular resistance training will strengthen and tone muscles and increase bone mass. Resistance training should not be confused with weightlifting, power lifting or bodybuilding, which are competitive sports involving different types of strength training with non-elastic forces such as gravity (weight training or plyometrics) an immovable resistance (isometrics, usually the body's own muscles or a structural feature such as a door frame).

Whether or not increased strength is an objective, repetitive resistance training can also be utilized to elevate aerobic metabolism, for the purpose of weight loss, and to enhance muscle tone.

Resistance exercise equipment has therefore developed into a popular tool used for conditioning, strength training, muscle building, and weight loss. Various types of resistance exercise equipment are known, such as free weights, exercise machines, and resistance exercise bands or tubing.

Various limitations exist with the prior art exercise devices. For example, many types of exercise equipment, such as free weights and most exercise machines, are not portable. With respect to exercise bands and tubing, they may need to be attached to a stationary object, such as a closed door or a heavy piece of furniture, and require sufficient space. This becomes a problem when, for example, the user wishes to perform resistance exercises in a location where such stationary objects or sufficient space are not readily found.

Resistance bands are also limited to a single resistance profile in which the amount of resistance changes as a function of angular displacement of the joint under load. This may result in under working the muscles at the front end of a motion cycle, and over working the muscles at the back end of the cycle. Conventional elastic devices also provide a unidirectional bias that varies in intensity throughout an angular range but not in direction. Such devices thus cannot work both the flexor and extensor muscles of a given motion segment without adjustment. Users of the foregoing devices are as a practical matter also quite limited in what else they may be able to simultaneously accomplish.

A need therefore exists for resistance based wearable toning equipment that may be used on its own without the need to employ other types of equipment, that free the wearer for other simultaneous activities, and that applies a non-elastic load throughout both a flexion and extension range of motion.

SUMMARY OF THE INVENTION

There is provided in accordance with one aspect of the present invention, a low profile, wearable, dynamic resistance toning device. The dynamic resistance device may comprise a garment having a waistband, for attachment around the waist of a wearer, a left leg and a right leg.

At least one left leg resistance unit and at least one right leg resistance unit is carried by the garment. The resistance units may impart single direction or bidirectional resistance to movement throughout a range of motion.

In accordance with one aspect of the present invention, there is provided a toning garment, comprising a waist; a left leg, extending across a left hip and optionally a left knee; a right leg, extending across a right hip and optionally a right knee; a left fluid filled damper at the left hip; a right fluid filled damper at the right hip; a left femoral lever connected to the left fluid filled damper; a right femoral lever connected to the right fluid filled damper; wherein at least a portion of the left and right femoral levers is axially reciprocally moveable with respect to adjacent portions of the left and right leg of the garment.

The left fluid filled damper may comprise a housing and a rotatable connector, wherein the housing is secured against rotation with respect to the waist. The housing may be secured to the garment by stitching. The rotatable connector may be linked to the leg so that flexion or extension at the hip causes the connector to rotate. The rotatable connector may be linked to the leg by a lever. The lever may be sufficiently flexible in the medial lateral direction to conform to the leg of a wearer when the garment is worn. The garment may further comprise at least one force dissipation panel attached to the lever. The left and right dampers may be removably secured to the garment. The garment may comprise a compression fabric.

In accordance with a further aspect of the present invention, a lower body toning garment is provided, comprising: a waist portion, a right leg and a left leg; a left rotation point on a lateral side of the left leg and a right rotation point on a lateral side of the right leg, the left and right rotation points functionally aligned with a transverse axis of rotation extending through the center of rotation of a wearer's right and left hip; a left resistance unit mounted at the left rotation point; a right resistance unit mounted at the right rotation point; each of the left and right resistance units comprising a housing and a lever arm rotatable through a range of motion with respect to the housing; wherein the housing for the left resistance unit is attached to the garment at the left rotation point and a left lever arm is attached to the left leg; and the housing for the right resistance unit is attached to the garment at the right rotation point and a right lever arm is attached to the right leg.

The garment may additionally comprise a force dissipation layer attached to each of the right and left resistance elements, to resist rotation of the resistance elements relative to the garment. The garment may additionally comprise a force dissipation layer attached to each of the right and left lever arms to enhance force transfer. Each of the left and right resistance units provide at least about 2 inch pounds of torque, and in some embodiments at least about 5 or 7 or 10 inch pounds of torque. Each of the left and right resistance units may comprise a fluid filled damper. Each of the left and right resistance units may be removably mounted to the garment. At least one of the left and right resistance units may comprises an electrical generator.

A modular resistance unit is also provided, for releasable connection to a toning garment. The modular resistance unit comprises a femoral lever having a proximal end and a distal end, a thickness and a width that exceeds a thickness, the lever arm conformable to the leg of a wearer when mounted on the toning garment such that the width faces the leg of a wearer in an as worn orientation; a resistance unit carried by the proximal end of the lever; a coupling on the resistance unit, for releasable coupling to a complementary coupling carried by the garment; configured such that when the femoral lever is secured to the leg of the garment, the coupling on the damper is connected to the complementary coupling on the garment and the garment is worn by a wearer, the modular resistance unit provides resistance to movement at the wearer's hip. The coupling may comprise an aperture for receiving a post carried by the garment. The modular resistance unit may further comprise a lock for locking the coupling on the resistance unit to the complementary coupling carried by the garment. The lock may comprise a rotatable knob or quick release button or lever.

In accordance with a further aspect of the invention, there is provided a wearable measurement system for measuring power exerted by the wearer against a resistive force, comprising at least one force sensor carried by a garment and configured for measuring force exerted by the wearer upon motion which is opposed by resistance provided by a resistance element carried by the garment.

There is further provided a resistance module, for releasable connection to a garment, comprising: a resistance element; a connector on the resistance element for releasable connection to the garment; and a femoral lever, moveable with respect to the connector. The resistance element may comprise a fluid damper, such as a rotary fluid damper. The resistance module may further comprise at least one force sensor, and optionally at least two or four or more force sensors. The force sensor may be carried by the femoral lever.

In accordance with a further aspect of the present invention, there is provided a wearable toning and exertion measurement system, comprising: a wearable support, a resistance element carried by the support; a sensor for sensing force exerted by the wearer; a processing module for processing sensed force data; and a transmitter for transmitting data to a remote device. The transmitter may be an ANT+ configured transmitter. The wearable measurement system may be configured to display exerted power and or calories consumed. The system may also include a sensor for measuring a biometric parameter such as blood oxygen saturation, or an input for receiving blood oxygen saturation data. A feedback effector such as a visual display, indicator light, audio display or tactile feedback device such as a vibrator may be provided to indicate to the wearer their status or change in status between aerobic and anaerobic metabolic pathway.

The present invention further provides a wearable support, for receiving a resistance module for providing resistance to movement across a range of motion. A selection of resistance modules may be provided, having different, graduated resistance ratings. The wearable support comprises a support body, for mounting on the body of a wearer; a docking station on the support, located on a first portion of the wearer's body in an as worn configuration; a first connector on the docking station, for receiving a resistance module; the first connector secured against rotation with respect to the support body; and a second connector on the support body, located on a second portion of the wearer's body in the as worn configuration, separated by the first portion by a motion segment. The support body may comprise a waist portion for encircling the waist of the wearer. The first connector may comprises a post for engaging an aperture on the resistance module. The second connector may be configured to removably receive a femoral lever attached to the resistance module.

Further features and advantages of the present invention will become apparent to those of skill in the art in view of the detailed description of preferred embodiments which follows, when considered together with attached drawings and claims.

DETAILED DESCRIPTION OF THE PREFERRED EMBODIMENT

Figure 1:
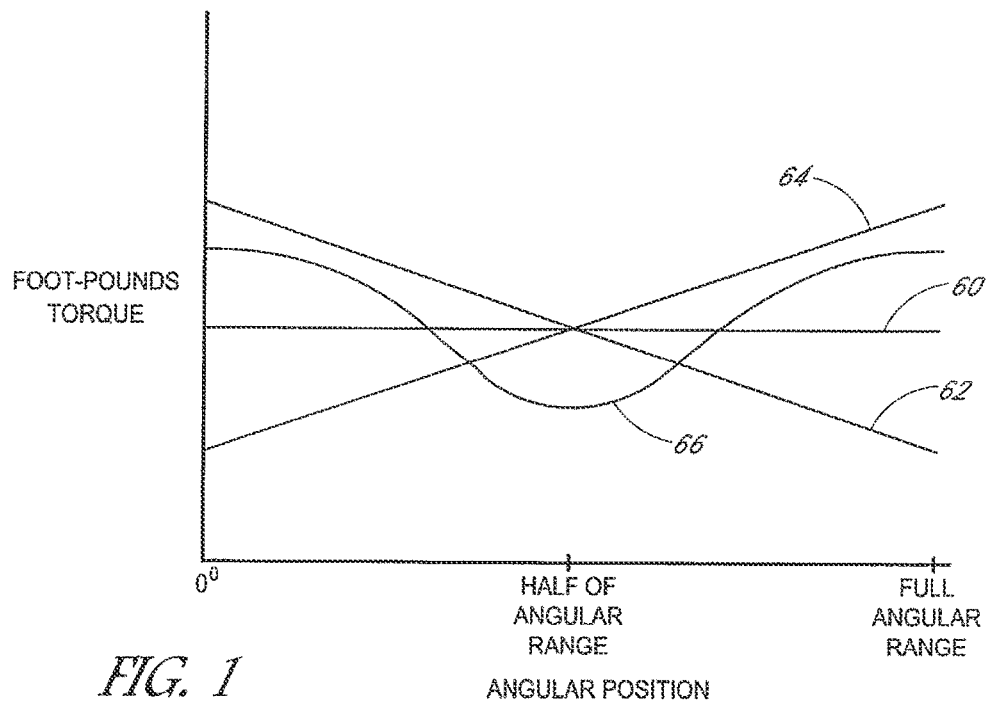
FIG. 1 is a plot of different resistance profiles as a function of angular rotation of a joint or motion segment.

Detailed descriptions of the preferred embodiments are provided herein. It is to be understood, however, that the present invention may be embodied in various other forms. Therefore, specific details disclosed herein are not to be interpreted as limiting, but rather as a basis for the claims and as a representative basis for teaching one skilled in the art to employ the present invention in virtually any appropriately detailed system, structure or manner.

In general, the devices in accordance with the present invention are designed to provide resistance to motion between a first region and a second region of the body such as across a simple or complex joint, (e.g., hip, knee, shoulder, elbow, etc.), throughout an angular range of motion. The resistance can be either unidirectional, to isolate a single muscle or muscle group, or preferably bidirectional to exercise opposing muscle pairs or muscle groups. Optionally, the device will be user adjustable to select uni or bidirectional resistance, and/or different resistance levels.

The knee joint is a uni-axial hinge joint. The knee moves in a flexion (bending of the knee) and extension (straightening of the knee) direction. The three major bones that form the knee joint are: the femur (thigh bone), the tibia (shin bone), and the patella (kneecap). The prime muscle movers of the knee joint are the quadriceps muscles (on top of the femur), which move the knee into extension; and the hamstring muscles (underneath the femur), which move the knee into flexion. The quadriceps muscles are made up of five muscles known as the rectus femoris, vastus lateralis, vastus medialis, vastus intermedius and a secondary muscle, the vastus medialis oblique (VMO). The hamstring is made up of three muscles known as the biceps femoris, semimembranosus, and semitendinosus. The hamstring to quadriceps muscle strength ratio is two-thirds; meaning, the hamstring is normally approximately thirty-three percent weaker than the quadriceps. The muscles, ligaments, nervous system, and skeletal system work in unison to stabilize the knee during gait activities (walking, running, jumping).

In the example of a device to apply a load under motion across the knee, configured to train quadriceps, the device imposes resistance to extension of the lower leg at the knee joint and throughout the angular range of motion for the knee. During flexion (movement in the return direction) the device may be passive without providing any resistance to movement. Alternatively, in a bidirectional device, the device imposes resistance throughout both extension and flexion in this example to train both the quadriceps and the hamstring muscles. The resistance to flexion and extension may be equal, or may be dissimilar, depending upon the objective of the exercise.

The devices in accordance with the present invention may be provided with a user adjustable load or resistance, or modularity such that a resistance module having a first level of resistance can be removed and replaced by a second module having a second, different level of resistance.

In one implementation of the invention, the device provides passive resistance to motion throughout an angular range. At any stationary point within the range, the device imposes no bias. Rather the device merely resists movement in either one or both of flexion and extension. In contrast, an elastic resistance device imparts bias at any time it is deflected from neutral, whether moving or at a stop, and in only one direction.

In one mode of operation, the device is worn over an extended period of time wherein the activities of the wearer are dominantly aerobic as distinguished from anaerobic (i.e. dominantly non-anaerobic). The invention may be practiced where some of the activities are of an anaerobic nature, depending upon the training objective of the wearer. The extended period of time could be as short as one hour or less but is preferably at least two hours and sometimes at least eight hours, although it could also be at least about four hours or six hours or more. That may include at least about 1,500 or 2,000 step cycles or 5,000 step cycles or more.

The present invention is intended primarily for use to build tone or strength under conditions which favor aerobic metabolism, which will as a necessary consequence be accompanied by an elevated consumption of body fat. Thus the present invention may also comprise methods of achieving weight loss, by wearing one or two or more passive resistance devices for an extended period of time (disclosed elsewhere herein) each day for at least two or three or four or five or more days per week. The present invention also contemplates methods of reducing percent body fat via the same method steps.

Yet other embodiments of the present invention include biometric sensors and electronic data storage and/or wireless data export capabilities to a remote receiver such as a smartphone, activity logger, or other wireless device. In some embodiments, the sensors detect electrical signals which are related to the load being transmitted by the force modifying apparatus (e.g., force sensors, electromyography, etc.), the angular position of the upper leg attachment relative to the lower leg attachment, and/or the angular velocity of the upper leg attachment relative to the lower leg attachment, step cycles, range of motion, temperature, pulse or other data of interest.

The angular range of motion permitted by the dynamic joint 54 may be at least about 145°, or at least about 180° or more for the hip. Typically, a working angular range of motion for a hip device will be plus or minus about 45 or 55° from standing straight up, for normal walking activities, although flexion at the hip through an angle of at least about 90 degrees is necessary to enable sitting. A larger total range of at least about 180 degrees or 200 degrees or more may be desirable to enable stretching or other larger range activities. The dynamic joint at the knee preferably allows flexion of at least about 90 degrees, and preferably at least about 120 degrees or 140 degrees or more. Some of the dampers disclosed herein have a range of essentially 360 degrees or more, although that range is unnecessary for most of the constructs disclosed herein.

A bi-directional exercise device provides resistance to movement in both the flexion and extension directions. However, the level of resistance may differ. For example, in a normal knee, the ratio of the natural strength of a hamstring to a quadricep is roughly 1:3. A balanced passive resistance device may therefore impose 1 lb. of resistance on flexion for every 3 lbs. of resistance on extension. However, for certain athletic competitions or other objectives, the wearer may desire to alter the basic strength ratio of the unexercised hamstring to quadricep. So for example, the passive exercise device 20 may be provided with a ratio of a 2 lb. resistance on flexion for every 3 lb. resistance on extension or other ratio as may be desired depending upon the intended result.

In any of the embodiments disclosed herein, whether mechanical braces, fabric garments or hybrids, the resistance to movement will be relatively low compared to conventional weight training in view of the intended use of the apparatus for hours at a time. Anaerobic metabolism may be elevated by repetitively placing a minor load on routine movement over an extended period. The load will generally be higher than loads placed by normal clothing and technical wear, and preselected to work particular muscle groups. Preferably, the resistance elements may be adjusted or interchanged with other elements having a different resistance, or additive so that adding multiple resistance elements can increase the net resistance in a particular resistance zone.

The specific levels of resistance will vary depending upon the targeted muscle group, and typically also between flexion and extension across the same muscle group. Also wearer to wearer customization can be accomplished, to accommodate different training objectives. In general, resistances of at least about 0.5, and often at least about 1 or 2 or 3 or more foot-pounds will be used in strength building applications on both flexion and extension. Devices specifically configured for rehabilitation following injury (traumatic injury or surgical procedure) may have lower threshold values as desired.

The resistance to extension might be at least about 130%, sometimes at least about 150% and in some embodiments at least about 200% of the resistance to the corresponding flexion.

Toning garments intended for long term wear may have lower resistance, with extension normally equal to or greater than flexion. Torque provided by a resistance element intended for the hip for toning garments may be at least about 1 in-lbs, sometimes at least about 2 or 3 or 5 or more in-lbs. depending upon the desired result, measured on a dynamometer at 30 RPM at STP ambient conditions. Torque will typically be less than about 12 in-lbs., and often less than about 12 or 8 in-lbs. In some implementations, torque will be within the range of from about 1-4 in-lbs for a 'light' toning element; within the range of from about 3-6 in-lbs for a 'medium' toning element; and within the range of from about 5-10 in-lbs for a 'heavy' toning element. Dampers which are not capable of complete rotation may need to be measured by evaluating torque during reciprocal (pendulum) motion and converted to a full RPM equivalent.

The resistance garment may impart any of a variety of resistance profiles, as a function of angular displacement of the joint. For example, FIG. 1 schematically and qualitatively illustrates the units such as foot pounds (easily expressed as inch pounds or various other conventions known in the art) of resistance to movement in either or both an extension or flexion direction, as a function of the angular deviation of the joint at a constant speed across a dynamic motion range. In this illustration, an angle of zero may represent a joint such as a knee in a "start" or straight or other reference configuration, while the midpoint of the range of motion is half way through the range of motion of the target join or motion segment to the forward or rearward limit. Standing straight up, the femur can be considered to be at approximately half way through its anterior-posterior plane range of motion. The maximum range of motion is the maximum normal range for the target joint.

Referring to plot 60, there is illustrated an example in which the resistance to movement is constant throughout the angular range of motion, as a function of angle. Thus, at whatever point the distal extremity may be throughout the angular range of motion with respect to the proximal anatomy, incremental motion encounters the same resistance as it would at any other point throughout the angular range of motion (measured at the same speed in the case of certain dampers). The resistance provided is thus not a function of angular displacement. In some implementations, the resistance may be a function of angular velocity. But if motion stops, the resistance stops and there is no net bias or force applied by the device against the distal extremity unless an elastic element is also added to the garment.

Alternatively, referring to plot 62, there is illustrated the force curve relating to a dynamic joint in the garment in which the resistance to motion is greatest at the beginning of deviation from a starting point, and the resistance to motion falls off to a minimum as the distal extremity reaches the limit of its angular range.

Referring to plot 64, the garment imposes the least resistance at the beginning of bending the limb from the starting point, and the force opposing motion increases as a function of angular deviation throughout the range of motion. This may be utilized, for example, to emphasize building strength on the back half or back portion of an angular range of motion.

As a further alternative, referring to plot 66, the garment may be configured to produce the most strength at the end points of the range of motion, while deemphasizing a central portion of the range of motion. Although not illustrated, the inverse of the plot 66 may additionally be provided, such that the end points in either direction of the angular range of motion across a joint are deemphasized, and strength throughout the middle portion of the range of motion is emphasized.

As will be apparent to those of skill in the art, any of a variety of resistance profiles may be readily constructed, depending upon the desired objective of the training for a particular athlete or rehabilitation protocol. In some implementations (e.g., viscous rotary dampers) the resistance varies as a function of velocity, so that the faster the wearer seeks to move through a given range of motion, the proportionally higher the responsive resistance. Resistance remains constant in response to constant velocity motion. This performance profile in essence allows the wearer to customize the resistance level, in response to effort, and may be desirable in the medical rehabilitation markets as well as the related markets of toning and training.

Figure 2:
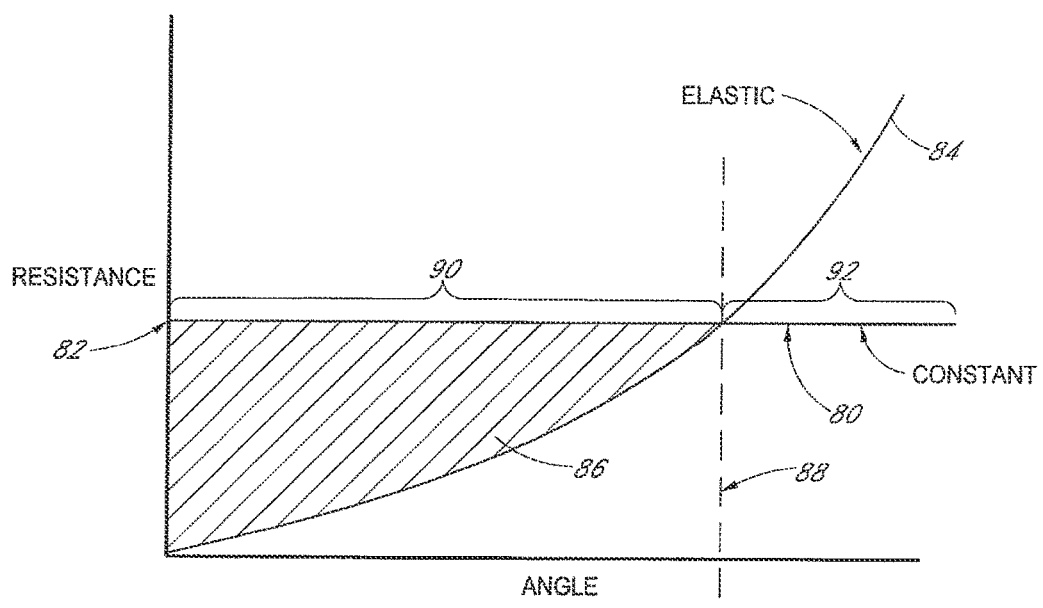
FIG. 2 illustrates a comparison in muscle loading throughout an angular range for a constant resistance device and an elastic resistance device.

Referring to FIG. 2, there is illustrated a qualitative relationship between a constant and an elastic resistive force, throughout a range of (constant velocity in the case of a rotary damper) motion. The constant force line 80 remains essentially unchanged as a function of angular displacement from any starting point. So the work required to move in opposition to the resistance is at its predetermined value 82 starting at the beginning of any movement within the range, throughout both an early cycle 90 and a late cycle 92.

In contrast, extension (or flexion) throughout an angular range against an elastic resistive force encounters a variable resistance which starts low and increases as a function of the angle of displacement. This elastic resistive force is represented by line 84. Throughout an early cycle 90, resistance may be less than the predetermined value 82 until the elastic has been sufficiently loaded that the elastic resistance curve 84 crosses the predetermined value 82 of the constant resistance line 80 at a transition 88. Only angular displacement within the late cycle 92 encounters resistance at or above the predetermined value 82.

The angle zero can be any reference point throughout the walking cycle, such as standing straight up, or with the leg at the most posterior part of the stride, wherever the elastic has been designed to provide neutral (zero) bias. The shaded area 86 represents work that would be accomplished under the constant resistance device, but would not be accomplished during the early cycle 90 for the elastic device as the elastic is loading and resistance is climbing. Thus the constant resistance device forces work throughout the angular range, while never exceeding a predetermined maximum resistance force, but the elastic may provide inadequate resistance throughout the early cycle 90. This is important because strength is best developed throughout the range of motion that is actually exercised under load, so elastic mechanisms may inadequately load the muscles in the early cycle 90. The shaded area 86 thus represents the inefficiency in an elastic resistance system compared to a constant resistance system.

Early cycle loading in an elastic model can be elevated by pre-tensioning the elastic so that at angle zero the resistance is already up to the reference value 82. But the device now has lost its neutral bias resting position and at all angles throughout the cycle the wearer will be fighting a bias which may be undesirable. In addition, pre-tensioning the elastic will also elevate resistance throughout the late cycle 92 potentially above what the wearer can tolerate or at least sufficiently that the wearer will simply shorten their stride or make other accommodations to avoid the resistance spike. Thus maintaining resistance within a range of at least a threshold minimum and a maximum throughout the angular range of motion is preferred. The maximum will generally be less than about 3×, generally less than about 2× the minimum, and in different settings no more than about 80%, 50%, 25%, 10% or 5% or 2% greater than the minimum. In general, substantially constant resistance means plus or minus no more than about 10% from the average resistance throughout the working range.

Figure 3:
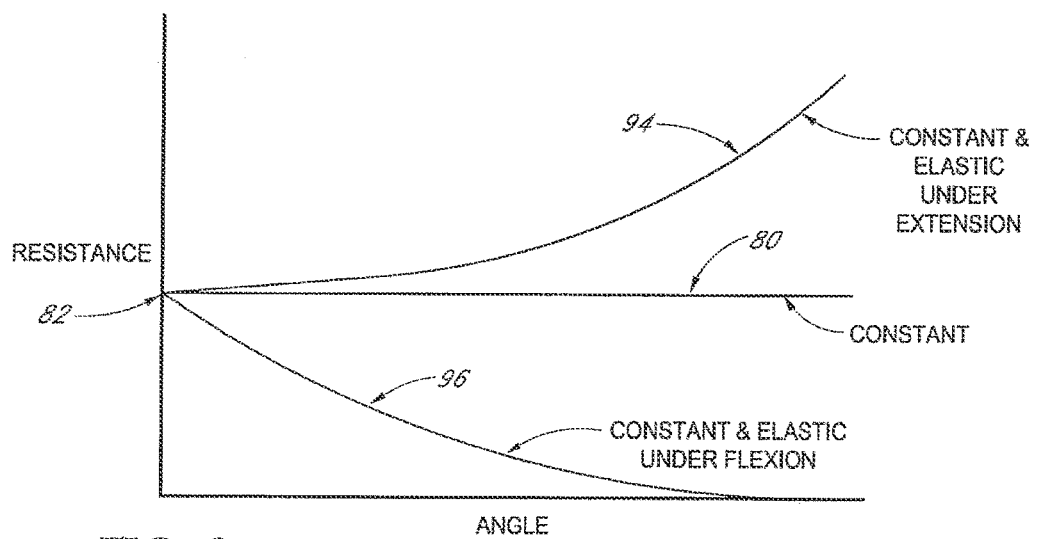
FIG. 3 illustrates a comparison in muscle loading throughout an angular range for a hybrid resistance device having a constant resistance component and an elastic resistance component.

Referring to FIG. 3, the performance of a hybrid garment is illustrated, in which both a passive resistance component and an elastic component are present so that the wearer experiences a force profile that is the sum of the passive and elastic components. This might be accomplished by securing one or more springs such as leaf springs, coil springs or other spring elements (spring wire such as stainless steel, NiTinol or other elastic metals, rubber bands or other elastic polymers or fabrics known in the art) in parallel with the passive resistive element. Bending across the joint is thus opposed by the passive resistance component as well as resisted or supported by the spring or elastic component depending upon the orientation of the elastic component relative to the flexion or extension direction.

Thus the net force curve on, for example, extension is illustrated as 94 and represents the sum of the resistance from the passive and elastic components assuming the elastic component is configured to be fully relaxed at the reference angle zero. However, under flexion, the elastic component assists flexion in opposition to the resistance from the passive component, producing a curve more like 96 in which resistance to flexion climbs as the angular deviation returns to the reference point. Hybrid elastic/passive configurations can be used where a different resistance profile is desired for flexion compared to extension across a particular motion segment.

In any of the foregoing embodiments, it may be desirable to provide a release which disengages the resistance to movement upon an abrupt increase in force from the wearer. The release may be in the form of a releasable detent or interference joint which can be opened by elastic deformation under force above a preset threshold which is set above normally anticipated forces in normal use. If a wearer should stumble, the reflexive movement to regain balance will activate the release and eliminate resistance to further movement, as a safety feature.

At least a right and a left safety release may be provided, to release the resistance from the right and left resistance elements in response to a sudden spike in force applied by the wearer such as might occur if the wearer were to try to recover from missing a step or tripping. The release may be configured in a variety of ways depending upon the underlying device design. For example, in a solid flexible rod resistance element, a short section of rod may be constructed of a different material which would snap under a sudden load spike. That resistance element would be disposed and replaced once the release has been actuated. Alternatively, a male component on a first section of the resistance element can be snap fit with a female component on a second section of the resistance element, such that the two components become reversibly disengaged from each other upon application of a sudden force above the predetermined safety threshold. Two components can be pivotable connected to each other along the length of the resistance element, but with a coefficient of static friction such that movement of the pivot is only permitted in response to loads above the predetermined threshold. Alternatively, one or more of the belt connectors or corresponding inferior connectors can be releasably secured with respect to the wearer. Any of a variety of interference fit attachment structures or hook and loop fasteners can be optimized to reversibly release upon application of the threshold pressure. In more complex systems or systems configured for relatively high resistance such as for heavy athletic training, more sophisticated release mechanisms may be configured such as those used in conventional ski bindings and well understood in the art.

Figures 4, 5:
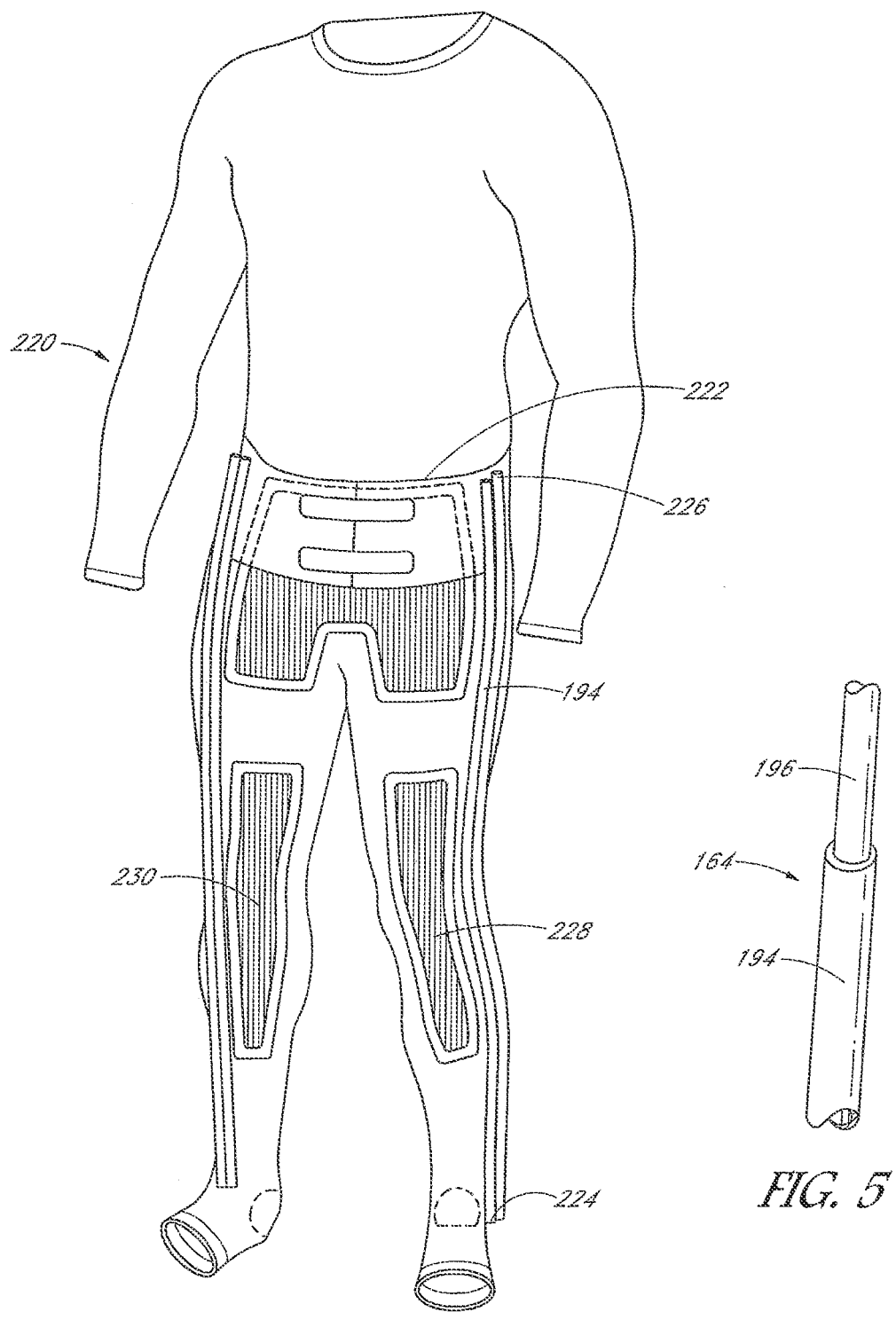
FIG. 4 is a front elevational view of a garment incorporating resistance features in accordance with the present invention.
FIG. 5 is a partial elevational view of a resistance element in accordance with the present invention.

Referring to FIG. 4, there is illustrated a front elevational view of a garment in the form of a pant or full body suit 220, incorporating resistance elements in accordance with the present invention. Although illustrated as a full body suit, the garment may be in the form of pants or shorts alone, from the waist down, or an upper body garment similar to a shirt. In general, the body suit is provided with one or more resistance elements spanning a joint of interest, as has been discussed herein. The resistance element may be any of the devices disclosed elsewhere herein, either removably or permanently attached to the fabric of the garment. For example, in the illustrated embodiment, a plurality of sleeves 194 extend distally from the waist 222 down to the ankle 224 for permanently or removably receiving corresponding resistance elements therein.

Preferably, the resistance elements may be removably carried by the garment, such as via an opening 226 illustrated at the superior end of sleeve 194, thereby enabling customization of the resistance level by the wearer. One example is shown in FIG. 5A, in which a segmented or malleable metal rod 196 os removably positioned within sleeve 194. In addition, the resistance elements may preferably be removed for laundering the garment, and for taking the garment on and off. The garment can more easily be positioned on the body without the resistance elements, and the resistance elements may be introduced into the sleeve 194 or other receiving structure thereafter.

In addition, or as an alternative to the resistance elements disclosed previously herein, the garment may be provided with one or more elastic panels positioned and oriented to resist movement in a preselected direction. For example, an elastic panel having an axis of elongation in the inferior superior direction, and positioned behind the knee, can provide resistance to extension of the knee. Alternatively, a stretch panel on the front or anterior surface of the leg, spanning the knee, can bias the knee in the direction of extension and resist flexion. Panels 228 and 230 illustrated in FIG. 4 can be configured to stretch upon flexion of the knee thereby biasing the garment in the direction of extension. Resistance to flexion or extension or other movement of any other joint or motion segment in the body can be provided, by orienting one or more stretch panels of fabric in a similar fashion. In a passive resistance garment, the panels may comprise a plurality of wires or strands attached to or woven or braided into the fabric, as discussed below.

Any of a variety of fabrics may be utilized to form the garment, preferably materials which are highly breathable thereby allowing heat and moisture to escape, and having sufficient structural integrity to transfer force between the body and the resistance elements. The fabric can be compression or other elastic fabric, or an inelastic material with elastic panels in position to load specific muscle groups, or metal or metal-nonmetal hybrids depending upon the desired performance.

Three functionally distinct fabrics are discussed below. In one, the fabric is the resistance element. This fabric may include strands of a malleable material such as a metal or polymer, which resist bending. The resistive fabric will be oriented such that the malleable strands extend across the motion segment such that motion of the body at the segment will bend the malleable strands. A second type of fabric described herein may be utilized for constructing the underlying garment. A third type of fabric may be a force transfer fabric, such as for transferring or dissipating force from a lever arm to a relatively more highly stretchable fabric such as the base fabric for a compression pant. Selection of particular weaves, polymers, or other variables discussed below can be accomplished by those of skill in the art, taking into account the role that the fabric will play in the finished garment.

The woven resistance fabric of the present invention may comprise any of a variety of weaves typically between at least a first support filament and at least a second resistance filament. For example, the resistance fabric may comprise weaves such as plain weaves, basket weaves, rep or rib weaves, twill weaves (e.g., straight twill, reverse twill, herringbone twill), satin weaves, and double weaves (e.g., double-width, tubular double weave, reversed double weave). In general, the weave is a convenient structure for supporting a plurality of resistance imparting strands in a manner that can be made into or supported by a garment like structure that can be carried by a wearer's body. Nonwoven constructs can also be utilized, such as by securing a plurality of nonwoven (e.g., parallel) resistance strands (e.g., metal wire strands) to each other or to a supporting fabric base. Securing may be accomplished by dip coating, spray coating or otherwise coating or embedding the resistance strands with a flexible adhesive or other polymer, or weaving or braiding, to produce a flexible resistance band or sheet.

The term "strand" as used herein is a generic term for an elongate, thin flexible element suitable for weaving. For example, strands may include, but are not limited to monofilaments, filaments twisted together, fibers spun together or otherwise joined, yarns, roving yarns, crepe yarns, ply yarns, cord yarns, threads, strings, filaments laid together without twist, single strand or multi strand wire as well as other configurations. Strand includes elements sometimes referred to herein as rods, such that for example a 0.125 inch diameter copper rod is a relatively thick strand. Strand diameters will generally be at least about 0.018 inches, at least about 0.025 inches at least about 0.040 inches, at least about 0.050 inches or at least about 0.10 inches or more, depending upon the construction and desired performance. For strands that are not circular in cross sections, the foregoing values can readily be converted to cross sectional areas as is understood in the art. Unless otherwise specified, references herein to strand diameters or cross sectional areas along the length of a strand or of a group of strands refers to an average value for the corresponding diameters or cross sectional areas.

A woven resistance fabric embodiment generally comprise at least a first and second sets of relatively straight strands, the warp and the weft, which cross and interweave to form a fabric. Typically, the warp and weft yarn cross at approximately a right angle as woven, but may cross at any angle such as at least about 45, 65, 75 or 85 degrees. Also typically, fabric is woven to have a given width, but may have any desired length. The warp yarn runs in the length direction of the fabric, which is generally the longer dimension thereof, and the weft yarn runs in the crosswise or width direction thereof, which is generally the shorter dimension. It may be convenient to weave passive resistance fabric such that the warp strand is a metal such as copper and the weft is a conventional athletic fabric material. The pants or body suit or resistance strips would be cut with the long axis of the resistance strands primarily running in an inferior-superior direction in the example of a pant, and the non-resistance strands run in a circumferential direction relative to the leg. A textile and/or fabric may be woven in a single-layer weave and/or in a plural-layer weave. It is noted that textiles and/or fabrics having two or more layers, i.e. plural layers, are commonly and generally referred to as multilayer weaves. Certain weaves may be referred to specifically, e.g., a two-layer woven fabric may be referred to as a double weave. For example, an inner liner may be provided for comfort, to separate the wearer from the resistance layer.

In one embodiment of the present invention, a first warp or weft fibers may be aesthetic fibers that are selected for their aesthetic appeal (e.g., color, texture, ability to receive dye, drapeability, etc.). Examples of such fibers may include natural fibers, cotton, wool, rayon, polyamid fibers, modeacrylic fibers, high modulus fibers, Kevlar® fibers, Nomex® fibers, and other fibers formulated to produce or exhibit aesthetic characteristics.

A second warp or weft fibers may be performance fibers that are selected for their strength or protective properties (e.g., cut, abrasion, ballistic, and/or fire resistance characteristics, etc.). Examples of performance fibers include high molecular weight polyethylene, aramid, carbon fiber, Kevlar® fibers, Nomex® fibers, fiberglass, and other fibers formulated to produce or exhibit performance characteristics. Many performance fibers are not aesthetically desirable (e.g., don't receive dyes or colors well, etc.); however, by structuring a fabric in accordance with various embodiments of the present invention, traditional aesthetic problems associated with such fibers may have a significantly reduced effect given that such fibers are generally hidden from view.

A third warp or weft fibers may be comfort fibers that are selected for their comfort-providing qualities (e.g., softness against a wearer's skin, cooling properties, etc.). Examples of comfort fibers include cellulosic fibers such as cotton, rayon, wool, microfiber polyester, nylon, and other fibers formulated to produce or exhibit comfort characteristics.

In addition, the fibers that will extend around the leg and transverse to the metal fibers may be stretchable fibers that are selected to provide flexibility to the fabric to allow the fabric to have a better fit on the wearer and to allow the wearer more unrestricted movement while wearing the fabric. Examples of stretchable fibers include Lycra® fibers, Spandex® fibers, composite fibers that include Lycra® or Spandex® fibers, Kevlar® fibers, high modulus polyethylene, wool, rayon, nylon, modeacrylic fibers, and other fibers formulated to exhibit stretch characteristics.

Materials used for the shape memory element strands need only be biocompatible or able to be made biocompatible. Suitable materials for the shape memory element strands include shape memory metals and shape memory polymers. Suitable shape memory metals include, for example, TiNi (Nitinol), CuZnAl, and FeNiAl alloys. Particularly preferred are "superelastic" metal alloys. Superelasticity refers to a shape memory metal alloy's ability to spring back to its austenitic form from a stress-induced martensite at temperatures above austenite finish temperature. The austenite finish temperature refers to the temperature at which the transformation of a shape memory metal from the martensitic phase to the austenitic phase completes.

For example, martensite in a Nitinol alloy may be stress induced if stress is applied at a temperature above the Nitinol alloy's austenite start temperature. Since austenite is the stable phase at temperatures above austenite finish temperature under no-load conditions, the material springs back to its original shape when the stress is removed. This extraordinary elasticity is called superelasticity. In one example, Nitinol wire may be in the superelastic condition where the wire has been cold worked at least 40% and given an aging heat treatment at approximately 500 degrees Celsius for at least 10 minutes. The Nitinol wire is in its fully superelastic condition where the use temperature is greater than the austenite finish temperature of the Nitinol wire.

The term "elastic" is used to describe any component that is capable of substantial elastic deformation, which results in a bias to return to its non-deformed or neutral state. It should be understood that the term "elastic" includes but is not intended to be limited to a particular class of elastic materials. In some cases, one or more elastic portions can be made of an elastomeric material including, but not limited to: natural rubber, synthetic polyisoprene, butyl rubber, halogenated butyl rubbers, polybutadiene, styrene-butadiene rubber, nitrile rubber, hydrogenated nitrile rubbers, chloroprene rubber (such as polychloroprene, neoprene and bayprene), ethylene propylene rubber (EPM), ethylene propylene diene rubber (EPDM), epichlorohydrin rubber (ECO), polyacrylic rubber, silicone rubber, fluorosilicone rubber (FVMQ), fluoroelastomers (such as Viton, Tecnoflon, Fluorel, Aflas and Dai-EI), perfluoroelastomers (such as Tecnoflon PFR, Kalrez, Chemraz, Perlast), polyether block amides (PEBA), chlorosulfonated polyethylene (CSM), ethylene-vinyl acetate (EVA), various types of thermoplastic elastomers (TPE), for example Elastron, as well as any other type of material with substantial elastic properties. In other cases, an elastic portion could be made of another type of material that is capable of elastic deformation or composite weaves of elastic and inelastic fibers or threads. In one exemplary embodiment, each elastic portion may include neoprene potentially augmented by a secondary elastic component such as sheets or strips of a latex or other rubber depending upon the desired elastic force and dynamic range of stretch.

Another fabric with a high modulus of elasticity is elastane, which is known in the art of compression fabrics and may be used for construction of the underlying garment. The material may be a polyester/elastane fabric with moisture-wicking properties. For example, the fabric may comprise 5 oz/yd.sup.2 micro-denier polyester/elastane warp knit tricot fabric that will wick moisture from the body and include 76% 40 denier dull polyester and 24% 55 denier spandex knit. The high elastane content allows for proper stretch and support. The fabric may be a tricot construction at a 60" width. The mean warp stretch may be 187% at 10 lbs of load, and the mean width stretch may be 90% at 10 lbs of load. This fabric also may have a wicking finish applied to it. Such a fabric is available from UNDER ARMOUR™ Although the foregoing fabric is given as an example, it will be appreciated that any of a variety of other fabric or other materials known in the art may be used to construct the garment 100, including compression fabrics and non-compression fabrics. Examples of such fabrics include, but are not limited to, knit, woven and non-woven fabrics comprised of nylon, polyester, cotton, elastane, any of the materials identified above and blends thereof. Any of the foregoing can be augmented with mechanical resistance elements, such as bendable rods, springs and others disclosed herein.

The resistance fabric can be characterized by the total cross sectional area of metal per unit length of fabric, measured transverse to the direction of the metal strands. For example, a plain weave having parallel metal strands each having a diameter of 0.020 inches, each adjacent strands separated by 0.020 inches, will have a metal density of 25 strands per inch. The sum of the cross sections of the 25 strands is approximately 0.008 square inches.

The optimal metal density will depend upon garment design, such as whether the entire circumference of a leg is surrounded by hybrid fabric, or only discrete panels will include the hybrid fiber, the presence of any supplemental resistance elements, and the desired resistance provided by a given motion segment on the garment. In general, the metal density will be at least about 0.010 square inches of metal per running inch of fabric, and may be at least about 0.020, at least about 0.030 and in some implementations at least about 0.040 square inches of metal per inch. Most fabrics will have within the range of from about 0.020 and about 0.060 square inches of metal per inch of fabric, and often within the range of from about 0.025 and about 0.045 square inches per inch of fabric.

Figures 6A, 6B:
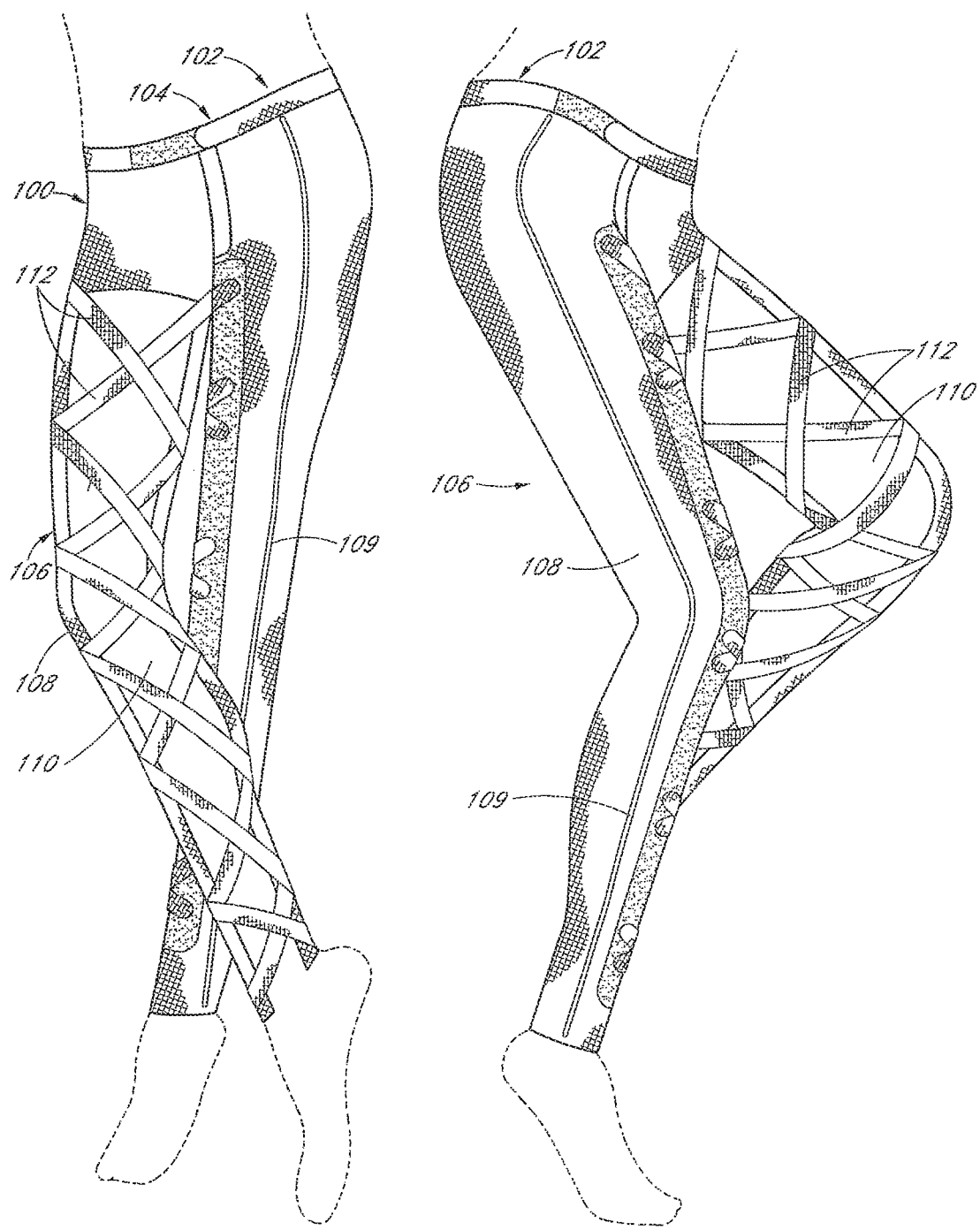
FIGS. 6A and 6B are perspective views of an alternative resistance garment in accordance with the present invention.

Referring to FIGS. 6A and 6B, there is illustrated a side opening pant embodiment of the present invention which can support either resistance fabric, resistance rods or both types of resistance element, or a rotary resistance unit as discussed elsewhere herein. The pant 100 comprises a waist 102 which may be opened or closed or tightened by a fastener 104. Fastener 104 may be any of a variety of preferably low profile and comfortable adjustable fasteners such as Velcro or a belt buckle.

A right leg 106 comprises a lateral resistance panel 108 and a medial side opening 110. The resistance panel runs from the waist to the ankle and may be made from or support a resistance fabric and or resistance strands. The resistance panel may have an average width measured in the circumferential direction around the leg of no more than about 2", sometimes no more than about 4" and often no more than about 6" or 8" so that it does not wrap all the way around the leg. Typically, the resistance panel will be oriented to run along the lateral side of the leg, although additional resistance panels may run along the medial side, the posterior or anterior or any one or combination of the foregoing, depending upon the desired performance.

The resistance panel may be constructed from a resistance fabric, or may have one or more panels of resistance fabric carried thereon, or carry a rotary damper or other resistance element disclosed herein. The resistance panels may also or alternatively be provided with at least one or two or three or four or more attachment structures or guides such as sleeve 109, for receiving a resistance element such as a malleable rod or damper lever arm or other resistance element disclosed elsewhere herein. The sleeve may have a closed inferior end and an open or openable superior end, to removably receive the resistance element therein, so that the wearer can customize the resistance level as desired such as by exchanging resistance elements.

In the illustrated embodiment, the right resistance panel 108 is securely held against the leg by a plurality of straps 112 which extend across the opening 110. Each strap has a first end which is preferably permanently secured to the resistance panel 108 or to a base garment in an embodiment having a removable resistance panel. A second end may be releasably secured to the garment or resistance panel such as by Velcro or other releasable fastener. The left and right legs of all embodiments herein are preferably bilaterally symmetrical.

The straps 112 preferably comprise a stretch fabric such as a weave with elastic fibers at least running in the longitudinal direction. One or two or three or more straps 112 may be provided both above and below the knee, to securely hold the resistance panel in place. Straps 112 may be oriented perpendicular to the long axis of the leg, or an angle as illustrated to provide a criss cross configuration.

Figure 7:
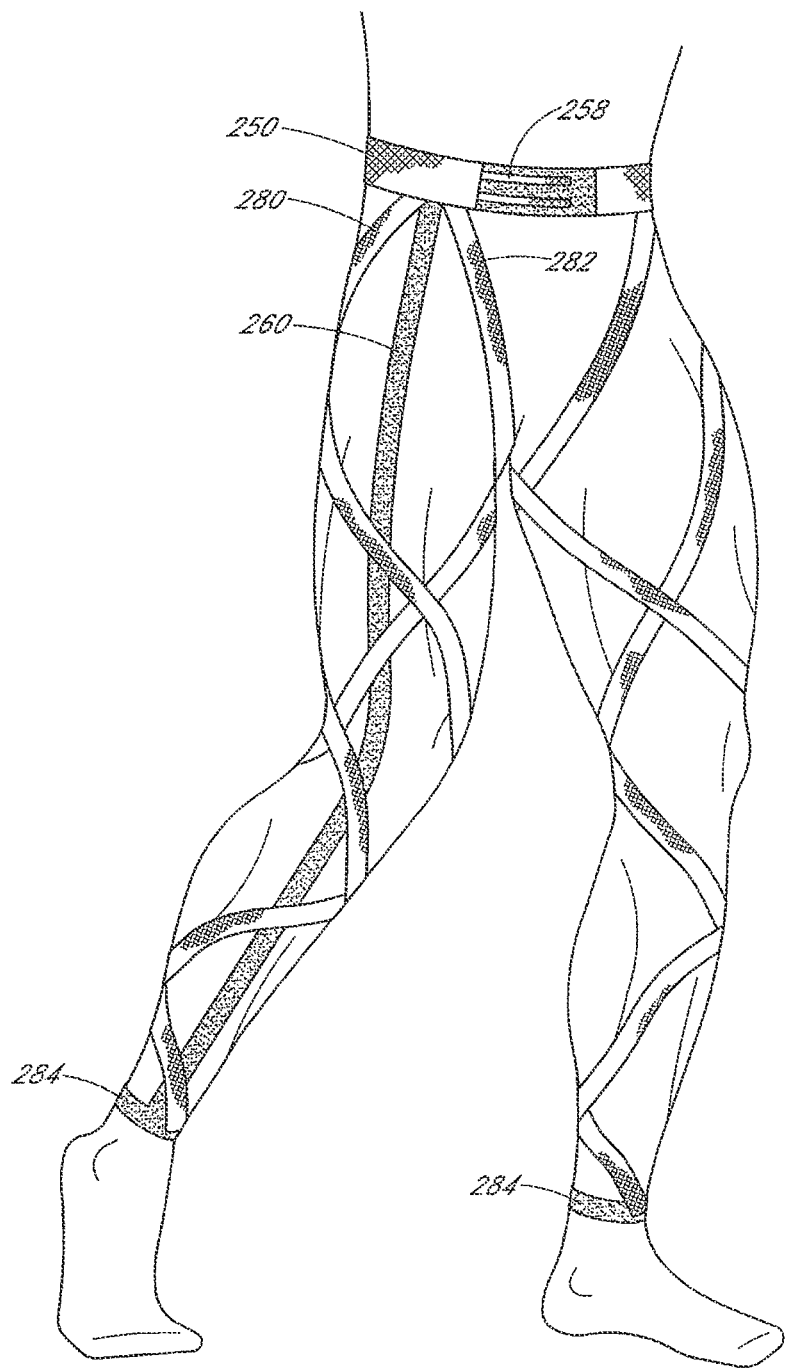
FIG. 7 is a perspective view of an alternative resistance garment in accordance with the present invention.
Figure 8:
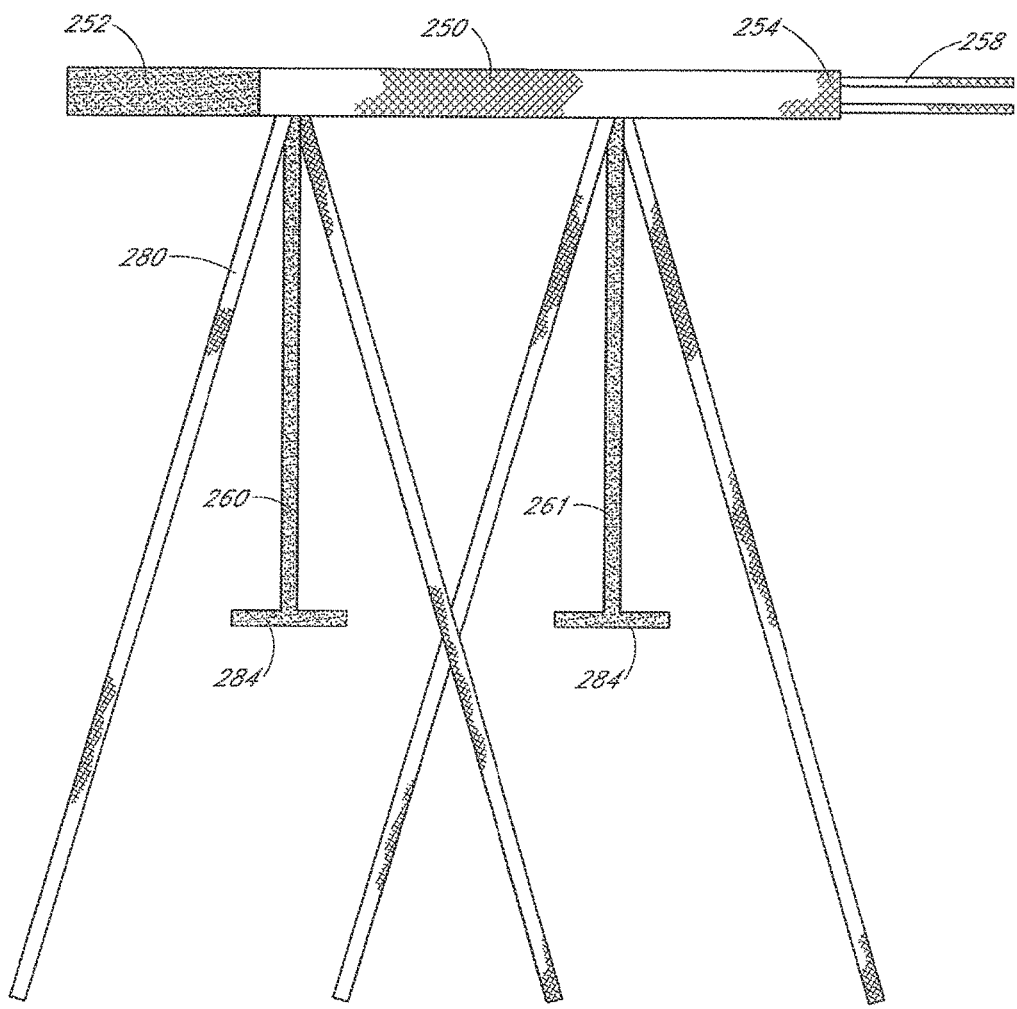
FIG. 8 is a flat plan view of the resistance garment of FIG. 7.

Referring to FIGS. 7 and 8, a resistance garment (or a structural subassembly that is attachable to a compression or other garment) is shown having a waist or belt 250 and left and right resistance panels 260 and 261. In this implementation, the resistance panels may have an average width of no more than about 8 inches, no more than about 6 inches, no more than about 4 inches, no more than about 2 inches, or no more than about 1 inch depending upon whether resistance is generated by a fabric or other resistance element.

The left resistance panel is associated with at least a first strap 280 and as illustrated also a second strap 282 which are secured to the waist and or the resistance panel 260. As shown in FIG. 7, the first strap is wrapped helically around the leg and secured to the ankle by attachment to itself, or to the left resistance panel 260 or to an ankle strap 284 that may be provided at the inferior end of the resistance panel 260. The second strap 282 may then be wrapped helically around the leg in the opposite direction and secured to the ankle. At each of the crossing points between the straps 280 and 282 and the resistance panel 260 complementary Velcro panels align and create attachment points. Preferably the straps comprise stretch fabric to hold the resistance panel snugly in place yet accommodate moving musculature. The garment can be shortened, so that the straps 284 are positioned above the knee in a pair of shorts or full length pants designed to only apply resistance at the hip.

Figure 9A:
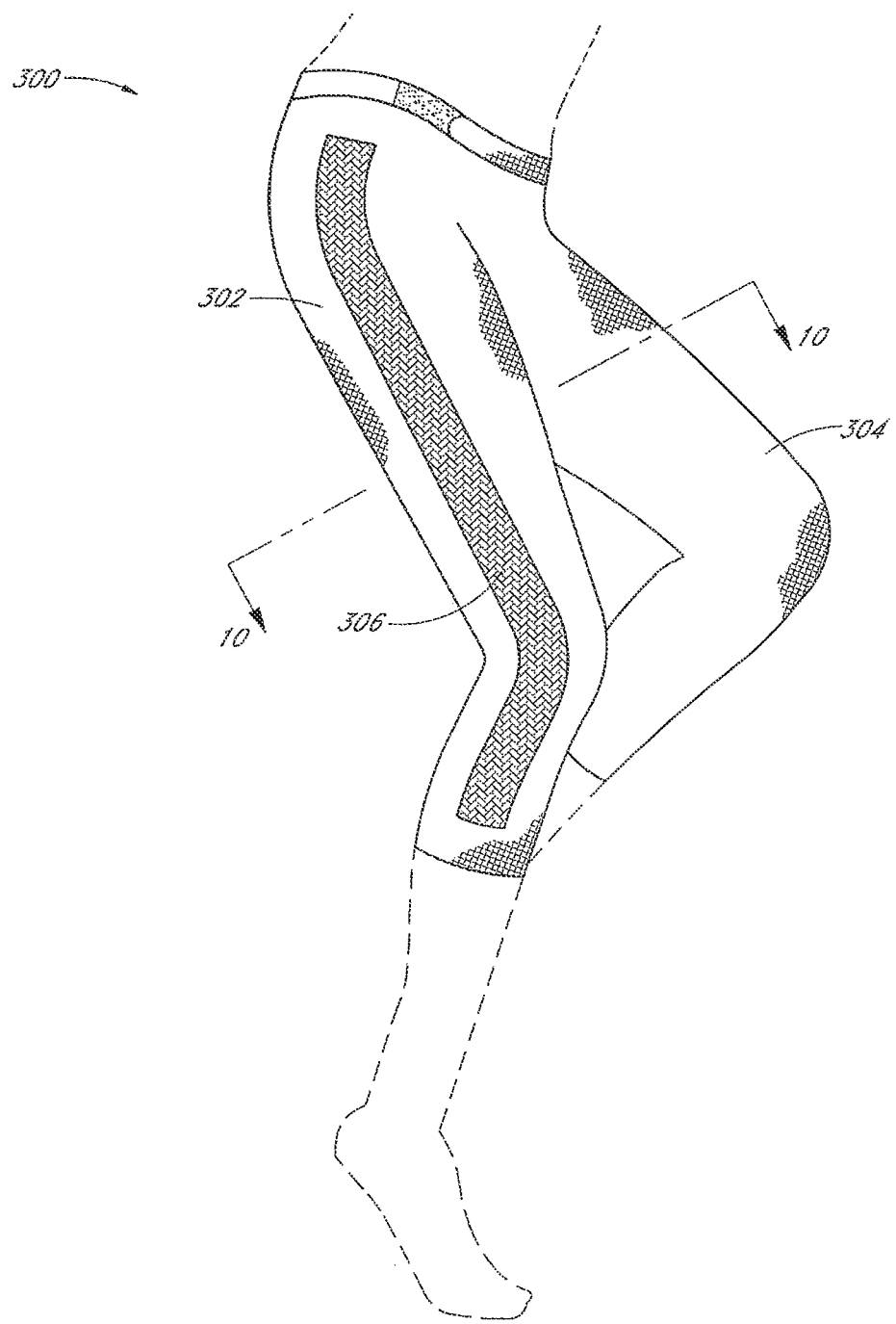
FIGS. 9A and 9B are side elevational views of detachable component toning garments, having a resistance element extending in the inferior-superior direction.
Figure 9B:
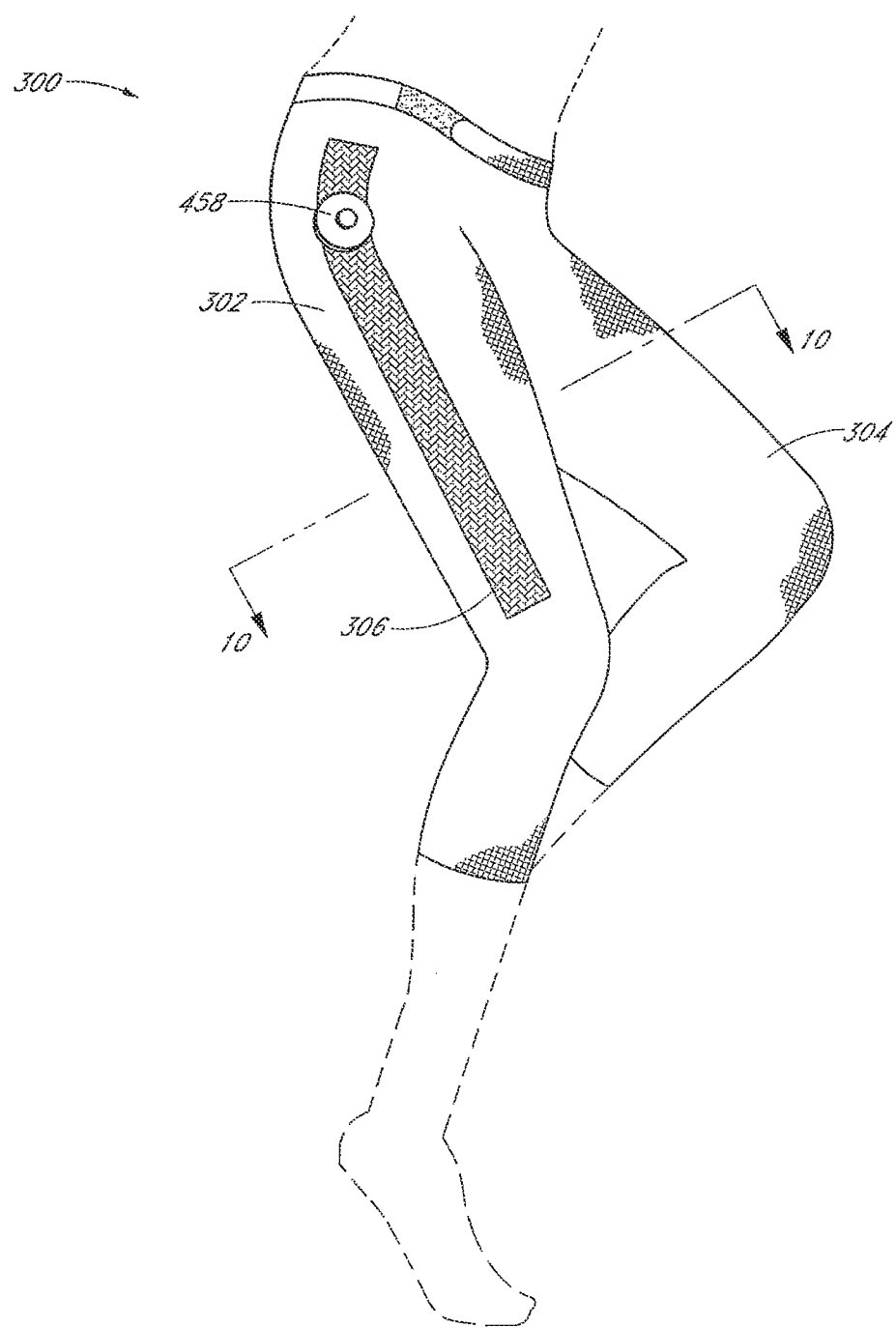

Referring to FIGS. 9A and 9B, there is illustrated a toning garment 300 having a right leg 302 and a left leg 304. At least one resistance elements 306 is provided on each of the left leg 304 and right leg 302. In the illustrated embodiment, a single resistance element 306 is provided on each of the right and left legs, extending in an inferior-superior orientation on a lateral side of the leg, and spanning both the hip and knee. Resistance elements 306 may be provided on the lateral sides, the medial sides, or the lateral and medial sides of the leg. In this orientation, the bending of the resistance elements 306 is primarily in the anterior-posterior plane (in shear for a flat resistance element 306). The resistance element may comprise a rotary device such as a rotary damper 458 (FIG. 9B) aligned with an axis of rotation of the desired joint.

Alternatively, resistance elements 306 may be provided on the anterior or posterior or both aspects of the garment 300. Normal anatomical motion at the hip and knee would cause anterior or posterior resistance elements 306 to bend out of plane, and also to accommodate axial elongation and compression during the normal walking cycle. Thus, internal construction of anterior or posterior surface resistance elements 306 may be different than that utilized on a lateral or medial orientation, the latter not necessarily needing to accommodate axial expansion or contraction except to the extent desirable to compensate for rotational axis misalignment, discussed below.

Figure 10:
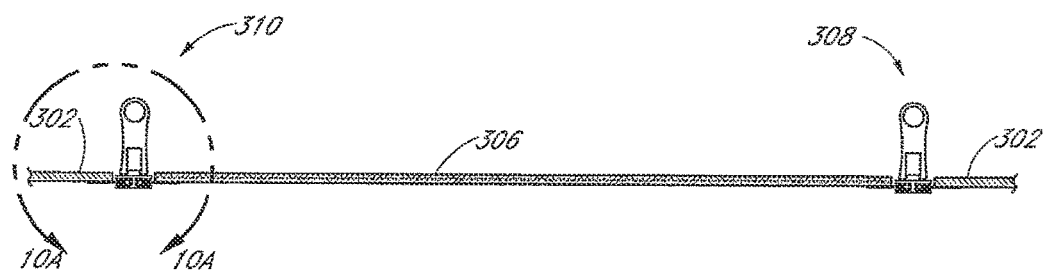
FIG. 10 is a cross-sectional view taken along the line 10-10 of FIGS. 9A and 9B, showing a removable resistance element secured to the garment.

Preferably, resistance elements 306 are removably secured to the garment 300. Referring to FIG. 10, removable attachment may be accomplished by providing a posterior attachment structure 308 secured to the right leg 302 and an anterior attachment structure 310 secured at an anterior orientation on the right leg 302. As with elsewhere herein, the devices of the present invention are preferably bilaterally symmetrical and only one side will generally be described in detail with the understanding that the other side will have a symmetrical configuration.

Figure 10A:
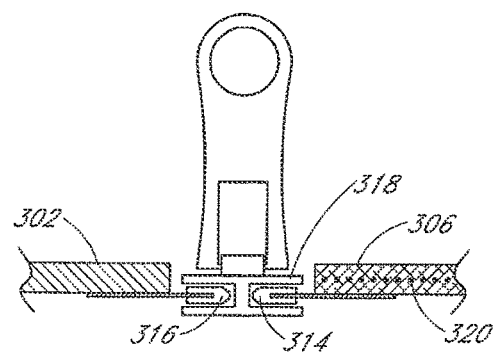
FIG. 10A is an enlarged view taken along the line 10A-10A of FIG. 10.

Each of the posterior attachment structure 308 and anterior attachment structure 310 are preferably attachment structures that permit secure attachment and removal of the resistance elements 306 to the garment 300. Referring to FIG. 10A, one exemplary attachment structure 308 is a zipper. A first plurality of teeth 314 may be secured along the length of the resistance elements 306 such as by stitching, adhesives, or other technique. First plurality of teeth 314 are configured to interdigitate or engage with a second plurality of teeth 316 secured along an edge which is attached to the toning garment 300. A slider 318 may be advanced up and down the inferior posterior direction, zipping and unzipping the resistance element 306 to the right leg 302.

Schematically illustrated in the resistance element 306 of FIG. 10A is a plurality of malleable strands 320, such as may be present in a wire fabric weave. However, any of the resistance elements described in the present application may be configured for interchangeable replacement with the resistance elements 306, such as variations of the pivotable resistance unit 458 discussed in connection with FIG. 13 and beyond. Thus, the user of the toning garment 300 may select a resistance element out of an array of resistance elements, and releasably secure the resistance elements 306 to the garment 300. After a period of time, the resistance elements 306 may be removed from the toning garment 300 and replaced by a resistance element 306 having a different resistance characteristic. Alternatively, the resistance elements 306 may be removed and replaced by a resistance element having an identical resistance characteristic, such as following the useful life of the first resistance element.

A plurality of interchangeable resistance elements having different structures can be provided, such as metal wire, metal weaves, segmented resistance elements, pivotable resistance elements, open cell or closed cell foam, elastomeric materials such as silicone, latex or various blends of rubber, resistance elements having pulleys and wires, can be configured having an interchangeable mounting system and dimensions so that they may be interchanged on a single toning garment 300.

Figure 11:
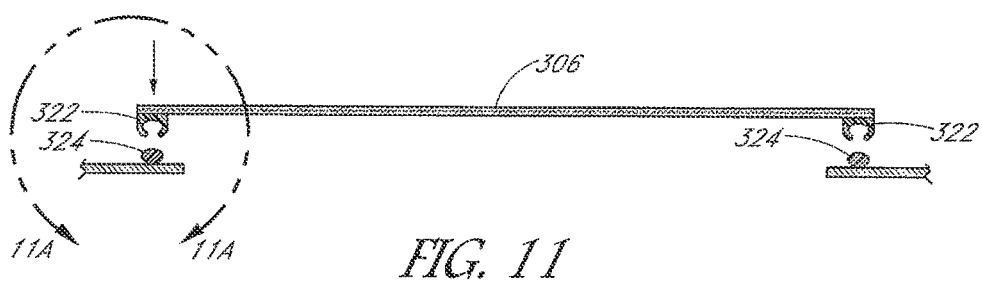
FIG. 11 is a cross-sectional view through a detachable component resistance element, showing an alternate attachment structure.
Figure 11A:
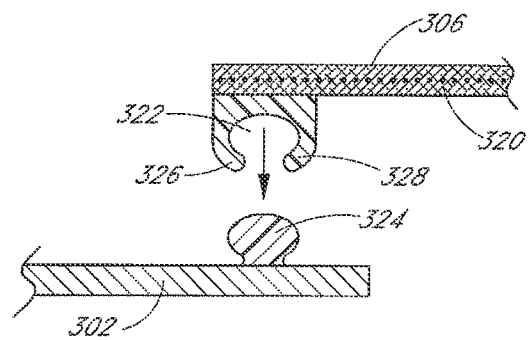
FIG. 11A is an enlarged view taken along the line 11A-11A in FIG. 11.

An alternative attachment structure comprises an elongate press fit attachment, that extends in the inferior superior axis, typically along the edges of the resistance elements 306. Referring to FIG. 11, one of the resistance elements 306 and corresponding locations on the garment 300 is provided with an elongate elastically deformable channel 322. The corresponding or complementary surface structure on the other of the resistance elements 306 or the garment 300 is an elongate bead 324. The elongate bead may be press fit into the elongate channel, like a zip lock fastener, to secure the resistance elements 306 in place. Press fitting the fastener to releasably retain the resistance elements 306 on the garment 300 may be accomplished by manual pressure, such as by running a finger along the length of the attachment structure.

Figure 12:
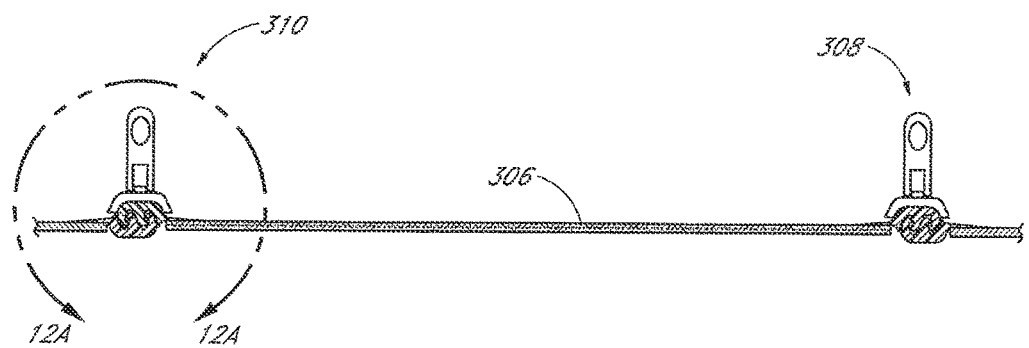
FIG. 12 is a cross-sectional view as in FIG. 10, showing an alternate attachment structure between the resistance element and the garment.
Figure 12A:
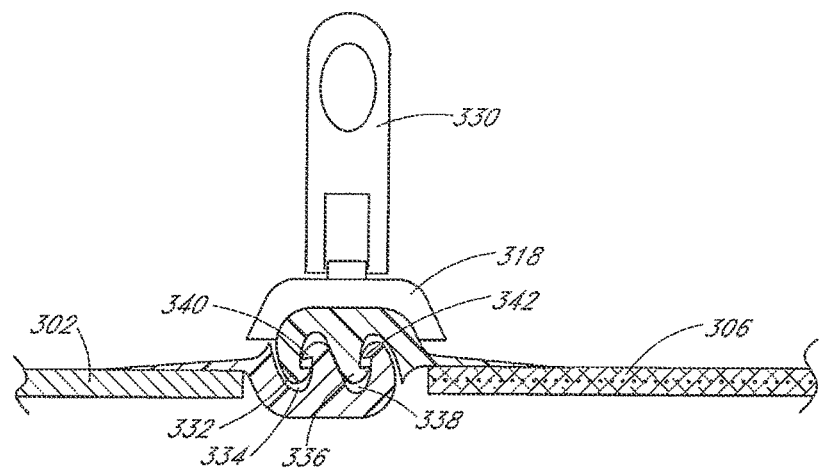
FIG. 12A is an enlarged view taken along the line 12A-12A in FIG. 12.

Alternatively, such as is illustrated in FIGS. 12 and 12A, a press fit embodiment may be secured and unsecured using a slider 318, typically having a pull tab 330. The implementation of the press fit fastener shown in FIGS. 12 and 12A provide a more robust connection between the resistance element 306 and garment 300. This may be desirable for implementations of the invention having relatively high resistance to movement, which will place greater tension on the attachment structure.

Referring to FIG. 12A, a first projection 332 attached directly or indirectly to the resistance element 306 or garment 300 it is removable received within a first recess 334 attached to the other of the resistance element 306 and garment 300. A second projection 336 is received within a second recess 338. A first pair of complementary engagement surfaces 340 is provided to create an interference fit within the first recess 334, and a second pair of complementary engagement surfaces 342 provide an interference fit within the second recess 338. This configuration can withstand a relatively high shear force such as might be experienced under tension, while at the same time enabling a relatively low release force such as by deformation of the pairs of complementary engagement surfaces as will be understood to those of skill in the art.

Figure 13:
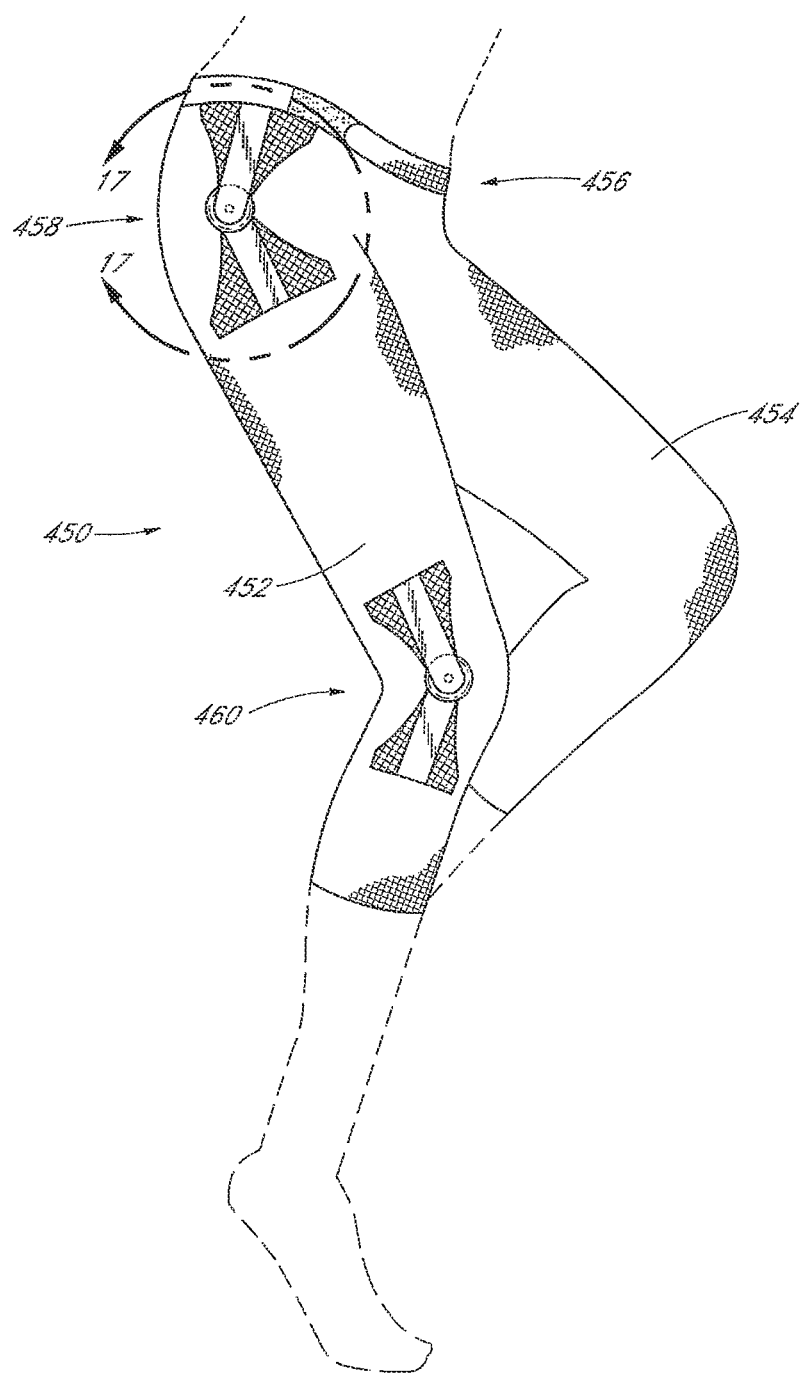
FIG. 13 is a side elevational view of a toning garment showing a right hip and a right knee resistance unit.

Referring to FIG. 13, there is illustrated a further toning garment 450 in accordance with the present invention. The toning garment 450 includes a right leg 452, a left leg 454, and a waist 456. As for all garments disclosed herein, the toning garment 450 will preferably be bilaterally symmetrical. Accordingly, only a single side will be discussed in detail herein.

Figure 28:
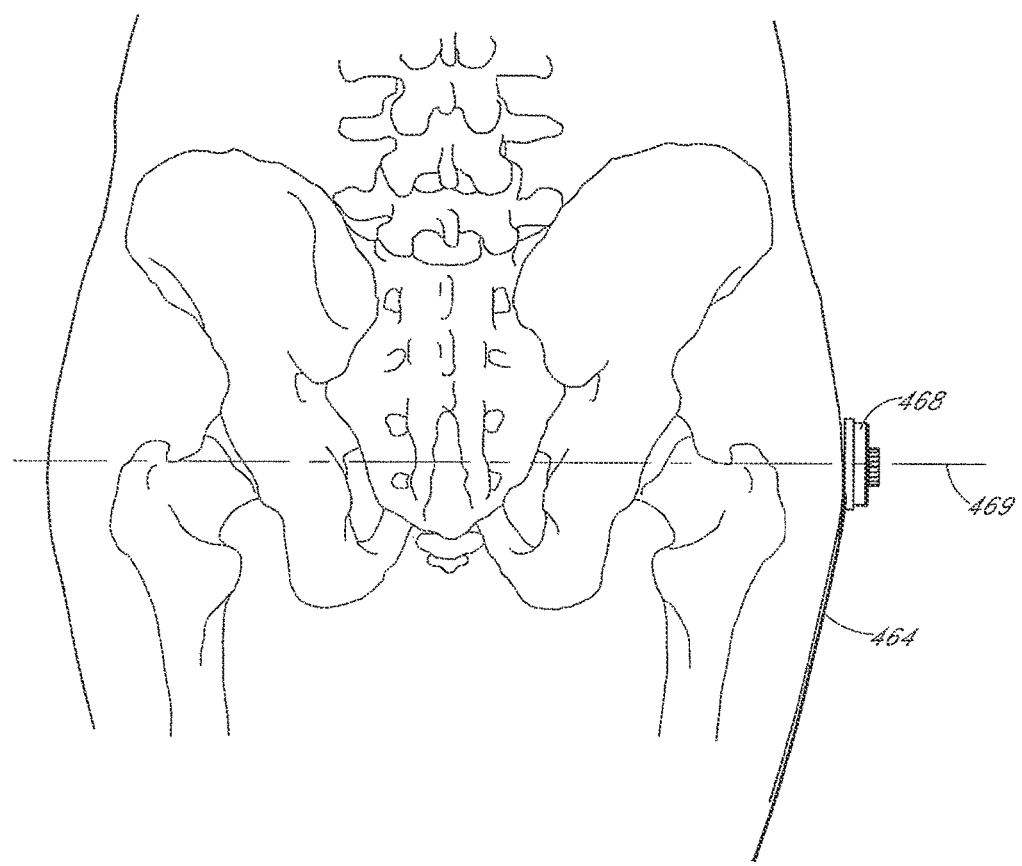
FIG. 28 is a posterior elevational view of a human pelvis, showing the axis of AP plane rotation relative to the iliac crest and a right side resistance unit of the present invention in an as worn orientation.

In the illustrated embodiment, the right leg 452 is provided with a hip resistance unit 458. Right leg 452 is additionally provided with a knee resistance unit 460. Each leg of the toning garment 450 may be provided with either the hip resistance unit 458 or the knee resistance unit 460, with or without the other. The left and right hip resistance units will preferably have an axis of rotation that is functionally aligned with a transverse axis of rotation which extends through the wearer's left and right hip axes of rotation. See, e.g., FIG. 28. Functional alignment includes precise alignment however due to the different fit that will be achieved from wearer to wearer, precise alignment may not always occur. Due to the stretchability of the garment, minor misalignment may self correct or not present adverse performance. Similarly, the knee resistance units, if present, will preferably have an axis of rotation that is functionally aligned with the transverse axis of rotation that extends through the center of rotation of each knee. Compensation for misalignment is discussed below.

Figure 14:
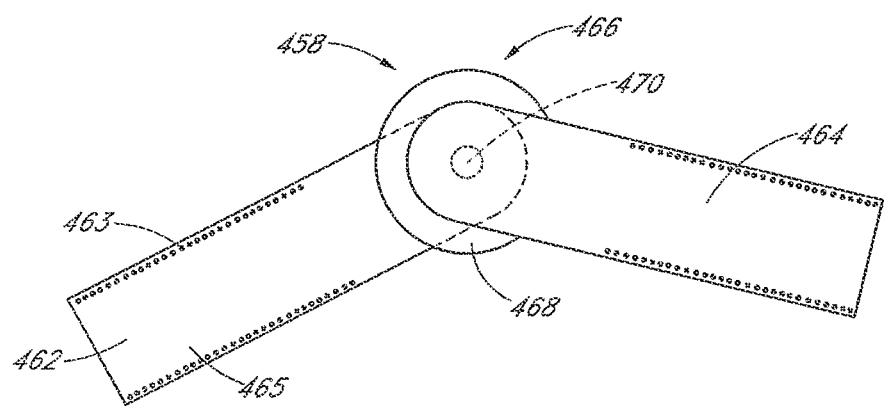
FIG. 14 is a plan view of a toning garment resistance unit.

Referring to FIG. 14, the hip resistance unit 458 will be described in further detail. The left leg hip resistance unit, and both the right and left leg knee resistance unit 460 may be constructed in a similar manner.

The hip resistance unit 458 is provided with a first attachment such as a first lever 462, and a second attachment such as a second lever 464 connected by a pivotable connection 466. The pivotable connection 466 comprises a resistance element 468 which provides resistance to angular movement between a primary longitudinal axis of first lever 462 and a primary longitudinal axis of second lever 464. In the as worn orientation, the axis of rotation 470 is preferably substantially aligned with an axis of rotation of the joint with which the resistance element is associated.

A lever as used herein refers to a structure that mechanically links a housing or rotatable component of a resistance unit to a portion of the garment or wearer at or above or below the resistance unit, so that movement of the wearer is resisted by the resistance unit without undesirable stretching of the garment. The lever may take a conventional form, as illustrated in FIG. 14, and comprise an elongate element having a length generally at least about 2 inches, in some embodiments at least about 4 or 6 or 8 inches to provide better leverage and attachment force distribution. The element may a have a width of at least about 0.25 inches, and in some embodiments at least about 0.5 inches or 1.0 inches or 2 inches or more but normally less than about 3 inches or 2.5 inches. The thickness may be less than about 0.25 inches, preferably less than about 0.125 inches and in some embodiments less than about 0.050 inches. The lever may comprise any of a variety of washable, non-corrosive materials such as nylon, Teflon, polyethylene, PEBAX, PEEK or others known in the art. Preferably the lever arm is sufficient to transmit force in the anterior-posterior direction in the case of hip and knee resistance units, but is flexible in the medial-lateral direction to enable the garment to follow the contours of the body. See, e.g., FIG. 28.

The inferior and superior lever arms may be similar to each other for a resistance unit mounted at the knee. For a resistance unit mounted at the hip, the lever arms may be distinct. For example, the inferior lever arm at the hip may conveniently comprise an elongated femoral lever, such as that illustrated in FIG. 13 or 27, in which the axial length of the lever is at least about two times, and may be at least about five times or eight times its width. This lever arm can extend down the lateral side of the leg, secured by the garment approximately parallel to the femur.

The superior lever arm may have a vertical component towards the waist, with a bend so that a superior component extends in a transverse direction, either partially or completely circumferentially around the waist of the wearer. Alternatively, the superior lever arm may comprise a fabric or plastic force transfer patch, such as a circular, square, rectangular, oval or other shape which can be secured to the rotational damper or a docking station for receiving the rotational damper, and also secured to the garment in a manner that resists rotation of the damper with respect to the garment during movement of the inferior lever. Thus, "lever" as used herein is a force transfer structure and is not limited to the species of a conventional elongate arm.

Figure 20:
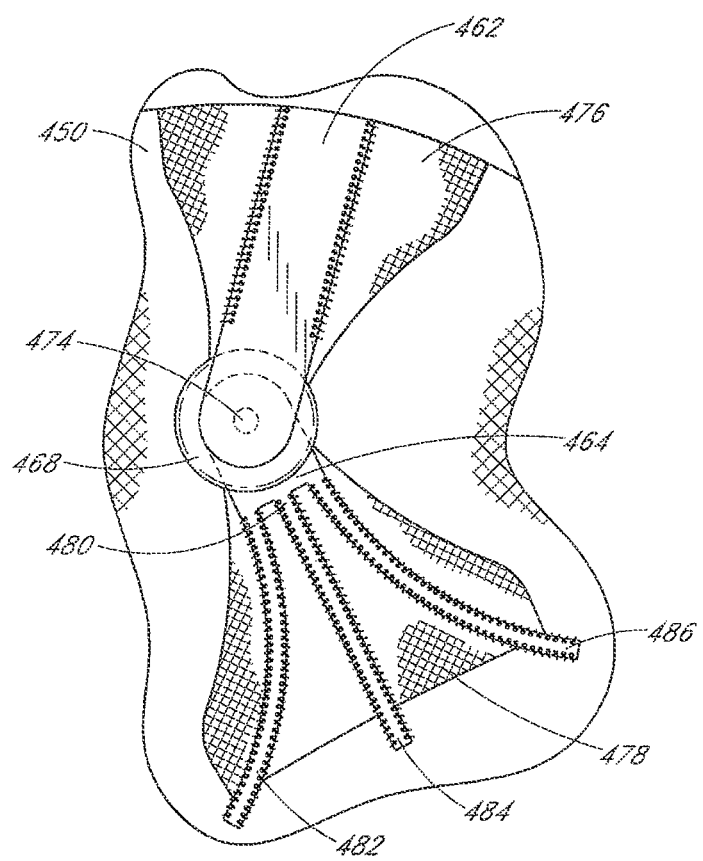
FIG. 20 is a resistance unit secured to a garment, showing an alternative reinforced femoral attachment configuration.

The lever may alternatively comprise a hub for attachment to the resistance unit, and a plurality of two or three or four or more elements that are secured such as by stitching or adhesive bonding to the garment. See FIG. 20 in which a hub 480 supports at least an anterior element 482, a medial element 484 and a posterior element 486. Each of the elements is preferably relatively inflexible in the anterior-posterior direction, but flexible in the medial-lateral direction to enable the anterior element 482 to wrap at least partially around the side and optionally around the front of the leg. The posterior element 486 preferably wraps at least partially around the posterior side of the leg. The lever elements can be configured as a system of straps similar to the straps 280 and 282 (FIG. 7). The elements can comprise one or more strands or technical fabric supports, sufficient to transmit the forces involved in a given garment and resistance unit system.

Figure 17:
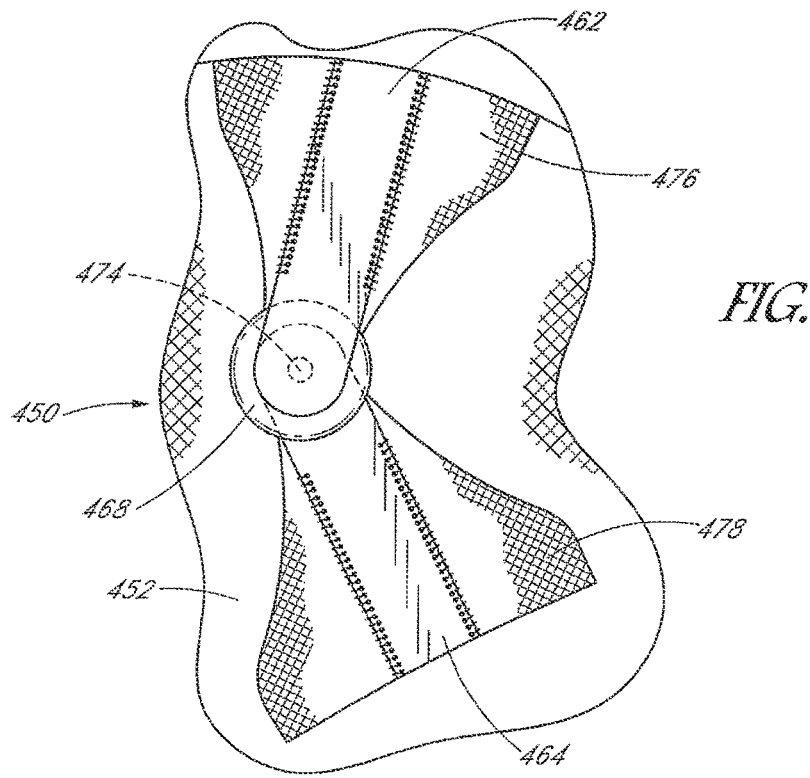
FIG. 17 is a resistance unit as in FIG. 14, attached to a garment with force distribution fabric layers.
Figure 18:
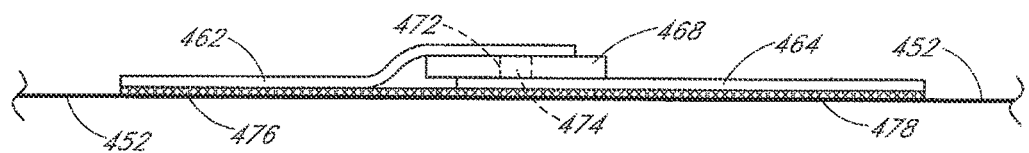
FIG. 18 is a side elevational view of the resistance unit and garment assembly of FIG. 17.

The hip resistance unit 458 may be secured to the toning garment 450 in any of a variety of ways. Referring to FIGS. 14 and 17, the first lever 462 is provided with at least a first set of apertures 463 and optionally a second set of apertures 465 to receive a filament such as a polymeric or fabric thread, for sewing the hip resistance unit 458 to the garment. Stitching may alternatively be accomplished by piercing the first lever 462 directly with the sewing needle, without the need for apertures 463 or 465. Alternatively, the first lever 462 can be secured to the garment using any of a variety of fastening techniques, such as adhesive bonding, grommets or others known in the art.

A lever is convenient for the inferior attachment, to distribute force along a portion of the length of the femur. The longitudinal axis of the first, superior attachment at the hip may be transverse to the longitudinal axis of the second lever 464 at the midpoint of its range of motion, such that the first lever is aligned like a belt, circumferentially extending along a portion of or approximately parallel to the wearer's waist. Normally the hip axis of rotation will be offset inferiorly by at least about 3 inches, and often 5 inches or more from the iliac crest, which approximates the belt line for many wearers. Alternatively, the housing of the resistance element may be sewn or adhesively bonded or otherwise attached directly to reinforced fabric at the hip.

The resistance element 468 may be any of the resistance elements disclosed elsewhere herein. In one embodiment, resistance element 468 may comprise a rotary damper containing a fluid such as air, water or a viscous media such as silicone oil. The rotary damper may be rated to provide anywhere within the range of from about 0.1 inch pounds to about 50 inch pounds torque depending upon the joint or other motion segment to be loaded and desired intensity. Generally, in a toning garment, torque at the hip may be in the range of from about 2 inch pounds to about 8 inch pounds, and often no more than about 6 inch pounds. For the athletic training market, higher torques such as at least about 3 or 5 or 7 inch pounds, and some implementations at least about 10 or 15 inch pounds or higher may be desirable at the hip.

Torque at the knee will generally be less than at the hip. Values of generally no more than about 85% or 50% or 35% of the torque at the hip may be desirable in a toning garment at the knee, measured at 30 RPM for fully rotational dampers at approximately STP. As discussed elsewhere herein, the resistance element at any given joint can provide the same or different resistance (including zero) upon flexion or extension.

Figure 15:
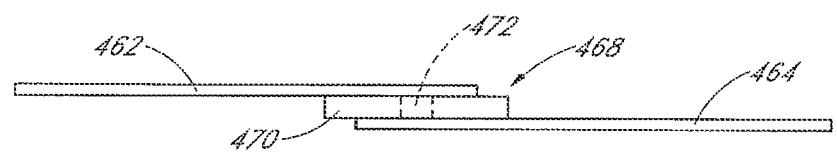
FIG. 15 is a side elevational view of the resistance unit of FIG. 14.
Figure 16:
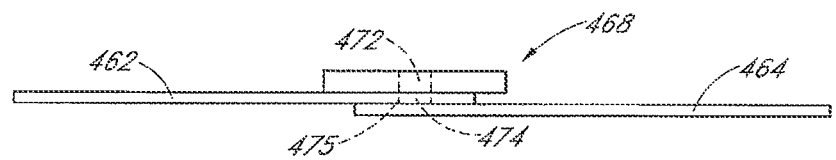
FIG. 16 is a side elevational view of an alternate configuration of the resistance unit of FIG. 14.

Referring to FIGS. 15-16, the resistance element 468 may comprise a generally disc shaped housing, having a diameter of less than about 4 or 3 or 2.5 inches, and a thickness in an axial direction of less than about 0.75 and preferably less than about 0.5 inches. A connector 472 is rotatably carried by the housing 468. Connector 472 may be a post or an aperture, having a non-circular (e.g. square, hexagonal, triangular, circular with at least one spline or flat side) cross-section such that a complementary post or aperture may be axially positioned in engagement with the connector 472, to transmit rotational torque.

Referring to FIGS. 15-16, the resistance element 468 housing may be secured to either the first lever 462 or the second lever 464. The connector 472 may be secured to the other of the first lever 462 and second lever 464. Resistance element 468 thus provides resistance to motion of the first lever 462 with respect to the second lever 464, throughout an angular range of motion about the axis of rotation 470.

In an alternative configuration, the levers may be mounted on the same side of the resistance element 468 to provide an overall lower profile. Referring to FIG. 16, second lever 464 is provided with a post for rotationally engaging the connector 472 which is in the form of a complementary aperture. Post 474 extends through an aperture 475 in the first lever 462. Aperture 475 has a diameter that exceeds the maximum transverse dimension of the post 474, such that post 474 may rotate without imposing any force on first lever 462. The housing of resistance element 468 is immovably secured with respect to first lever 462 such as by adhesive bonding, molding, interference snap fit or other immovable connection.

Referring to FIG. 17, a hip resistance unit 458 is illustrated as secured to a garment 450 although the following description also applies to resistance elements at the knee. Depending upon the configuration of the lever arms, the stretchability of the fabric, and the level of resistance imposed by resistance element 468, one or more reinforcement or force transfer or dissipation features may be necessary to transfer sufficient force between the lever arm and the garment, while minimizing stretching or wrinkling of the garment. In the illustrated embodiment, first lever 462 is additionally provided with a first force dissipation layer 476. Force dissipation layer 476 may comprise any of a variety of fabrics, such as those disclosed previously herein and below in connection with FIG. 25A.

In one implementation, the fabric comprises one or more strands of yarn or filament 477 having a vector extending in the as worn anterior posterior direction which exhibits relatively low stretch. See FIG. 25A. A plurality of strands 477 can be woven in an orientation that is approximately at a tangent to at least about 2 or 4 or 8 or 10 or more points around the resistance element housing to optimize resistance to rotation of the housing relative to the garment. Force dissipation layer 476 may be attached to the edges and/or lateral and/or medial surfaces of first lever 462 or the damper housing or docking station for receiving a damper such as by stitching, adhesives or other fastener, and extend in the anterior posterior direction beyond the edges of the first lever 462 to provide an attachment zone both anteriorly and posteriorly of the first lever 462. In the embodiment of FIG. 25A, the force dissipation layer is the lever, securing the damper against rotation with respect to the adjacent fabric. The attachment zones may be secured to the underlying garment by stitching, adhesives or both, or straps, strands or other fasteners known in the art.

The first force dissipation later 476 may extend beneath, within the same plane, or across the outside (lateral) surface of the first lever 462, entrapping the first lever 462 between the force dissipation layer 476 and the garment 450.

The force dissipation layer is preferably a technical fabric weave, comprising any of a variety of strands identified previously herein. Preferably the fabric has stretch resistance along at least one axis, which can be aligned with an axis under tension during flexion or extension due to the resistance element (e.g. the AP plane). The fabric may exhibit a higher level of stretch along other axes. The fabric also preferably exhibits low weight, high breathability and high flexibility. Some suitable fabrics include shoe upper fabric from running shoes including, for example, that disclosed in US patent publication No. 2014/0173934 to Bell, the disclosure of which is incorporated by reference in its entirety herein. Additional multilayer fabrics having good flexibility, and stretch resistance along one axis and higher stretch along a transverse or nonparallel axis, useful for the force dissipation layer are disclosed in U.S. Pat. No. 8,555,415 to Brandstreet et al; U.S. Pat. No. 8,312,646 to Meschter et al; and U.S. Pat. No. 7,849,518 to Moore et al., the disclosures of each of which are incorporated in their entireties herein by reference.

Figure 21:
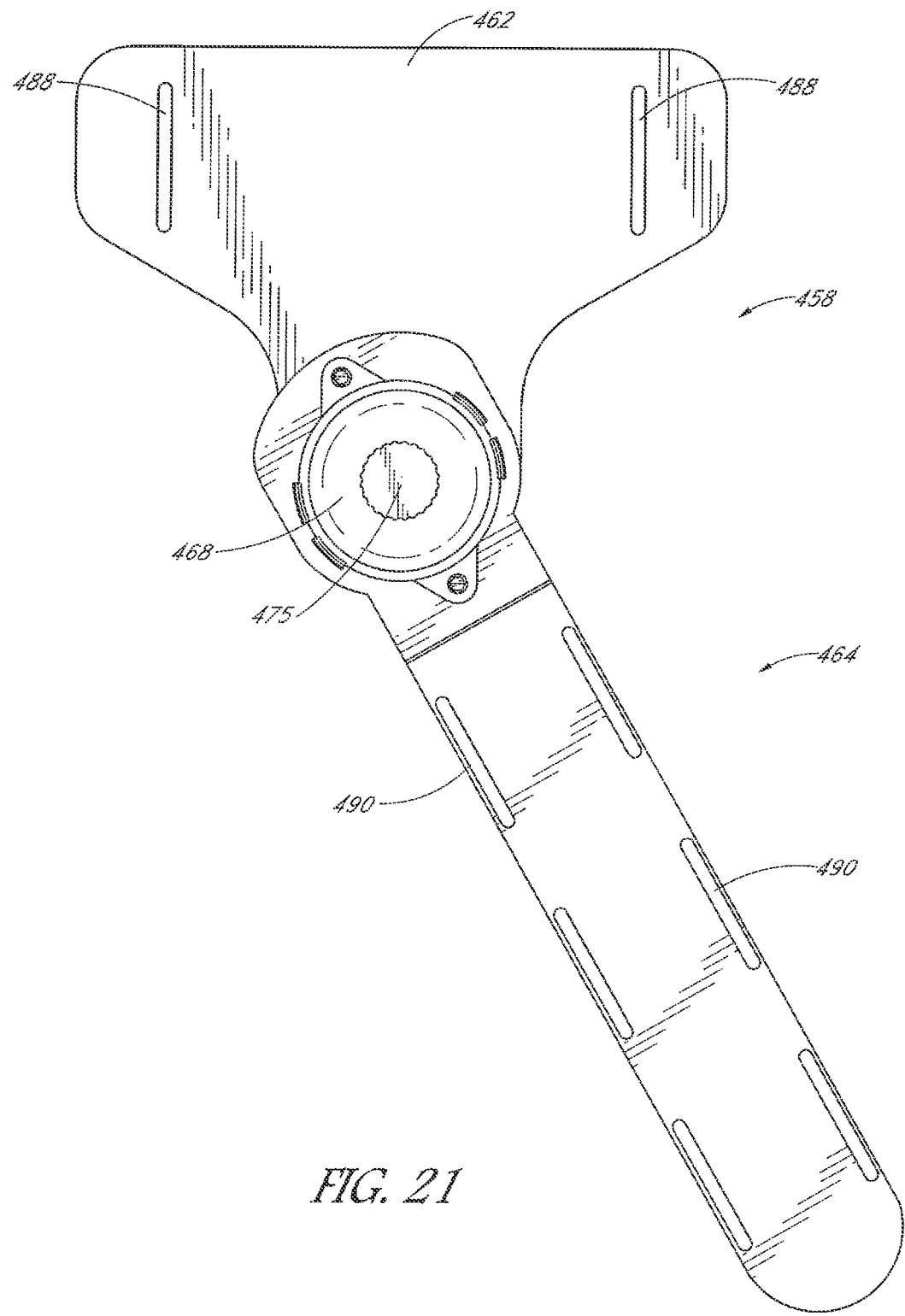
FIG. 21 is a side elevational view of a resistance unit having a superior connector, an inferior, femoral connector and a resistance element.

Referring to FIG. 21, there is illustrated a resistance unit 458 comprising a first lever 462 configured for attachment to the garment to at least approximately align the rotational axis of the resistance element with the hip, as discussed below. First lever 462 may be provided with any of a variety of attachment structures such as a force dissipation layer, Velcro or at least one and typically two or more slots 488 for connection to a strap, belt or other fastener associated with the garment. First lever 462 may comprise any of a variety of polymeric membranes or fabrics disclosed elsewhere herein, which may be bonded or stitched directly to the garment, or held by a belt to the outside of the garment.

Figure 19:
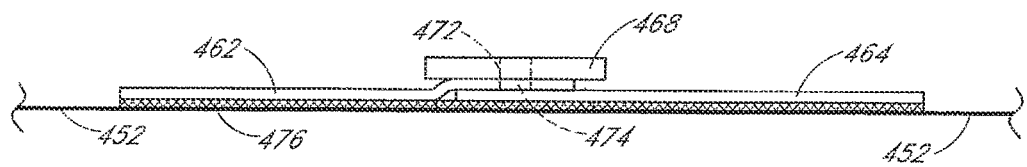
FIG. 19 is a side elevational view of an alternate configuration of the resistance unit and garment assembly of FIG. 17.

Lever 462 is pivotably connected to a second lever 464 by way of resistance element 468 as has been described. Resistance element 468 may comprise any of a variety of resistance elements, such as friction brakes, malleable materials, clutches, or rotary viscous dampers as has been discussed. Resistance element 468 may be securely permanently or removably mounted to the second lever arm 464 (as illustrated) or to first lever arm 462 or both. A post 474 (FIG. 19) is secured to the first lever arm 462, and extends through a complementary aperture in the resistance element 468. In this manner, rotation of the second lever 464 about the rotational axis of resistance element 468 with respect to the first lever 462 experiences the resistance provided by resistance element 468. Second lever 464 may be provided with a force dissipation layer and/or one or two or three or four or more inferior connectors 490. As illustrated, inferior connectors 490 may be apertures such as slots for receiving a strap or filament for securement to the pant leg.

Preferably, a quick release 475 is provided, to engage and disengage the resistance, and or enable disassembly into component parts. Quick release 475 is illustrated as a knob which may be rotatable, or axially movable between a first and a second position to engage or disengage the damper. Any of a variety of quick release mechanisms maybe utilized, such as a threaded engagement, or a pin or flange which can rotate into engagement behind a corresponding flange or slot. Quick release 475 allows rapid removal of the damper, or the damper and femoral lever arm, as is discussed in more detail below.

Figure 22:
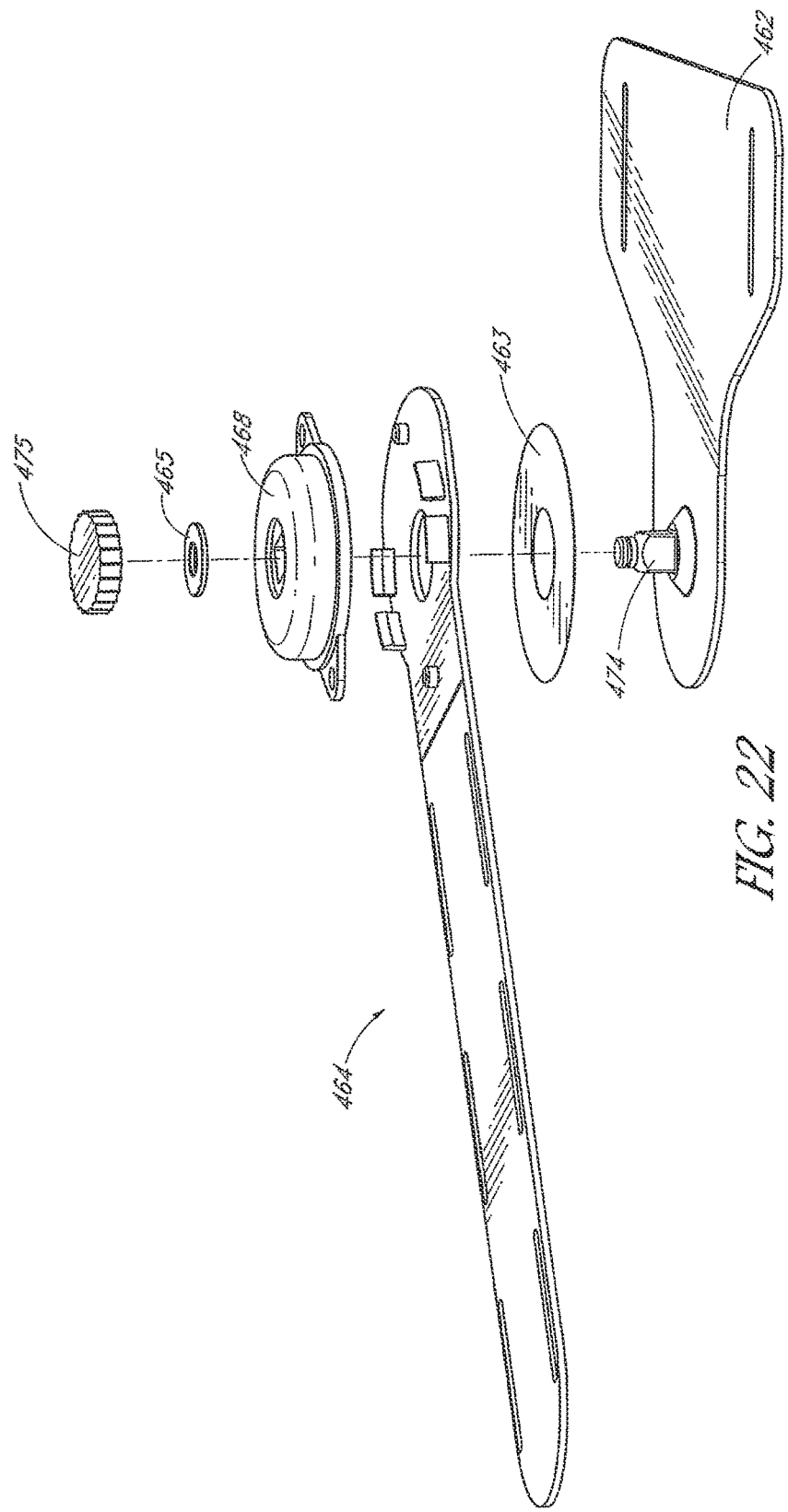
FIG. 22 is an exploded view of the resistance unit of FIG. 21.

Referring to FIG. 22, an exploded view illustrates the first lever 462 having post 474 secured thereto such that rotation of the post is transferred to the lever. A friction modifier 463 such as a washer or membrane that may comprise a friction reducing material such as a lubricious polymer (e.g., PTFE) may be provided to separate the first lever 462 from second level 464. Alternatively the friction modifier 463 may be a friction enhancer, such as one or two or more washers having a friction enhancing surface texture, which create resistance to movement and can therefore supplement or replace the rotational damper.

Connectors 465 may be provided for locking the construct together. Connectors 465 may comprise one or more locking rings, nuts, pins or other structure. Preferably, a quick release mechanism 475 such as a quick release lever, rotatable knob or snap fit that allows the wearer to quickly engage or disengage the resistance unit 458 into component subassemblies, as will be described.

Figure 32:
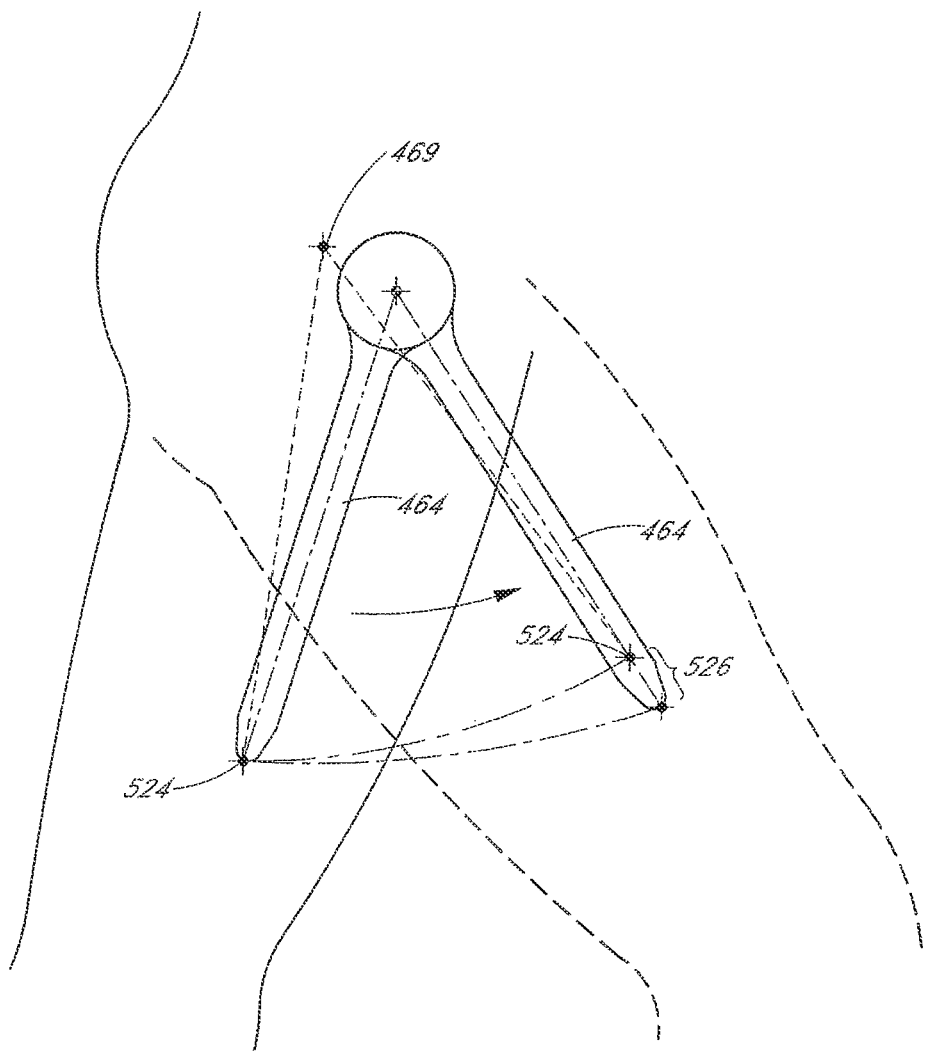
FIG. 32 is a schematic illustration of a rotational axis offset between the hip and resistance element axes of rotation.

Skeletal motion at the hip during normal activities including walking involves complex, multidirectional movement of the femoral head within the acetabular cup. However when viewed to isolate out the single component of movement in the anterior-posterior ("AP") plane, the femur swings forward and back like a pendulum, pivoting about a rotational axis 469 (FIGS. 28 and 32) which extends laterally through the approximate centers of the roughly spherical left and right femoral head. The length of the femur remains unchanged throughout the stride cycle, such that the linear distance from the axis of rotation 469 and a reference point 524 on the femur remains constant throughout the walking cycle. The reference point 524 may be approximately half way between the proximal limit of the femoral head and the distal limit of the medial condyle although any other fixed reference point could be used.

Many of the resistance elements disclosed herein exhibit a fixed axis of rotation. Ideally, the exercise garment of the present invention of the type having a fixed rotational axis can be worn by a wearer such that the rotational axis of the resistance element is coincident with the rotational axis 469 of the femur. However, due to a combination of factors including the stretch of the fabric and dissimilarities from wearer to wearer in the contour of the soft tissue between the femur and the garment, the two rotational axes will normally not perfectly align. An imaginary straight-line in the AP plane which connects the anatomical rotational axis 469 and the rotational axis of the resistance element defines an offset which has the effect of pulling or pushing the second lever 464 along its longitudinal axis relative to the femur throughout the stride cycle. If force in all directions from the second lever 464 is effectively transmitted to the garment, this axial reciprocal movement of the second level 464 with respect to the wearer and garment through the offset distance 526 may cause a variety of undesirable results, including chafing of the garment up and down against the leg, wrinkling or buckling the fabric of the garment and/or the material of the second lever 464.

It may therefore be desirable to decouple axial movement of the second lever 464 from the garment, while maintaining a high degree of force transmission between the second lever 464 and the garment in the AP plane.

Figure 25:
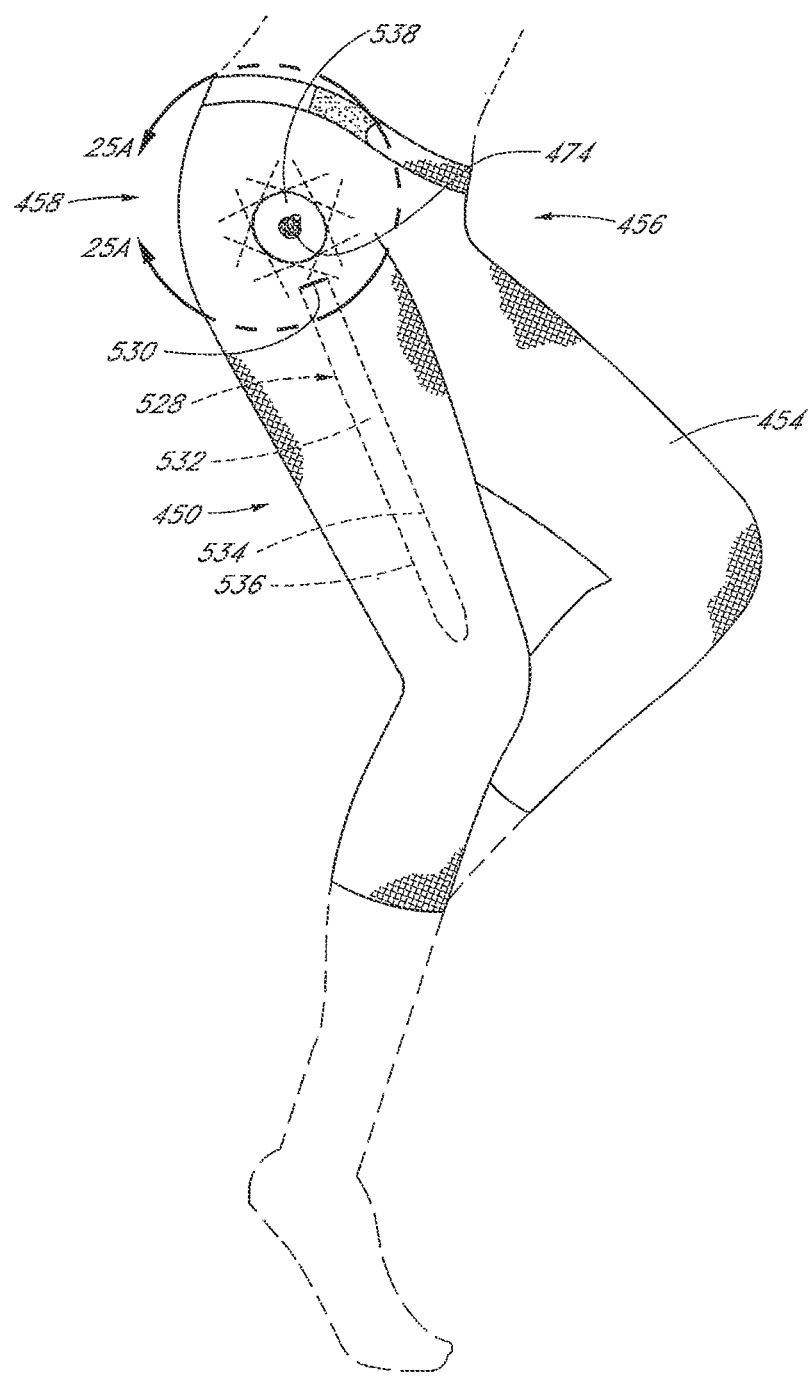
FIG. 25 is a side elevational view of a lower body garment, having a resistance unit docking station aligned with the hip.
Figure 25A:
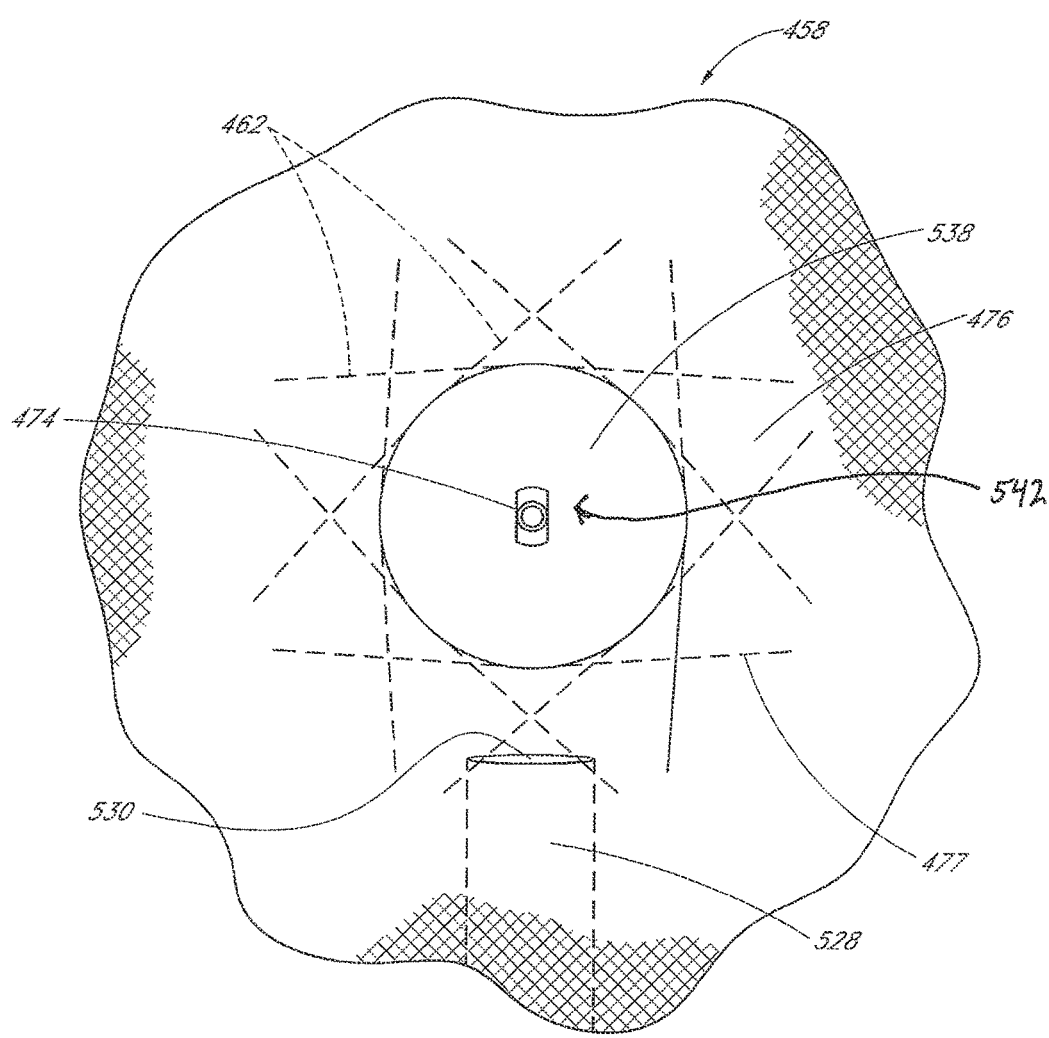
FIG. 25A is a detail view taken along the line 25A-25A in FIG. 25.

Referring to FIG. 25, one convenient structure for accomplishing the foregoing is to provide an elongated pocket 528 extending in an inferior superior direction along the lateral side of each leg of the garment. The pocket 528 comprises an opening 530 at a superior end thereof, providing access to an elongate cavity, for removably receiving the second lever 464. An anterior limit 534 of the pocket 528 and a posterior limit 536 of the pocket 528 are dimensioned relative to the width of the second lever 464 to provide a snug fit against relative AP movement, but which permits axial sliding of the second lever 464 along its longitudinal axis within the pocket. The axial length of the pocket exceeds the axial length of the second level 464, thereby enabling the second level 464 to reciprocate up and down within the pocket 528 without transmitting inferior superior plane movement to the garment.

The axial length of the pocket 528 is preferably at least about 8 inches, and in some implementations it is at least about 10 inches or 12 inches or 14 inches or more in length, depending upon the garment size, fabric stretch and resistance level of the resistance unit. The length of the pocket will preferably exceed the length of the associated lever by an amount sufficient to compensate for the likely offset 526 between the rotational axis of the hip and the rotational axis of the damper. Typically, that offset will be less than about 2 inches, and preferably less than about 1 inch or 0.5 inches. The lever 464 will preferably axially reciprocate within the pocket 528 with minimal friction. For this purpose, the lever may be constructed from or coated with a lubricious material. In addition, the interior surface of the pocket preferably comprises a material with a low coefficient of friction with respect to the surface of the lever. The interior of the pocket 528 may be provided with one or two or five or 10 or more axially extending filaments or raised ridges, to reduce the contact surface area between the lever 464 and the pocket 528. The interior of the pocket 528 may be lined either partially or completely with a membrane having a low friction surface. Thus, a pocket liner comprising any of a variety of materials such as nylon, PTFE, polyethylene terephthalate, PEEK, metal films or other materials may be utilized depending upon the intended performance characteristics.

The inside width of the pocket is preferably dimensioned such that the lever is not able to move significantly in the AP plane with respect to the pocket. The width of the pocket therefore preferably only exceeds the width of the lever by a sufficient amount to permit the desired axial movement of the lever without transferring axial movement to the garment. Alternatively, the width may be adjustable between a larger width such as for inserting the lever, and a smaller width for efficient lateral force transfer. That may be accomplished by advancing a zipper along the length of the pocket to bring two parallel reference edges closer together, with straps connected to the pant leg on one side of the pocket and connectable (e.g., with Velcro) to the pant leg on an opposite side of the pocket.

Alternatively, the resistance unit 458 can be provided with any of the variety of axial expansion dampers, positioned between the rotational axis of resistance element 468 and a portion of the second lever 464 which is immovably secured to the garment. Axial extension dampers may include first and second side by side or concentric telescoping components, which through relative axial sliding motion allow the second lever 464 or other attachment point to the garment to reciprocally lengthen and shorten. Alternative structures such as springs, diamond shaped cells, etc., can allow axial shortening and lengthening of the second lever 464 between the rotational axis and the point of attachment to the garment so that reciprocating movement of the femoral lever is not transmitted to the garment. The proximal end of the lever may be provided with an elongate, axially extending slot which receives a post on the damper having two opposing flat sides so that the lever can reciprocate axially but remain rotationally keyed to the post.

Referring to FIG. 25, there is illustrated a docking station 538 for releasably receiving a resistance module 568. As illustrated in FIG. 25A, the docking station 538 comprises a platform 540 for receiving a damper or other resistance module. The platform 540 comprises at least one connector 542, for connecting with the resistance module. The connector may be a post or an aperture, for keyed connection with a corresponding connector on the damper or other resistance module. The platform 540 or connector 542 may be provided with a quick release feature 544, for releasably engaging a complementary quick release control such as a lever, button or rotatable knob as has been discussed.

Figure 23:
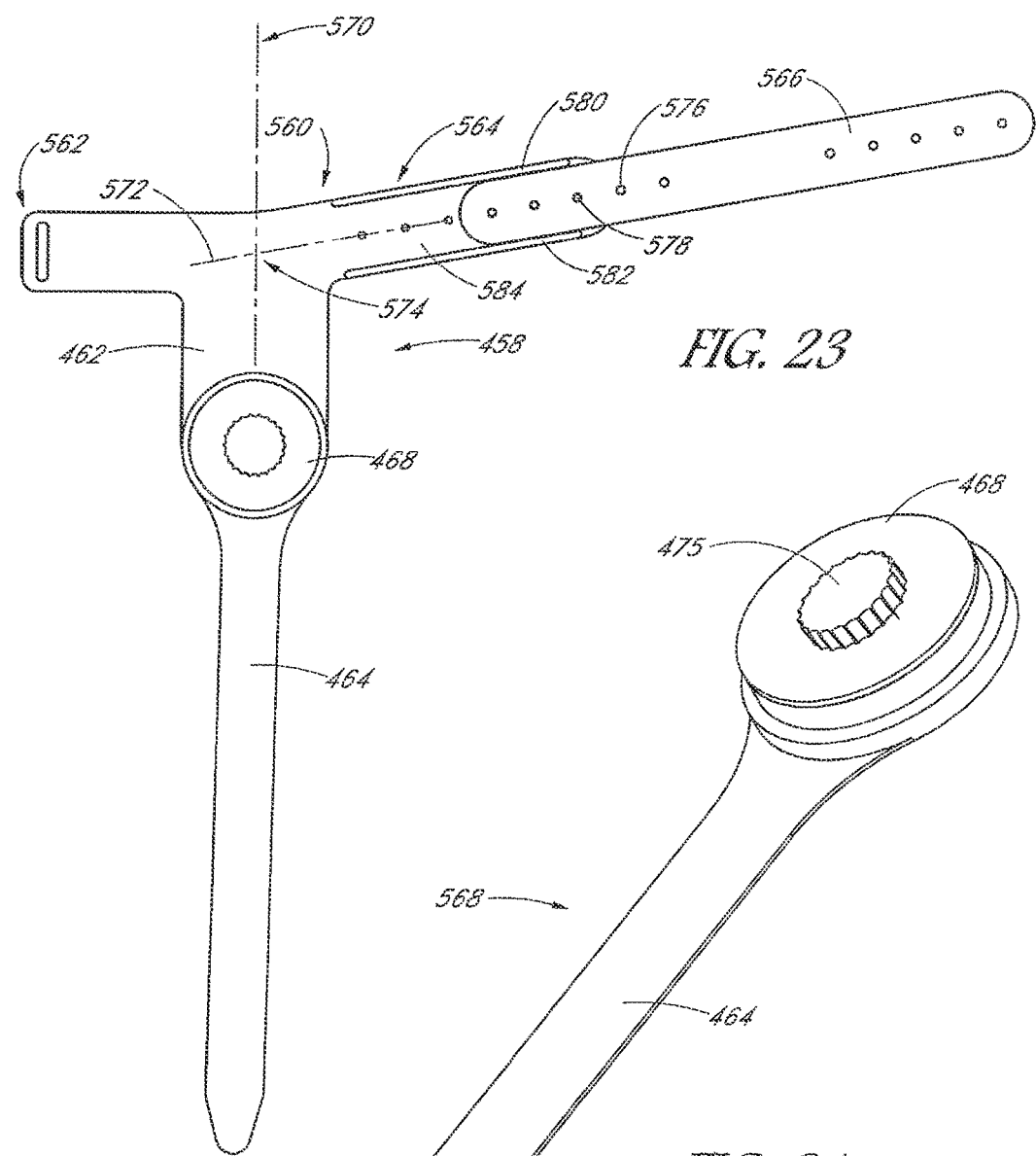
FIG. 23 is a side elevational view of a left side resistance unit, having a posterior connector for connection to a right side resistance unit.

Referring to FIG. 23, there is illustrated a left side resistance unit 458 with the right side omitted for clarity. The resistance unit 458 comprises a femoral lever 464 and a resistance element 468 as has been described. In this illustration, the first lever 462 is in the form of an approximately "T" or "Y" shaped hip support 560, configured to minimize the risk of rotation of the resistance element 468 with respect to the wearer. Hip support 560 comprises an anterior connector 562, such as a buckle or strap or other fastener for fastening across the anterior of the wearer's waist. The hip support 560 additionally comprises a posterior connector 564, for connection to or across the posterior side of the wearer or garment. In the illustrated embodiment, posterior connector 564 is adjustably connected to a posterior strap 566. The posterior strap 566 may be configured to extend across the posterior of the wearer and to connect to a right side resistance unit 458, such that the hip support 560 is connected to both the right and left resistance units 458, encircling at least a portion and preferably all of the waist of the wearer in the as worn configuration.

The axis of rotation of the resistance element 468 is displaced from the wearer's waist line along an inferior-superior axis 570. The posterior connector 564 extends along a longitudinal axis 572 which intersects with the axis 570 at an angle 574. The angle 574 deviates from perpendicular by at least about 2°, and in some embodiments at least about 3° or 5° or more.

The posterior strap 566 maybe adjustably connected to the posterior connector 564. In one implementation, one of the posterior strap 566 or connector 564 is provided with a plurality of apertures 576. The other is provided with at least one post 578. In an alternate embodiment, the two components may be secured by Velcro, or a buckle. In a further implementation, the strap 566 is slidably engaged with the posterior connector 564. This may be accomplished, for example, by providing a first raised rail 580 and a second raised rail 582 defining a recess 584 there between within which the posterior strap 566 can slide. Posterior connector 564 may be retained within the recess 584 such as by a flange on one or both of the rails 580 and 582, or by connecting the rails 580 and 582 to form an enclosure for receiving posterior connector 566. Enclosure may be formed by a plastic restraint, integrally formed with the posterior connector 564, or by a fabric enclosure.

The components of the hip support 560 may comprise polymeric membranes, various technical fabrics as has been described elsewhere herein, or combinations of the two, in order to optimize comfort, fit and structural integrity of the connection of the hip support 562 to the wearer. Any portions or all of the hip support may be distinct structures attached to or worn over the top or under the garment, or may be structural fabric and components woven or sewn into the garment.

Preferably, the hip support 560 is constructed largely in fabric, such that it has sufficient flexibility and durability to be comfortable, durable, and able to withstand normal washing and drying cycles. In a preferred embodiment, the first lever 462 is provided with a docking station for removably receiving and engaging the resistance element 468 and second lever 464.

Figure 24:
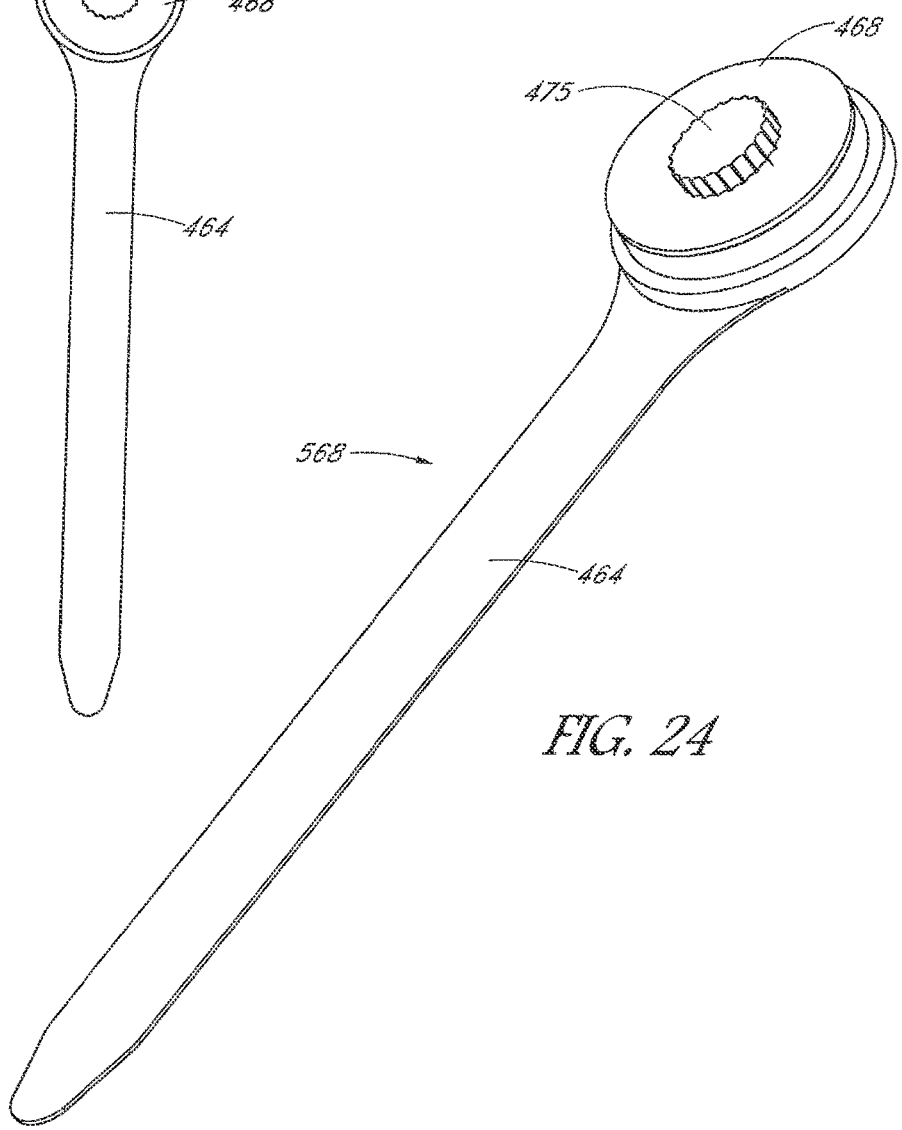
FIG. 24 is a perspective view of a detachable, modular resistance unit, having a resistance element and a femoral lever arm.

Thus, referring to FIG. 24, a modular detachable femoral resistance component 568 may be provided. The femoral component 568 may comprise one or both of the second lever 464 and the resistance element 468. In the illustrated embodiment, resistance element 468 is bonded or otherwise secured to the second lever arm 464 to provide an integral modular femoral resistance component 568.

Figure 26:
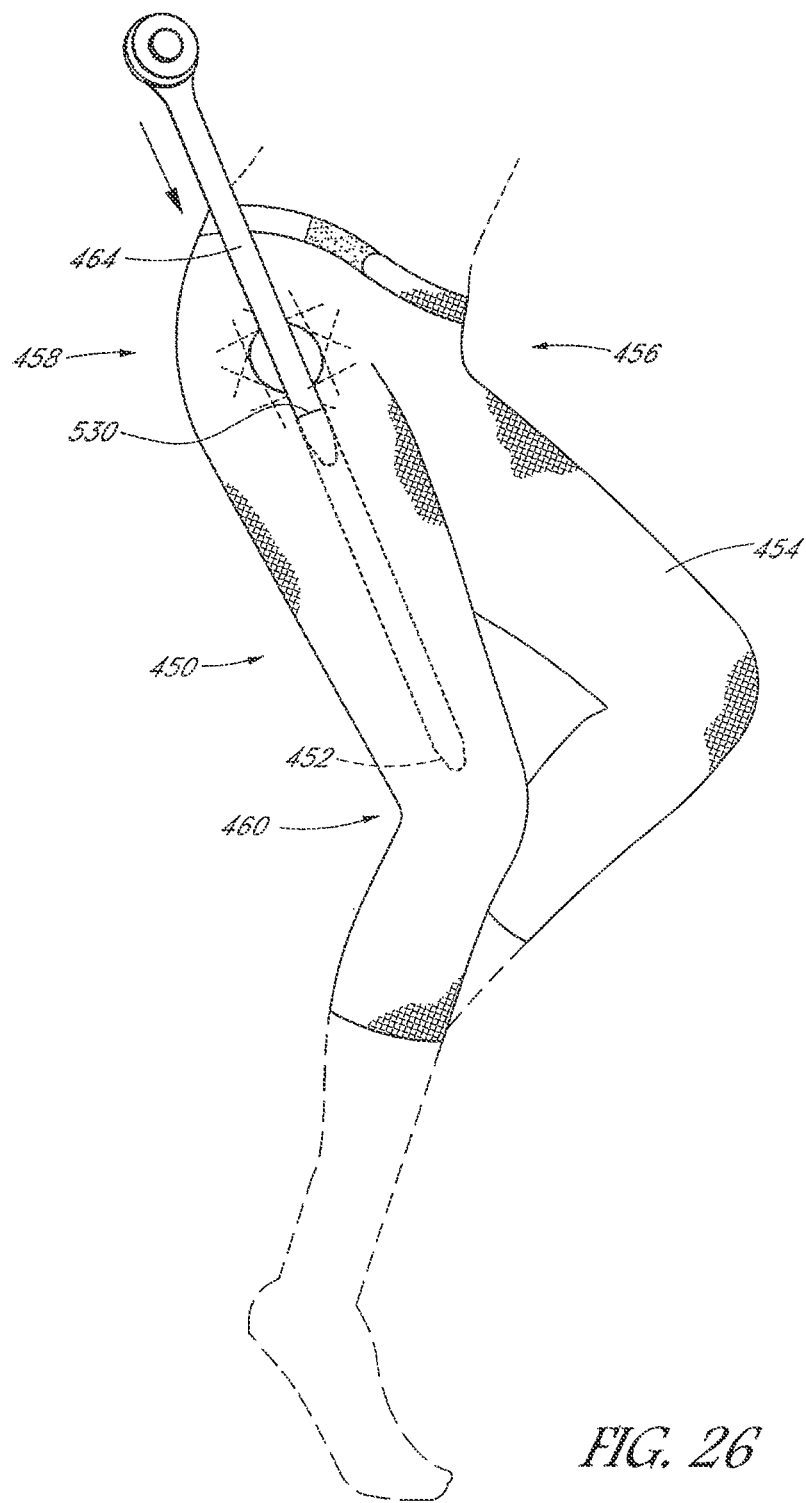
FIG. 26 is a garment as in FIG. 25, with a removable modular resistance unit partially assembled with the garment.
Figure 27:
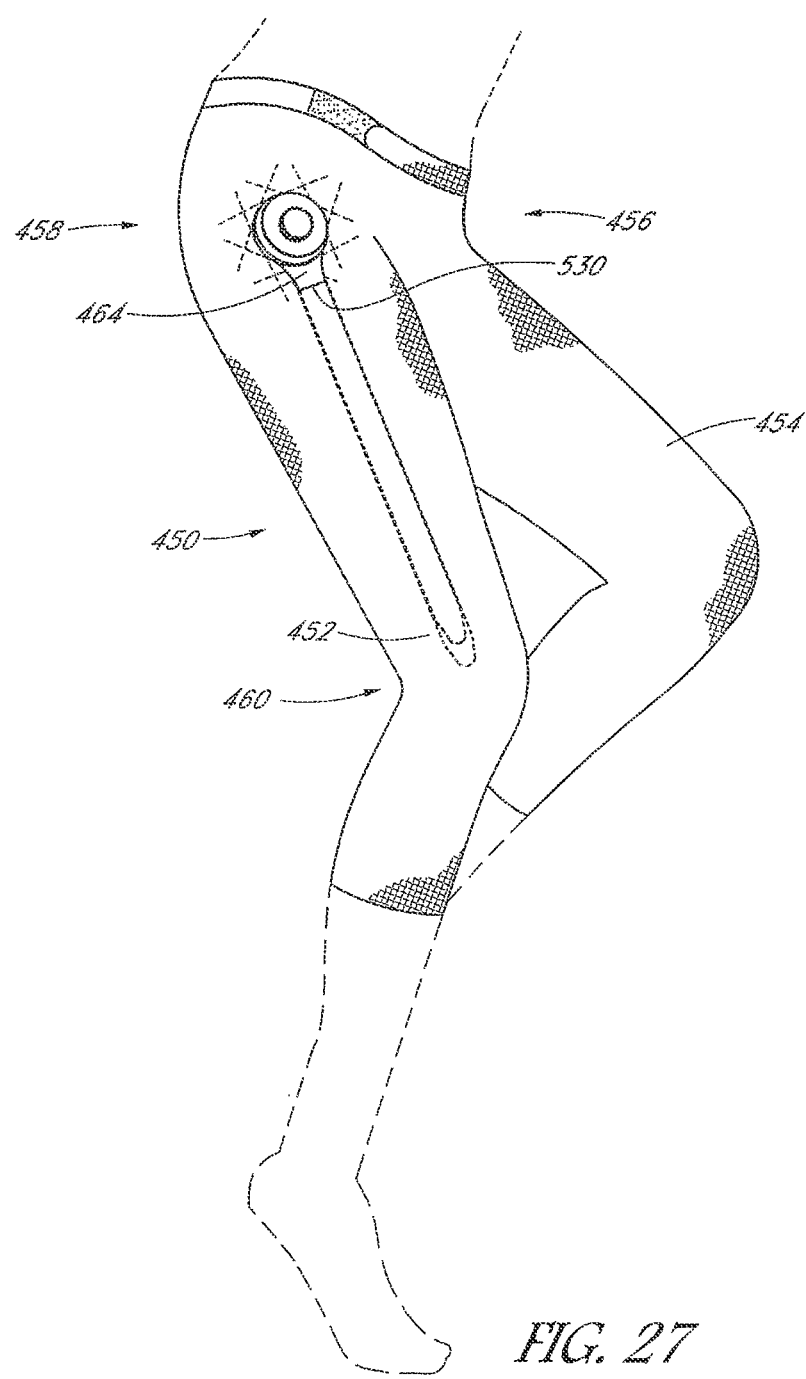
FIG. 27 is a garment as in FIG. 26, with the removable modular resistance unit fully installed, and engaged with the docking station.

Referring to FIGS. 26 and 27, this configuration allows the wearer to put the garment on with just the hip support 560 secured thereto. Once the garment is on, the second lever 464 may be inserted within the pocket 528 running down the lateral side of the leg or otherwise removably secured to the garment or the wearer's leg. The resistance element 468 is then aligned with the docking station on first lever 462, seated and coupled thereto. This may be accomplished by advancing a first connector such as the aperture on resistance element 468 over a second, complementary connector such as the post on first lever 462 to achieve rotational engagement, and locking the resistance element 468 into place using any of a variety of quick lock or release features. These include interference (snap) fit, or any of a variety of twist connectors, locking pins or levers or others known in the art.

The modular femoral resistance component 568 may be uncoupled from the docking station by manipulating the quick release control, and removed from the garment such as to permit removing the garment from the wearer, and or placing the garment in the wash. In addition, a wearer may be provided with a plurality of matched pairs of modular femoral components 568, each pair having resistance elements 468 with a different level of resistance. This modularity enables the wearer to select the desired level of resistance depending upon a given use environment, as well as to facilitate washing, and optimizing the useful life of whichever components of the detachable component resistance toning system have the greatest useful life.

Rotary dampers (sometimes called dashpots) suitable for use in the present invention are precision fluid damping devices which give a smooth resistance to shaft rotation which increases with angular velocity. At least of two types of dashpot may be used with the present invention, in view of the reciprocating, limited range of motion associated with the human stride. Vane dashpots give a restricted travel and high damping rate particularly suitable for reciprocating motions. Continuous rotation dashpots give less damping rate but unlimited travel which is useful but not necessary in the context of the toning and training garments of the type, for example, illustrated in FIG. 31. Continuous rotation dashpots may be desirable in certain constructs, such as in connection with an embodiment, in which resistance element includes a rotary damper with a spool and cable system which may rotate through more than one full revolution per stride in each direction depending upon the pulley diameter and potential gear configurations.

Silicone fluid (Polydimethyl Siloxane) is a suitable damping medium because of its stable viscous properties. A variety of other dampening media may also be used such as fluorocarbon gels or other viscous grease products, water or air depending upon damper design and intended performance. Dashpots are normally vacuum filled and sealed for life, and the housing or coatings on the housing can comprise materials having good corrosion resistance in the intended use environment. That environment includes repeated exposure to salinity and other content of perspiration as well as detergents and other solutes utilized in conventional clothes washing machine cycles. Other fluids such as air or water may alternatively be used.

The vane dashpot is a displacement damper. As the vane or piston on the shaft rotates between one or more fixed vanes or barriers on the body, silicone fluid is displaced through controlled clearances from one side of the fixed barrier to the other. Damping can be in both directions or valves can be fitted to give damping in one direction only. Thus, for example, the hip or knee or both may be provided with resistance in both directions or against anterior motion (like walking through waist deep water) but no resistance or low resistance against posterior motion. Continuous rotation dashpots give viscous damping by shearing thin layers of silicone fluid between the concentric surfaces of a rotor and a fixed stator.

Damping can be adjusted in the case of dampers that utilize electro-rheological fluid (ERF) or magneto-rheological fluid (MRF), by changing the viscosity of the fluid.

In an MRF damper, micron-sized, magnetically polarized particles are suspended in a carrier fluid such as silicone oil or mineral oil. MRF is capable of responding to an applied magnetic field in a few milliseconds. The material properties of an MRF can change rapidly by increasing or decreasing the intensity of the applied magnetic field. The material property can be viewed as a controllable change in the apparent viscosity of the fluid by varying the current supplied to, for example, an adjacent electromagnet. A higher fluid apparent viscosity can be exploited to provide a higher damping force or pressure-drop across an MRF valve.

Energy to drive the electromagnet and associated electronics can be supplied by a battery, solar cells, or an on board generator to scavenge electricity from body heat or motion. In one implementation, a rotational generator may be carried by the garment and driven by rotational movement at the hip or the knee or both. A control may be provided to allow the wearer to toggle between a low resistance and a high resistance mode, or to also adjust the resistance to intermediate values as desired.

Figure 29:
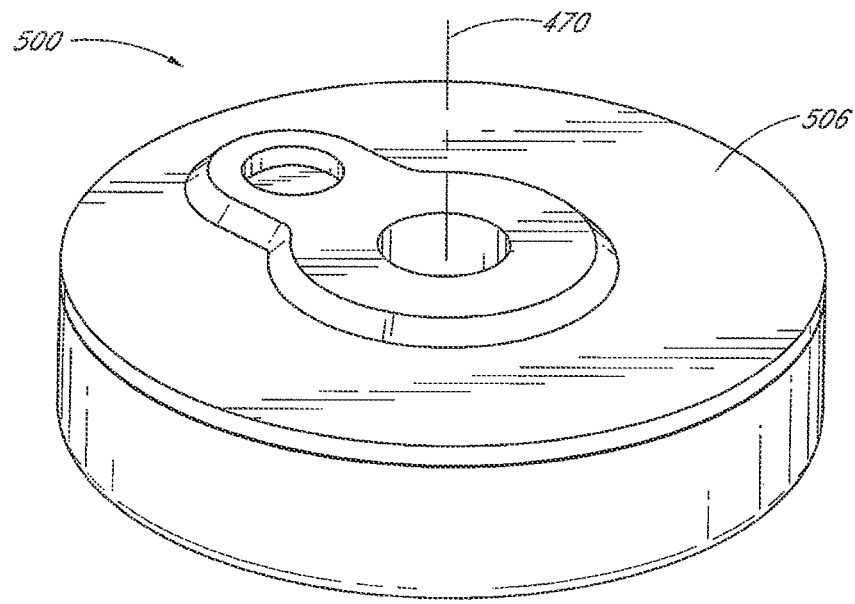
FIG. 29 is an enlarged, perspective view of a rotary damper useful in the present invention.
Figure 30:
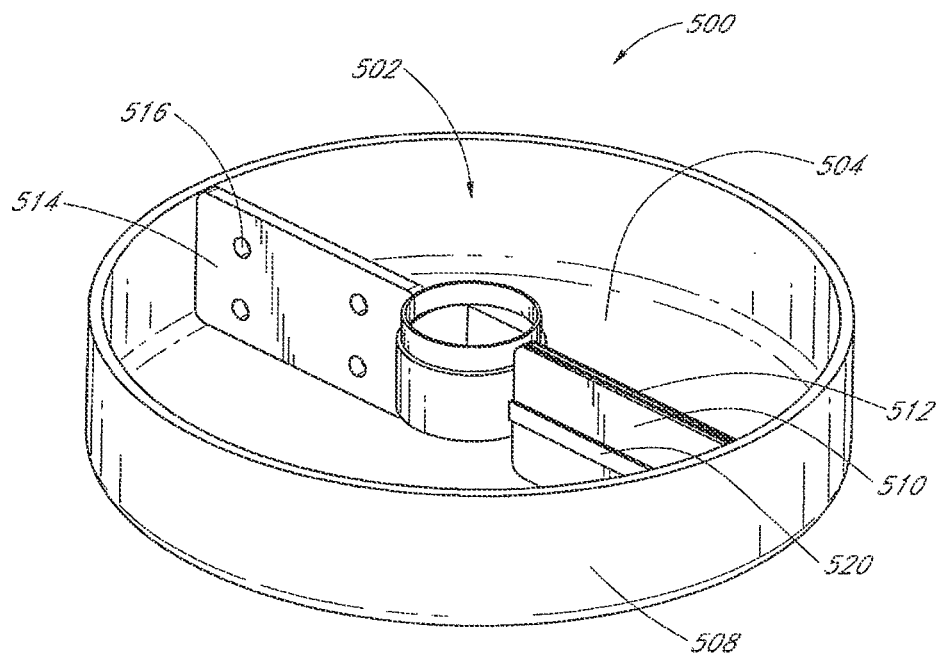
FIG. 30 is a perspective view of the rotary damper of FIG. 29, with a portion of the housing removed.

Referring now to FIGS. 29-30, a rotary damper is illustrated. The apparatus includes a housing 500 defining a housing interior 502 for containing damper fluid (not shown) of any conventional nature. The housing interior has a substantially circular cross section and is formed by a toroidal or cylindrical (illustrated) inner housing surface 504 disposed about and spaced from a central axis 470. The housing 500 includes two adjoining housing members 506, 508, each housing member defining a portion of the housing interior.

A vane or piston 510 having an outer peripheral piston surface at which is located an outer seal 512 is in substantially fluid-tight, slidable engagement with the inner housing surface, spaced from axis 470 and disposed along a common plane with the axis 470. The housing 500 and the piston 510 are relatively rotatably moveable about the axis, as will be described in greater detail below.

A fluid barrier 514 in the form of a plate is immovably attached to the housing and positioned in the housing interior.

The fluid barrier 514 defines multiple flow control orifices or passageways 516 which permit restricted passage of damper fluid therethrough responsive to relative rotational movement between the piston 510 and the housing to dampen forces applied to the apparatus causing the relative rotational movement.

A shaft or aperture 518 extends through the housing interior along axis 470 and projects outwardly from at least one opposed side of the housing, the shaft passing through openings of the housing.

Piston 510 is secured to shaft 518 such as by radially extending arm 520 affixed to shaft. Relative rotational movement between the housing and the aperture 518 causes the piston 510 to rotate about axis 470. This will cause damper fluid in the housing interior to pass through flow control passageways 516 and thus resist the relative rotational movement.

Any of a variety of alternative specific damper constructions may be utilized as will be apparent to those of skill in the art. Linear dampers may also be used, along with associated lever arms, or mounted in line in a pulley system.

Figure 31:
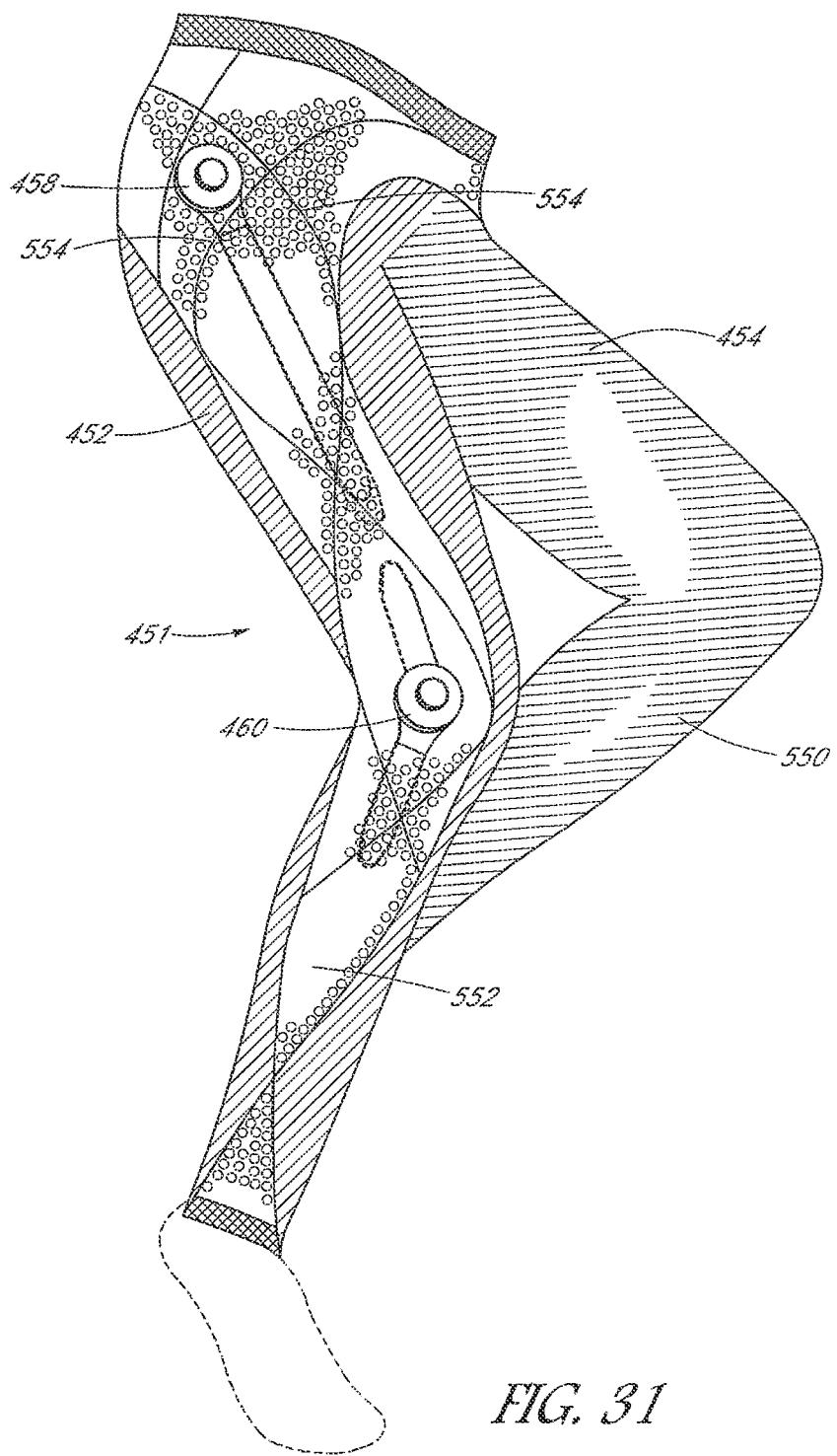
FIG. 31 is a side view of an athletic training garment incorporating hip and knee resistance units and technical fabric features of the present invention.

Referring to FIG. 31, there is illustrated a training garment 451 having a right leg 452 and a left leg 454. The training garment 451 is similar to the toning garment 450 shown in FIG. 34, although may have more technical fabric and potentially higher or different resistance characteristics.

The training garment preferably comprises at least one stretch panel 550, for providing a snug fit and optional compression. The panel may exhibit stretch in at least a circumferential direction around the leg and waist. Stretch panel 550 may comprise any of a variety of fabrics disclosed elsewhere herein. The panel may include woven textile having yarns at least partially formed from any of polyamide, polyester, nylon, spandex, wool, silk, or cotton materials, for example. More particularly, the yarns may be eighty percent polyamide and twenty percent spandex in some configurations. When formed from a combination of polyamide and spandex, for example, the stretch woven textile may exhibit at least thirty percent stretch prior to tensile failure, but may also exhibit at least fifty percent or at least eighty percent stretch prior to tensile failure. In some configurations of garment 451, the stretch in stretch woven textile may equal or exceed one-hundred percent prior to tensile failure. The optimal amount of stretch will normally be the maximum stretch that still allows the wearer to move comfortably with maximum force transfer between the wearer's movement and movement of the resistance units. Too much stretch in a direction of force imposed by the resistance unit will allow the fabric to stretch rather than transfer all of the wearer's motion to the resistance unit.

At least one and in some implementations at least two or three or more technical fabric support panels 552 are provided on each of the right and left legs, to facilitate force transfer between the wearer and the hip resistance unit 458 and, when present, the knee resistance unit 460. The technical support panel 552 may be provided with at least one and normally a plurality of reinforcement strands 554 extending along a pattern to facilitate force transfer and maintaining fit of the garment throughout the range of motion in opposition to the resistance provided by the resistance unit. The technical fabric support panel 552 may be positioned over the entire height of the garment (as illustrated) or may be localized in the vicinity of the resistance units.

Yarns extending along a non-stretch or low stretch axis within non-stretch woven textile panel may be at least partially formed from any of polyamide, polyester, nylon, spandex, wool, silk, cotton or other high tensile strength strands disclosed herein. Depending upon the materials selected for the yarns, non-stretch woven textile may exhibit less than ten percent stretch prior to tensile failure, but may also exhibit less than five percent stretch or less than three percent stretch at least along the non-stretch axis prior to tensile failure.

A plurality of different panels of each of stretch woven textile and non-stretch woven textile may be joined to form garment 451. That is, garment 451 may have various seams that are stitched or glued, for example, to join the various elements of stretch woven textile and non-stretch woven textile together. Edges of the various elements of stretch woven textile and non-stretch woven textile may be folded inward and secured with additional seams to limit fraying and impart a finished aspect to the garment. The garment 451 may be provided with one or more zippers, hook and loop fasteners or other releasable fasteners disclosed herein, such as one extending the full or partial length of one or both legs, to facilitate getting into and out of the garment. One or more non-stretch panels may be removably secured to the garment using a zipper or equivalent structure, hook and loop sections or otherwise. This enables the garment to be pulled on in a relatively stretchable mode. Following proper positioning of the garment on the wearer, force transfer features such as one or more low stretch features such as in the form of straps or panels can be secured to or tightened on the garment to reduce the stretch along the axes which will experience the most tensile force from the resistance units during motion of the wearer.

In general, the low stretch axis will be aligned in the anterior-posterior direction, or at least have a vector resolution component in the anterior posterior direction particularly for the femoral lever. Generally the low stretch axis will be within about 45 degrees up or 45 degrees down of horizontal, with the garment in the normal standing (vertical) orientation. The non stretch axis of the fabric at the hip will be oriented to resist rotation of the docking station, and thus will be oriented differently depending upon the presence or absence of an elongate, structural lever arm.

Stretch panels may be formed in the configuration of straps, having a length that exceeds the width, and constructed similar to the watersport waist band of U.S. Pat. Nos. 7,849,518 or 8,555,415, previously incorporated herein. The longitudinal axis of the strap may extend circumferentially around the waist or leg above and or below each resistance unit to cooperate with the lever or other force transfer structure to shield the stretch fabric from tensile force. Alternatively, if less constriction on fit is desired, the axis of the strap may be angled up or down with respect to horizontal to extend in a spiral path which extends at least about 20%, often at least about 50% and in some embodiments at least about 75% or 100% or more of the circumference of the wearer's leg or waist. See FIG. 13 which can illustrate a non-stretch strap configuration which may be embedded within or over a multilayer stretch fabric panel garment.

Resistance garments in accordance with the present invention can be configured as independent biometric sensing and feedback devices, or can be configured to communicate and/or cooperate with external electronic systems and devices, such as cell phones, the internet, local area networked devices and particularly activity tracking devices such as those produced by Fitbit, Inc., San Francisco, Calif. (see, for example, U.S. patent application Ser. No. 13/156,304, filed on Jun. 8, 2011, entitled "Portable Monitoring Devices and Methods of Operating Same" which is incorporated herein by reference in its entirety).

Biometric and/or ambient condition, spatial location, motion or other sensors and processing circuitry may be integrated into the garment or other support associated with the resistance element, or may be separately worn by the wearer such as when the garment is configured to pair with a wearable activity tracker such as any of a variety of Fitbit models. One or more sensors carried by the garment or the wearer of the garment can include, for example, electromyography (EMG), electrocardiograph (ECG), respiration, galvanic skin response (GSR), temperature, acceleration, bend angle, pressure, force, torque, GPS, accelerometer (single or multi axis), respiration, perspiration, bioimpedence, gyroscopes, various rate measurements such as stride rate, flex rate, pulse (heart) rate, spatial orientation, deviation or position, oxygen saturation, blood glucose, or others described elsewhere herein. Sensors may also be provided to detect, measure and/or sense data which is representative of hydration, height, weight, sun exposure, blood pressure and/or arterial stiffness. See, for example, U.S. patent application Ser. No. 14/476,128, filed on Sep. 3, 2014, entitled "Biometric Monitoring Device Having a Body Weight Sensor and Methods of Operating Same" which is incorporated herein by reference in its entirety). The use of multiple sensors for the same parameter or multiple sensors for multiple parameters may provide a level of insight that is not available by measuring only a single metric such as heart rate (HR) or motion based on accelerometers or other types of motion sensors (e.g., a gyroscope). Sensors may be incorporated in a permanent manner into the fabric of the form-fitting interactive garment itself or in a detachable manner such as with zippers, snap fit connectors, clasps, hook and loop (Velcro) or other releasable connectors and/or in pockets or under or on top of flaps if desired, to allow removal and/or repositioning of the sensors.

Biometric or other data parameters and/or data derived from biometric or other parameters can be displayed and/or stored for subsequent display in a form that indicates an incremental effect of the resistance provided by a resistance element in accordance with the present invention. For example, a wearer might walk for 1,000 actual steps. If those steps were taken while wearing a resistance garment as disclosed herein, a 'steps equivalent' may be calculated and displayed indicating the equivalent number of steps that would have been required to have been taken to have burned an equivalent amount of calories or perform an equivalent amount of work. So the 1,000 steps with a first resistance level rating might be an equivalent amount of work to 1,100 actual steps without the resistance unit. Thus the resistance garment produced an incremental 10% energy burn or effort over steps taken without the resistance elements. A second resistance level unit might enable 1,000 steps to be equivalent to 1200 steps without the resistance unit. Fixed resistance units can be provided at a variety of resistance levels, configured to produce an incremental burden of at least about 10%, 20% 30%, 50% 75% or more in excess of the burden incurred by the activity such as walking in the absence of the resistance unit. In configurations designed more for athletic training than toning, potentially incremental loads of at least about 100% or 150% or 200% or more over the unburdened baseline may be desirable.

The incremental effect of the resistance units can be expressed in various other ways, such as incremental power (Watts) or incremental calories burned. So if 2,500 steps would normally burn 1100 calories for a particular wearer in the absence of a resistance garment, the same 2500 steps might burn at least about 10% or 20% or 30% or 50% or more incremental calories for the same 2500 steps while wearing a resistance garment. The incremental effect can alternatively be calculated as an effective slope equivalent. A baseline slope can be selected, such as horizontal. Walking along a substantially horizontal surface while wearing a resistance garment, depending upon the resistance level, might be the equivalent of walking uphill along a slope of plus at least about 4 degrees, at least about 10 degrees, at least about 15 degrees at least about 20 degrees or more.

Incremental elevation or change of respiration rate, pulse rate, blood gas such as $CO_2$ or $O_2$, temperature, blood glucose may be measured or calculated, so that the wearer, care provider or friends connected via social media or other networking environment can see the physiological benefit provided by wearing the resistance units of the present invention.

Synchronization between the wearable resistance device and a wearable activity tracker can be accomplished either automatically (e.g. wirelessly) or manually. For example, in the example above of a resistance garment carrying a resistance unit which is rated to provide an incremental 20% calorie burn or resistance to walking, a code carried by the resistance unit corresponding to the level of resistance can be input into the activity tracker, and the activity tracker programmed to calculate the parameter equivalent accomplished by the wearer while utilizing that resistance element. So the activity tracker can reflect that the actual 1000 steps with the resistance unit was the equivalent of 1200 steps without the resistance unit.

More simply, the activity tracker can be programmed to receive an input of a factor corresponding to the resistance value of a particular resistance unit. The factor would cause the activity tracker to report the effective value (e.g., 115 steps) rather than or in addition to the actual value (e.g., 100 steps) for the parameter of interest.

Alternatively, the activity tracker may be caused to periodically or on-demand ping an interrogator signal. The resistance element or the garment carrying the resistance element may be provided with a RFID or other identification tag or circuit which can reflect a signal back to the activity tracker, indicating the resistance rating. The activity tracker can then calculate an equivalent value for a parameter of interest being displayed or available for display, indicating the incremental change relating to that parameter caused by the resistance element. In more complex systems, the resistance element, activity tracker and optionally sensors carried by the garment can be in communication using any of a variety of wired or wireless protocols such as ANT, ANT+, Bluetooth, WiFi, ZigBee or others known in the art.

Thus, an activity tracker configured to pair with the resistance garment of the present invention may be provided with an input, configured to receive a compensation factor which will enable conversion of a measured or calculated parameter into an equivalent, taking into account the effect of the resistance units on the measured parameter. The input may be configured for the user to manually input the compensation factor. Alternatively, the input may be configured to wirelessly receive the compensation factor from the resistance unit. The activity tracker may be configured to record and or display or output the equivalent value, and optionally also the actual value of the parameter of interest. For example, the activity tracker may be configured for receiving an input indicating that each actual step will require the wearer to exert 1.2 steps worth of effort. The activity tracker will therefore display 120 step equivalents for every one hundred actual steps taken by the wearer, while the corresponding resistance element is engaged.

For embodiments of the present invention utilizing a viscous damper, the resistance to movement will vary as a function of angular velocity. For any of the embodiments disclosed herein, and particularly for viscous damper embodiments, it may therefore be desirable to measure actual power rather than merely calculating a metric of work based upon the number of repetitions. Preferably, the level of exertion will be described in terms of wattage (intensity) and Joules of work (quantity) being done, from which calories burned can be determined and displayed or saved.

A variety of power sensors are known in the performance bicycle arts, which may be readily adapted for use in the present context. Typically, a power sensor such as a strain gauge will be positioned such that it captures force exerted by the wearer. Power sensors maybe positioned in a variety of locations on the garment, such as on the anterior side and or posterior side of the lower limit of the garment (knee or ankle), and/or carried by the resistance unit and its attachment structures. Torque or other angular sensors may be attached to the resistance unit, and/or the mounting station for receiving the resistance unit. All may be provided with wired or wireless communication back to a central processing unit carried by the garment, or to a remote device such as the activity tracker, cell phone, or other as has been described. Although power output by the wearer is perhaps most conveniently measured by utilizing the relative rotation of the femoral lever with respect to the hip, wireless power output sensors may be positioned elsewhere in the garment, and configured such as those disclosed in United States patent publication 2015/0057128 to Ishii, the disclosure of which is hereby incorporated in its entirety herein.

Figure 33:
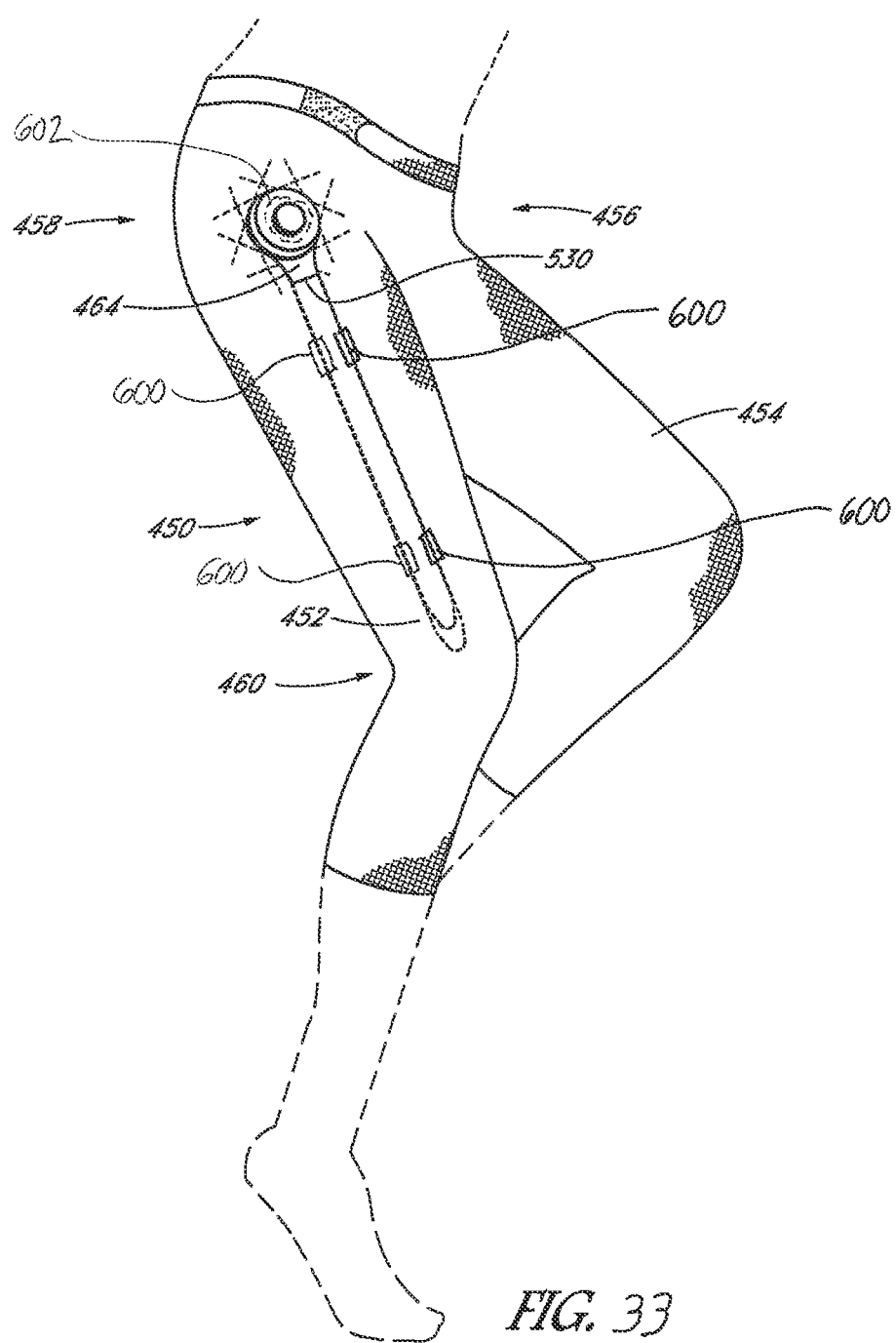
FIG. 33 is a side elevational view as in FIG. 27, including force sensors to determine power exerted and or calories burned.

Any of the configurations disclosed herein may additionally be configured to determine and display a metric of total or incremental power (e.g., in Watts) expended by the wearer, or incremental calories burned, as a result of movement against the resistance provided by the resistance unit. For example, referring to FIG. 33, at least one or two or more sensors 600 may be positioned in the force path between a first surface connected to the resistance element such as on the femoral lever arm, and a second surface mechanically connected to the wearer, such as an interior opposing force transmission surface within the sleeve. Split lever arms may also be provided with a sensor positioned to be under compression or shear between a first and second surfaces on corresponding first and second portions of the lever arm when the wearer moves against the resistance.

In one configuration, at least a first, anterior sensor is provided on an anteriorly facing surface carried by the lever arm. The first anterior sensor will be under compression as the wearer moves their leg rearward (in extension). At least a first posterior sensor is provided on a posteriorly facing surface carried by the lever arm. The first posterior sensor will be under compression as the wearer moves their leg forward (in flexion). Two or three or more sensors may be provided to measure force upon flexion or extension such as to improve accuracy of the reading.

Alternatively, force sensors 602 may be mechanically connected to the shaft or otherwise configured to measure force at the point of rotation as in understood in the art. Signals from any or a combination of sensors 600 and 602 may be used to calculate a metric of power expended by the wearer to move against resistance provided by the resistance element. One system having strain gauges embedded in the hub of a rotating construct for the purpose of measuring power is disclosed in U.S. Pat. No. 6,418,797 to Ambrosina et al., the disclosure of which is hereby incorporated in its entirety herein by reference. In another construction, the axel or post 474 is configured to undergo slight deformation in response to applied torque, and sensors are positioned to measure strain as that deformation occurs. Additional details may be found in U.S. Pat. No. 6,356,847 to Gerlitzki, the disclosure of which is hereby incorporated in its entirety herein by reference.

The determination of expended power can be accomplished on only one of the right side or left side of the wearer, such as at the right hip or hip plus knee but not the opposing side. The value can be doubled, under the assumption that the wearer's exertion will be bilaterally symmetrical. Preferably, the force sensor system will be bilaterally symmetrical on both the right and left side of the wearer, to allow the wearer to evaluate any asymmetries in power output.

Figure 34:
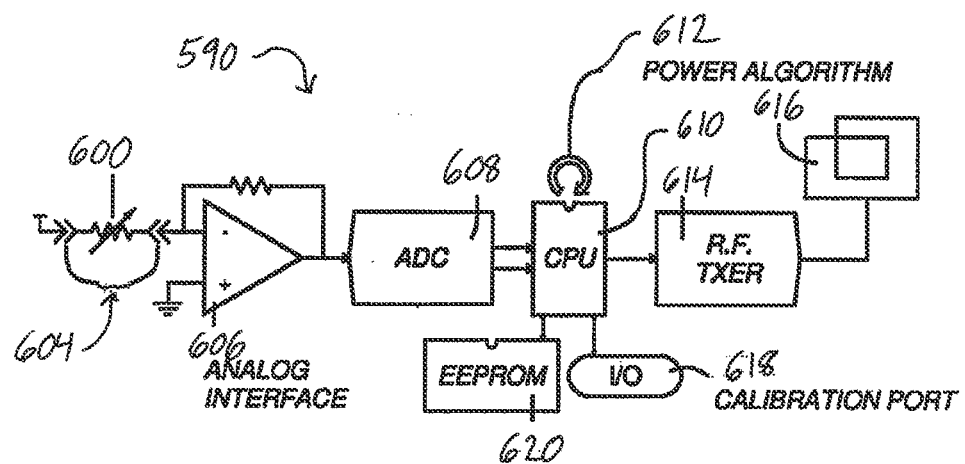
FIG. 34 is a block diagram of sensor electronics.

A block diagram showing functional components of an electronics unit 590 is shown in FIG. 34. Force sensor 600 is connected via wire interface 604. A sensor such as a Flexiforce sensor (obtained from Tekscan of South Boston, Mass., www.tekscan.com) may be used, having a conductance which is linear with force, and an analog interface 606 is used to generate an output voltage that is linear with the applied force. Other analog interfaces may not generate an output voltage that is linear with force, but they will generate a voltage that has a predetermined relationship to a force sensed by the force sensor. The analog interface 606 may contain a variable reference circuit for adjusting a range of the output voltage, depending on the desired performance. The voltage output by the analog interface 606 drives an analog-to-digital converter 608, which is controlled by a central processing unit (CPU) 610 and sampled at a known and constant rate. The CPU 610 may be, for example, a microprocessor or a digital signal processor. The CPU 610 is responsible for executing a power algorithm 612 that calculates the wearer's power exerted to overcome the resistance element based on force sensed by the force sensor 600. Data resulting from the calculation is transmitted to a remote electronics unit (activity tracker, cell phone, heads up display, wrist worn display, internet, etc.) by a radio frequency transmitter 614 and antenna 616 via a data channel. During calibration mode, calibration port 618 is used to interface to electronics unit 590. EEPROM memory 620 stores data generated during calibration. Operating power is supplied, for example, by a battery driven power supply, which is not shown but is very well known in the art. Some sensors are preferably calibrated (zeroed) and may be susceptible to drift with changing temperature. A temperature compensation circuit (not shown) is preferably included, to determine the temperature of the sensor and compensate for thermally induced error.

Figure 35:
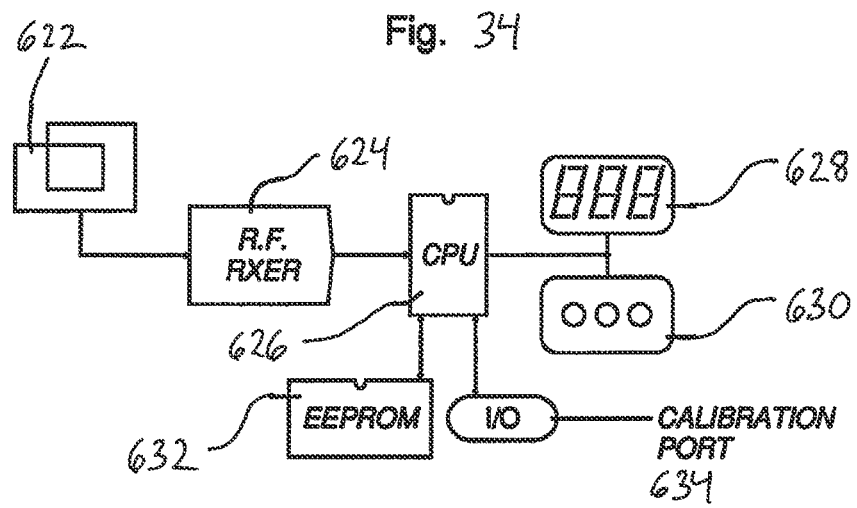
FIG. 35 is a block diagram of a remote display unit.

FIG. 35 is a block diagram showing functional components of a remote electronics unit that may display power or calories burned data to the wearer, coach or other application. An antenna 622 and a radio frequency receiver 624 receive data transmitted via the data channel. A CPU 626 controls the user interface, which may include a display 628 and potentially controls such as switches 630. Calibration data and user data are stored in EEPROM memory 632. During calibration mode, calibration port 634 is used to interface to the electronics unit. Operating power for the electronics unit may be supplied, for example, by a battery driven power supply, which is not shown but is very well known in the art. Additional details may be found in U.S. Pat. No. 7,599,806 to Hauschildt, the disclosure of which is hereby incorporated in its entirety herein by reference.

Power may be displayed as real time data, peak, average, rolling average or integrated over a predetermined interval of time (e.g., 10 second, 30 second, 1 minute or more). Display may be visual, such as on a smart phone, activity tracker or other hand held, wrist worn or mounted device. Power may alternatively be displayed on a heads up display such as an eyeglass with heads up display, or audibly over an audio output using a text to voice converter. Display may alternatively be configured to provide an indication of crossing a preset value such as when power output moves either above or below a preset upper or lower alarm limit.

Figure 36:
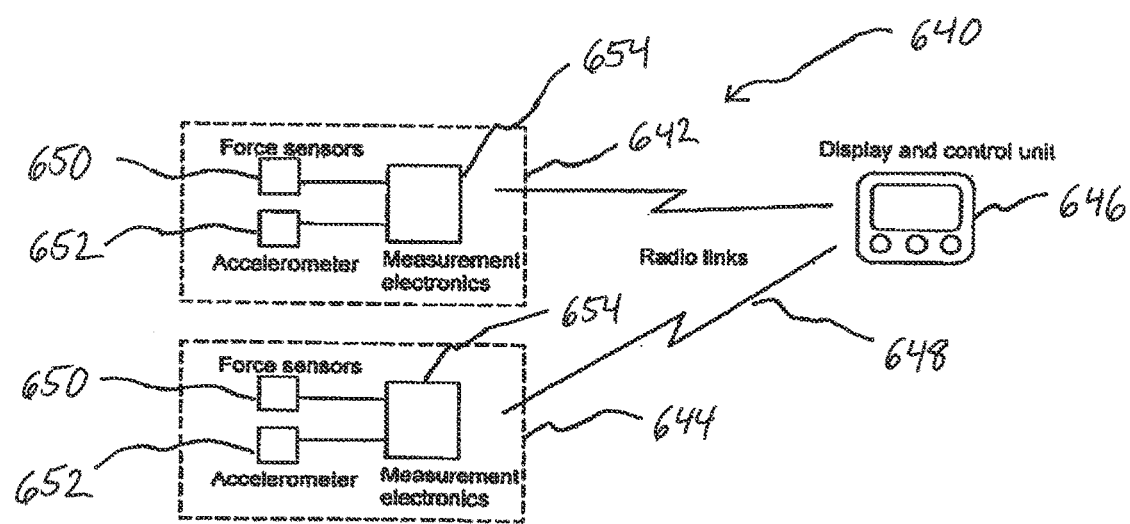
FIG. 36 is a block diagram of a bilateral power measurement system.

Referring to FIG. 36 there is illustrated a simplified bilateral system to implement the present invention indicated generally by the reference numeral 640. A left leg power module 642 and a right leg power module 644 are indicated by dotted lines and are in communication with a control and display unit 646, for example over a radio link 648 (e.g., ANT+, Bluetooth, Zigbee or others disclosed elsewhere herein). Each module 642, 644 comprises of one or more force sensor(s) 650, an accelerometer 652 and related measurement electronics 654 carried by each module. The display and control unit 646, usually battery powered, can be attached to any convenient place such as the the wrist of the wearer or other display as has been discussed. The connection between the sensors and electronics in the module and the sensors and electronics elsewhere on or in communication with the garment or wearer may be by wired conductors on or integrated into the garment, or may be by a wireless link such as radio protocols described elsewhere herein or by electromagnetic induction.

In a preferred embodiment the communication between the power module electronics embedded in the resistance module and the display and control unit is by a radio link 648. Each of left leg power module 642 and right leg power module 644 uses the radio to transmit a set of measurement data at one or more fixed points on each stride. In operation each of the power modules 642, 644 transmits its data in a short burst when the stride reaches a fixed point in its cycle, such as at the heel strike or toe roll off. Because the two strides are 180 degrees away from each other, data transmission can be timed to ensure that the transmissions from each power module assembly will never interfere with each other. Each burst of data contains a set of samples or measurements taken at regular intervals during the stride cycle, and may include force, cadence, femoral (or other) extension angle and accelerometer information. Each sample has an associated timestamp, which may be explicit or implicit, to specify its time relationship to the other samples in the set and to other sets of samples. The electronics in the power modules may include processing of the data before it is transmitted to the control unit 646. Additional details may be found in U.S. Pat. No. 8,762,077 to Redmond, et al., the disclosure of which is hereby incorporated in its entirety herein by reference.

It may be desirable to monitor the wearer's oxygen saturation, to evaluate the transition between aerobic and anaerobic threshold as well as the effect on that threshold of varying the degree of resistance provided by the resistance unit (by adjusting an adjustable resistance unit or switching resistance units having different resistance levels). A sensor may be configured to be placed in contact with the wearer such as by permanent or removable attachment to the garment, or independent attachment to the wearer. The sensor may be configured to obtain a plethysmography signal, although it should be understood that any device configured to obtain oxygen saturation and/or heart rate data may be used in accordance with the techniques of the present disclosure. The system may include a monitor in communication with the sensor. The sensor and the monitor may communicate wirelessly as shown, or may communicate via one or more cables (e.g., the sensor and the monitor may be coupled via one or more cables). The sensor may include a sensor body, which may support one or more optical components, such as one or more emitters configured to emit light at certain wavelengths through a tissue of the subject and/or one or more detectors configured to detect the light after it is transmitted through the tissue of the subject.

The sensor may include one or more emitters and/or one or more detectors. The emitter may be configured to transmit light, and the detector may be configured to detect light transmitted from the emitter into a patient's tissue after the light has passed through the blood perfused tissue. The detector may generate a photoelectrical signal correlative to the amount of light detected. The emitter may be a light emitting diode, a superluminescent light emitting diode, a laser diode or a vertical cavity surface emitting laser (VCSEL). Generally, the light passed through the tissue is selected to be of one or more wavelengths that are absorbed by the blood in an amount representative of the amount of the blood constituent present in the blood. The amount of light passed through the tissue varies in accordance with the changing amount of blood constituent and the related light absorption. For example, the light from the emitter may be used to measure blood oxygen saturation, water fractions, hematocrit, or other physiological parameters of the patient. In certain embodiments, the emitter may emit at least two (e.g., red and infrared) wavelengths of light. The red wavelength may be between about 600 nanometers (nm) and about 700 nm, and the IR wavelength may be between about 800 nm and about 1000 nm. However, any appropriate wavelength (e.g., green, yellow, etc.) and/or any number of wavelengths (e.g., three or more) may be used. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

The detector may be an array of detector elements that may be capable of detecting light at various intensities and wavelengths. In one embodiment, light enters the detector after passing through the tissue of the wearer. In another embodiment, light emitted from the emitter may be reflected by elements in the wearer's tissue to enter the detector. The detector may convert the received light at a given intensity, which may be directly related to the absorbance and/or reflectance of light in the tissue of the wearer, into an electrical signal. That is, when more light at a certain wavelength is absorbed, less light of that wavelength is typically received from the tissue by the detector, and when more light at a certain wavelength is transmitted, more light of that wavelength is typically received from the tissue by the detector. After converting the received light to an electrical signal, the detector may send the signal to the monitor, where physiological characteristics may be calculated based at least in part on the absorption and/or reflection of light by the tissue of the wearer.

As indicated above, the monitoring system may be configured to monitor the wearer's oxygen saturation and/or heart rate during exercise. The system may also be configured to determine whether the wearer is utilizing an aerobic or an anaerobic pathway based at least in part on the athlete's oxygen saturation and/or heart rate. For example, the monitoring system may compare the athlete's oxygen saturation and/or heart rate to one or more zones corresponding to various types of exercise (e.g., aerobic exercise and anaerobic exercise) to determine whether the wearer is utilizing the aerobic or the anaerobic pathways. Each of the one or more zones may be defined by a percentage or a range of percentages of oxygen saturation and/or a value or a range of values of heart rate, and each of the one or more zones may have an upper limit and a lower limit for oxygen saturation and/or heart rate. For example, a first zone may include an oxygen saturation range and/or a heart rate range corresponding to aerobic exercise, while a second zone may include an oxygen saturation range and/or heart rate range corresponding to anaerobic exercise. A visual, audio and/or tactile display or feedback may be provided to the wearer to indicate status and/or change in status between an aerobic metabolism level of activity and an anaerobic metabolism level of activity. Additional implementation details may be found in US patent publication No. 2015/0031970 to Lain, entitled Systems and Methods for Monitoring Oxygen Saturation During Exercise, the disclosure of which is hereby incorporated by reference in its entirety herein.

Although disclosed primarily in the context of lower body garments, any of the resistance elements and attachment fabrics and structures disclosed herein can be adopted for use for any other motion segment on the body, including the shoulder, elbow, wrist, neck, abdomen (core) and various other motion segments of the upper body. Any of the various resistance elements and attachment structures disclosed herein can be interchanged with any other, depending upon the desired performance. In addition, the present invention has been primarily disclosed as coupled to a type of garment resembling a complete article of clothing such as that illustrated in FIG. 31. However any of the resistance systems disclosed herein may be carried by any of a variety of braces, wearable clothing subassemblies, straps, cuffs or other wearable support construct that is sufficient to mechanically couple one or more resistance elements to the body and achieve the force transfer described herein, that may be worn over or under conventional clothing.

What is claimed is:

1. A modular resistance unit for releasable connection to a toning garment, comprising:
    a femoral lever having a proximal end and a distal end, a thickness and a width that exceeds a thickness, the lever arm conformable to the leg of a wearer when mounted on the toning garment such that the width faces the leg of a wearer in an as worn orientation;
    a resistance unit carried by the proximal end of the lever;
    a coupling on the resistance unit, for releasable coupling to a complementary coupling carried by the garment;
    configured such that when the femoral lever is secured to the leg of the garment, the coupling on the resistance unit is connected to the complementary coupling on the garment and the garment is worn by a wearer, the modular resistance unit provides resistance to movement at the wearer's hip.

2. A modular resistance unit as in claim 1, wherein the coupling comprises an aperture for receiving a post carried by the garment.

3. A modular resistance unit as in claim 1, further comprising a lock for locking the coupling on the resistance unit to the complementary coupling carried by the garment.

4. A modular resistance unit as in claim 1, further comprising a sensor to determine force applied against the resistance unit during extension.

5. A modular resistance unit as in claim 1, further comprising a sensor to determine force applied against the resistance unit during flexion.

6. A modular resistance unit as in claim 1, further comprising a sensor for determining extension angle of the leg.

7. A modular resistance unit as in claim 1, further comprising a processor, configured for determining power exerted throughout the range of motion.

8. A modular resistance unit as in claim 7, further comprising a transmitter, for transmitting data to a remote device.

9. A modular resistance unit as in claim 6, further comprising a transmitter, for transmitting angular velocity data to a remote device.

10. A modular resistance unit as in claim 1, wherein the resistance unit comprises a rotatable viscous damper.

11. A modular resistance unit as in claim 1, wherein the resistance unit is removably connectable to the garment.

12. A modular resistance unit as in claim 4, wherein the force sensor is in force transmitting contact with the femoral lever.

13. A modular resistance unit as in claim 1, comprising a processor configured to output an indication of when power output crosses a preset value.

14. A modular resistance unit as in claim 13, wherein the processor is configured to output an indication of when power output has moved above a preset value.

15. A modular resistance unit as in claim 13, wherein the processor is configured to output an indication of when power output has moved below a preset value.

16. A modular resistance unit as in claim 1, wherein the resistance unit imposes a resistance of at least about 5 inch pounds.

17. A modular resistance unit as in claim 16, wherein the resistance unit imposes a resistance of at least about 10 inch pounds.

18. A modular resistance unit as in claim 16, wherein the resistance unit imposes a resistance of at least about 15 inch pounds.

19. A modular resistance unit as in claim 9, wherein the transmitter is an ANT+configured transmitter.

20. A modular resistance unit as in claim 9, wherein the transmitter is a Bluetooth configured transmitter.

21. A modular resistance unit as in claim 1, configured to determine incremental power exerted to overcome resistance imposed by the resistance element.

\* \* \* \* \*